United States Patent
Chaiken et al.

(10) Patent No.: US 12,421,279 B2
(45) Date of Patent: Sep. 23, 2025

(54) CYCLIC PEPTIDE ANTIVIRAL AGENTS AND METHODS USING SAME

(71) Applicant: Drexel University, Philadelphia, PA (US)

(72) Inventors: Irwin M. Chaiken, Gladwyne, PA (US); Adel Ahmed Rashad Ahmed, Philadelphia, PA (US)

(73) Assignee: Drexel University, Philadelphia, PA (US)

( * ) Notice: Subject to any disclaimer, the term of this patent is extended or adjusted under 35 U.S.C. 154(b) by 0 days.

(21) Appl. No.: 18/589,590

(22) Filed: Feb. 28, 2024

(65) Prior Publication Data

US 2025/0059235 A1    Feb. 20, 2025

Related U.S. Application Data

(63) Continuation of application No. 17/552,087, filed on Dec. 15, 2021, now abandoned, which is a continuation of application No. 16/331,861, filed as application No. PCT/US2017/051380 on Sep. 13, 2017, now abandoned.

(60) Provisional application No. 62/526,179, filed on Jun. 28, 2017, provisional application No. 62/394,494, filed on Sep. 14, 2016.

(51) Int. Cl.
| | |
|---|---|
| *A61K 38/12* | (2006.01) |
| *A61K 47/69* | (2017.01) |
| *A61P 31/18* | (2006.01) |
| *C07K 7/56* | (2006.01) |
| *A61K 38/00* | (2006.01) |

(52) U.S. Cl.
CPC ............ *C07K 7/56* (2013.01); *A61K 47/6923* (2017.08); *A61K 47/6929* (2017.08); *A61P 31/18* (2018.01); *A61K 38/00* (2013.01)

(58) Field of Classification Search
None
See application file for complete search history.

(56) References Cited

U.S. PATENT DOCUMENTS

| | | | |
|---|---|---|---|
| 7,556,808 B2 | 7/2009 | Hosahudya et al. | |
| 8,575,095 B2 | 11/2013 | Chaiken et al. | |
| 8,951,963 B2 | 2/2015 | Chaiken et al. | |
| 9,233,138 B2 | 1/2016 | Abrams et al. | |
| 10,251,931 B2 | 4/2019 | Chaiken et al. | |
| 2012/0165250 A1 | 6/2012 | Chaiken et al. | |
| 2016/0151365 A1 | 6/2016 | Planelles et al. | |

FOREIGN PATENT DOCUMENTS

WO    2016094518 A2    6/2016

OTHER PUBLICATIONS

PCT International Search Report issued for corresponding PCT Application No. PCT/US2017/051380 dated Jan. 23, 2018.
CID: 122190307, PubChem Compound Database, National Center for Biotechnology Information; https://pubchem.ncbi.nlm.nih.gov/compound/1222190307, Oct. 2016.
Adessi , et al., "Converting a peptide into a drug: strategies to improve stability and bioavailability.", Curr. Med. Chem., 9, 2002, 963-978.
Gopi , et al., "Click Chemistry on Azidoproline: High Affinity Dual Antagonist for HIV-1 Envelope Glycoprotein gp120", ChemMedChem 1, 2006, 54-57.
Rashad , et al., "Chemical optimization of macrocyclic HIV-1 inactivators for improving potency and increasing the structural diversity at the triazole ring", Organic and Biomolecular Chemistry, vol. 15, Jul. 2017, 7770-7782.
Rashad , et al., "Macrocyclic Envelope Glycoprotein Antagonists that Irreversibly Inactivate HIV-1 before Host Cell Encounter", J Med Chem. 58(18), Sep. 2015, 7603-7608.

*Primary Examiner* — Fred H Reynolds
(74) *Attorney, Agent, or Firm* — Saul Ewing LLP; Domingos J. Silva; Dennis Ostrovsky

(57) ABSTRACT

The present invention includes novel cyclic peptides, and methods of using the same. The present invention further includes novel cyclic peptides conjugated with a gold nanoparticle, and methods of using the same.

6 Claims, 14 Drawing Sheets

Specification includes a Sequence Listing.

36, IC$_{50}$ ~ 100 nM

37, IC$_{50}$ ~ 400 nM

38

SEQUENCE LISTING

```
Sequence total quantity: 5
SEQ ID NO: 1            moltype = AA  length = 12
FEATURE                 Location/Qualifiers
REGION                  1..12
                        note = Chemically synthesized
MOD_RES                 6
                        note =
                        (2,4)-4-(4-ferrocenyl-1H-1,2,3-triazol-1-yl)pyrrolidine-2-c
                        arboxylic acid
MOD_RES                 12
                        note = amidated C-terminus
source                  1..12
                        mol_type = protein
                        organism = synthetic construct
SEQUENCE: 1
RINNIPWSEA MM                                                              12

SEQ ID NO: 2            moltype =     length =
SEQUENCE: 2
000

SEQ ID NO: 3            moltype =     length =
SEQUENCE: 3
000

SEQ ID NO: 4            moltype =     length =
SEQUENCE: 4
000

SEQ ID NO: 5            moltype =     length =
SEQUENCE: 5
000
```

CYCLIC PEPTIDE ANTIVIRAL AGENTS AND METHODS USING SAME

CROSS-REFERENCE TO RELATED APPLICATIONS

This application is a continuation of U.S. patent application Ser. No. 17/552,087, filed Dec. 15, 2021, now abandoned, which is a continuation of U.S. patent application Ser. No. 16/331,861, filed Mar. 8, 2019, now abandoned, which is a 35 U.S.C. § 371 national phase application from, and claims priority to, International Application No. PCT/US2017/051380, filed Sep. 13, 2017, and published under PCT Article 21 (2) in English, which claims priority to U.S. Provisional Patent Applications No. 62/394,494, filed Sep. 14, 2016, and No. 62/526,179, filed Jun. 28, 2017, all of which disclosures are incorporated herein by reference in their entireties.

STATEMENT REGARDING FEDERALLY SPONSORED RESEARCH OR DEVELOPMENT

This invention was made with government support under GM056550 awarded by National Institutes of Health. The government has certain rights in the invention.

SEQUENCE LISTING

The instant application contains a Sequence Listing which has been submitted electronically in ASCII format and is hereby incorporated by reference in its entirety. The ASCII file, created on Feb. 28, 2024 is named "046528-7073US3 Sequence Listing.xml" and is 3,719 bytes in size.

BACKGROUND OF THE INVENTION

The human immunodeficiency virus-1 (HIV-1) is responsible for a global epidemic, with over 33 million infected people worldwide. The lifecycle of HIV-1 has been extensively studied in the hope of identifying a therapeutic intervention that blocks viral transmission or viability. As an example, the Highly Active Anti-Retroviral Therapy (HAART) is a therapeutic approach targeting one or more stages of the HIV-1 life cycle. Favorable clinical results with HAART have shown that simultaneously targeting distinct stages of the viral life cycle may reduce the viral evolutionary escape mechanism that leads to drug resistance. Further, HAART may be more effective if administered simultaneously with other drugs that interrupt the initial entry stage of the virus life cycle. Unfortunately, existing entry inhibitors suffer from weak potency and toxicity issues.

The entry of HIV-1 into the host cell is mediated by interaction of a trimeric gp120/gp41 envelope (Env) protein complex with both cellular CD4 and chemokine co-receptor CCR5 or CXCR4. Each virus Env spike consists of a trimer of two non-covalently associated glycoproteins, an inner gp41 transmembrane protein and an outer gp120 protein. The first step of viral entry is the interaction with CD4, leading to structural changes in the virus Env spike and exposing the chemokine binding domains of gp120. A structural change in the envelope spike exposes the fusion peptide sequence of gp41 and enables the collapse of gp41 into a six-helix bundle, leading to downstream membrane fusion and productive infection.

The HNG class of triazole conjugated peptides was derived from the 12-mer parental peptide 12p1 by converting the proline at residue 6 of 12p1 into an azido-proline and performing copper-catalyzed (2+3) cycloaddition reactions of the azide with substituted acetylenes. As a class, the HNG compounds have enhanced binding affinity for HIV-1 gp120, and block both CD4 and co-receptor sites with great efficacy. The HNG compounds appear to trap the gp120 protein in a non-functional state, distinct from the flexible ground state of gp120 or the CD4 induced conformation, and thus effectively halt the entry process at the initial binding stages. Using pseudotyped HIV-1 as well as isolated recombinant protein mutants, a binding footprint for the ferrocenyl triazole peptides was found to involve D474 and T257. These residues are adjacent to but not directly overlapping the CD4 binding site, and also overlap residues important for BMS-806 inhibition and a recently identified neutralizing antibody epitope. All of the 12p1 family members tested to date inhibit the binding of gp120 to both sCD4 (in a seemingly non-competitive manner) and the co-receptor surrogate mAb17b.

As an example, the ferrocenyl triazole conjugate HNG156 [SEQ ID NO:1, wherein X is (2,4)-4-(4-ferrocenyl-1H-1,2,3-triazol-1-yl)pyrrolidine-2-carboxylic acid; also known as (S)-4-((S)-2-((S)-2-((2S,4S)-1-(L-arginyl-L-isoleucyl-L-asparaginyl-L-asparaginyl-L-alloisoleucyl)-4-(4-ferrocenyl-1H-1,2,3-triazol-1-yl)pyrrolidine-2-carboxamido)-3-(1H-indol-3-yl) propanamido)-3-hydroxypropanamido)-5-(((S)-1-(((S)-1-(((S)-1-amino-4-(methylthio)-1-oxobutan-2-yl)amino)-4-(methylthio)-1-oxobutan-2-yl)amino)-1-oxopropan-2-yl)amino)-5-oxopentanoic acid] binds to monomeric gp120 with a $K_D$ of 7 nM, in contrast to the 2,600 nM $K_D$ value of 12p1. HNG156 inhibition of the co-receptor binding site appears to be allosteric and involves conformational entrapment of Env gp120 into an inactivated state. HNG156 neutralizes viral infection by subtype A, B and C isolates ($IC_{50}$ range=0.08-62.5 µM), but not viruses pseudotyped with VSV-G. HNG156 also exhibits no detectable toxicity in a tissue explants model at concentrations up to 100 µM. Enhancement of lifetime and potency of the HNG compounds could improve their potential as therapeutic and microbicide agents.

There is a need in the art to develop novel compounds that are useful for treating or preventing HIV-1 infection. There is also a need in the art to develop novel virolytic agents, which could cause virus lysis and prevent viral infection even in the absence of cells. The present invention fulfills these needs.

BRIEF SUMMARY OF THE INVENTION

The invention provides a cyclic compound of formula (I), or a salt, solvate, enantiomer or diastereoisomer thereof. The invention further provides a pharmaceutical composition comprising at least one pharmaceutically acceptable carrier and at least one cyclic compound of the invention. The invention further provides a method of treating, reducing or preventing HIV-1 infection in a mammal in need thereof, the method comprising administering to the mammal a therapeutically effective amount of at least one cyclic compound of the invention. The invention further provides a method of reducing the risk of HIV-1 infection in a mammal at risk of HIV-1 exposure, the method comprising administering to the mammal a therapeutically effective amount of at least one cyclic compound of the invention. The invention further provides a method of promoting virolysis of a virus, the method comprising contacting the virus with an effective amount of at least one cyclic compound of the invention, wherein $P_1$ is not absent. The invention further provides a method of reducing the rate of or preventing entry of a virus into a cell of a mammal, the method comprising administering to the mammal a therapeutically effective amount of at least one cyclic compound of the invention. The invention further provides a method of preparing a derivatized gold nanoparticle, the method comprising contacting the nanoparticle with at least one cyclic compound of the invention to generate a reaction system; and isolating the derivatized gold nanoparticle from the reaction system.

In certain embodiments, the cyclic peptide is a compound of formula (I), $Xaa_1\text{-}Xaa_2\text{-}Xaa_3\text{-}Xaa_4\text{-}Xaa_5\text{-}Xaa_6\text{-}Xaa_7\text{-}Xaa_8\text{-}Xaa_9\text{-}P_1$ (I), wherein in (I): $Xaa_1$ is selected from the group consisting of absent, Glu and Arg; $Xaa_2$ is selected from the group consisting of absent, Gly, Phe, Lys, Asp, Glu, Ile, Arg and Cit; $Xaa_3$ is selected from the group consisting of absent, Asn, Asp, Ile, Glu, butanedioic acid (succinic acid), and 2-cyclohexylglycine; $Xaa_4$ is selected from

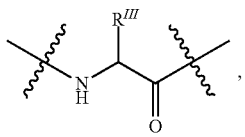

the group consisting of Asn and Asp; $Xaa_5$ is a modified glycine of formula (III) wherein $R^{III}$ is selected from the group consisting of $C_1\text{-}C_6$ alkyl and $C_3\text{-}C_6$ cycloalkyl; $Xaa_6$ is the modified proline of formula (IV)

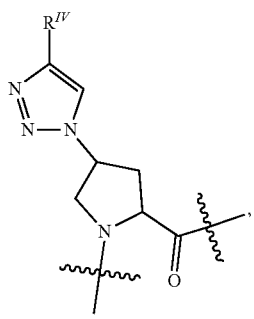

wherein in (IV): $R^{IV}$ is selected from the group consisting of: adamantyl substituted with 0-2 $C_1\text{-}C_6$ alkyl groups; —($C_0\text{-}C_4$ alkyl)phenyl, wherein the phenyl is substituted with 0-2 $C_1\text{-}C_6$ alkyl groups; phenyl substituted with $R^1$ and with 0-2 $C_1\text{-}C_6$ alkyl groups; and heteroaryl substituted with $R^1$ and with 0-2 $C_1\text{-}C_6$ alkyl groups; wherein each occurrence of $R^1$ is independently selected from the group consisting of phenyl substituted with 0-2 $C_1\text{-}C_6$ alkyl groups and heteroaryl substituted with 0-2 $C_1\text{-}C_6$ alkyl groups; and wherein each occurrence of heteroaryl is independently selected from the group consisting of pyridine, pyrimidine, thiophene, furan, pyrrole, imidazole, oxazole, oxadiazole, thiazole, thiadiazolyl, isothiazole, and tetrazole; $Xaa_7$ is selected from the group consisting of Trp and 3-(3-benzothienyl)-L-alanine; $Xaa_8$ is selected from the group consisting of Ser, Thr, 2,4-diaminobutanoic acid, Orn and Lys; $Xaa_9$ is selected from the group consisting of absent, 2,4-diaminobutanoic acid, Orn, Lys, Glu, Glu-Ala, Glu-Ala-Met, Glu-Ala-Met-Met, and 2-(2-(2-aminoethoxy) ethoxy) acetic acid; $P_1$ is absent, or is a group that comprises at least one thiol group and is covalently linked through an amide bond to (i) the C-terminus of $Xaa_9$ if $Xaa_9$ is not absent, or (ii) the C-terminus of $Xaa_8$ if $Xaa_9$ is absent; the side chain amino group of one residue selected from the group consisting of 2,4-diaminobutanoic acid at $Xaa_8$, Orn at $Xaa_8$, Lys at $Xaa_8$, 2,4-diaminobutanoic acid at $Xaa_9$, Orn at $Xaa_9$, and Lys at $Xaa_9$ forms an amide bond with the side chain carboxylic acid group of one residue selected from the group consisting of Glu at $Xaa_2$, Asp at $Xaa_2$, Glu at $Xaa_3$, Asp at $Xaa_3$, succinic acid at $Xaa_3$, and Asp at $Xaa_4$; and the C-terminus of $Xaa_8$ is optionally amidated if $Xaa_9$ and $P_1$ are absent, or the C-terminus of $Xaa_9$ is optionally amidated if $P_1$ is absent.

In certain embodiments, the cyclic compound is selected from the group consisting of:

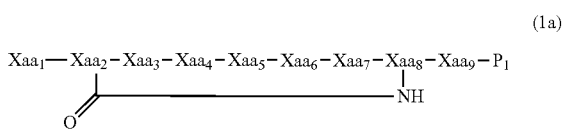

(Ia)

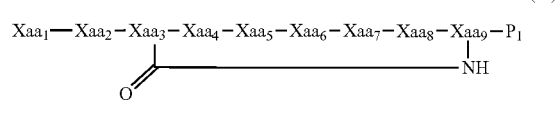

(Id)

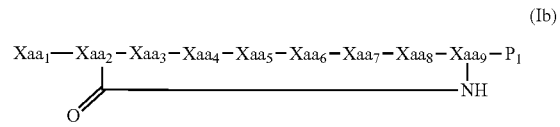

(Ib)

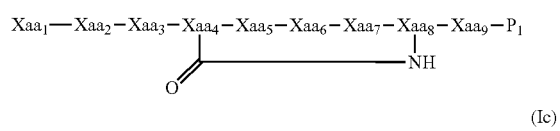

(Ie)

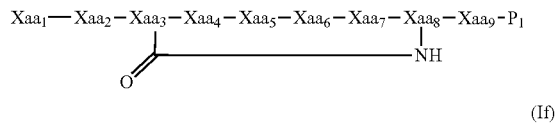

(Ic)

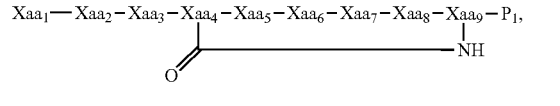

(If)

wherein in (Ia)-(If) 'NH' is derived from the side chain amino group of a residue selected from the group consisting of 2,4-diaminobutanoic acid at $Xaa_8$, Orn at $Xaa_8$, Lys at $Xaa_8$, 2,4-diaminobutanoic acid at $Xaa_9$, Orn at $Xaa_9$, and Lys at $Xaa_9$, and 'C—O' is derived from the side chain carboxylic acid group of a residue selected from the group consisting of Glu at $Xaa_2$, Asp at $Xaa_2$, Glu at $Xaa_3$, Asp at $Xaa_3$, succinic acid at $Xaa_3$, and Asp at $Xaa_4$.

In certain embodiments, the cyclic compound is the compound of formula (II): $Xaa_1\text{-}Xaa_2\text{-}Xaa_3\text{-}Xaa_4\text{-}Xaa_5\text{-}Xaa_6\text{-}Xaa_7\text{-}Xaa_8\text{-}Xaa_9\text{-}P_1$ (II), wherein in (II): $Xaa_1$ is selected from the group consisting of absent, Glu and Arg; $Xaa_2$ is selected from the group consisting of absent, Gly, Phe, Lys, Asp, Glu, Ile, Arg and Cit; $Xaa_3$ is selected from the group consisting of Asn, Asp, succinic acid, and Glu; $Xaa_4$ is Asn; $Xaa_8$ is Ile; $Xaa_6$ is the modified proline of formula (IV)

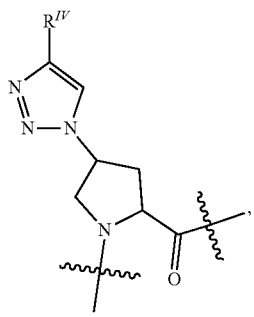

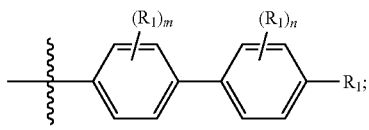

and

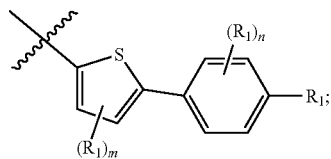

wherein each occurrence of $R_1$ is independently $C_1$-$C_6$ alkyl; m is 0, 1, or 2; and n is 0 or 1.

In certain embodiments, $P_1$ is not absent. In other embodiments, $P_1$ comprises at least one cysteine residue. In yet other embodiments, $P_1$ is selected from the group consisting of βAla Gln βAla Cys-NH$_2$ (SEQ ID NO:4) βAla Gln βAla Cys (SEQ ID NO:5),

NH$_2$(CH$_2$CH$_2$O)$_{0-10}$CH$_2$C(═O)NHCH(CH$_2$SH)C(═O) OH,

NH$_2$(CH$_2$CH$_2$O)$_{0-10}$CH$_2$C(═O)NHCH(CH$_2$SH)C(═O) NH$_2$,

NH$_2$(CH$_2$)$_{0-12}$CH$_2$C(═O)NHCH(CH$_2$SH)C(═O)OH,

NH$_2$(CH$_2$)$_{0-12}$CH$_2$C(═O)NHCH(CH$_2$SH)C(═O)NH$_2$, and

NH$_2$CH$_2$CH$_2$OCH$_2$CH$_2$OC(═O)NHCH(CH$_2$SH)C (═O)NH$_2$.

In certain embodiments, the cyclic peptide is selected from the group consisting of:

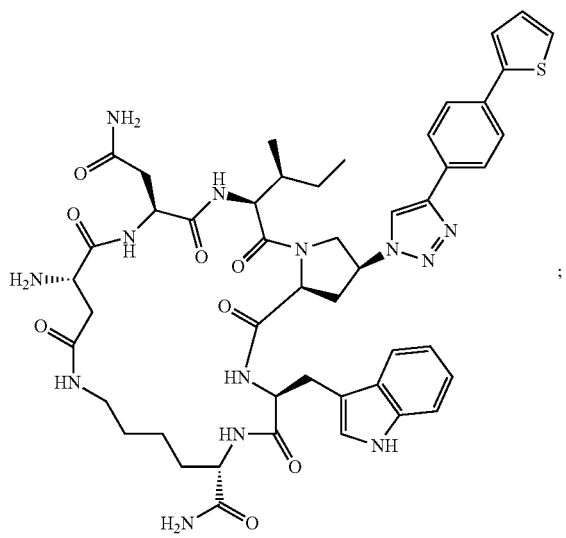

wherein: $R^{IV}$ is selected from the group consisting of: adamantyl substituted with 0-2 $C_1$-$C_6$ alkyl groups; —(C$_0$-C$_4$ alkyl)phenyl, wherein the phenyl is substituted with 0-2 $C_1$-$C_6$ alkyl groups; phenyl substituted with $R^1$ and with 0-2 $C_1$-$C_6$ alkyl groups; and heteroaryl substituted with $R^1$ and with 0-2 $C_1$-$C_6$ alkyl groups; wherein each occurrence of $R^1$ is independently selected from the group consisting of phenyl substituted with 0-2 $C_1$-$C_6$ alkyl groups and heteroaryl substituted with 0-2 $C_1$-$C_6$ alkyl groups; and wherein each occurrence of heteroaryl is independently selected from the group consisting of pyridine, pyrimidine, thiophene, furan, pyrrole, imidazole, oxazole, oxadiazole, thiazole, thiadiazolyl, isothiazole, and tetrazole; Xaa$_7$ is Trp; Xaa$_8$ is selected from the group consisting of Ser, Thr, 2,4-diaminobutanoic acid, Orn and Lys; Xaa$_9$ is selected from the group consisting of absent, 2,4-diaminobutanoic acid, Orn, Lys, Glu, Glu-Ala, Glu-Ala-Met, Glu-Ala-Met-Met, and 2-(2-(2-aminoethoxy) ethoxy) acetic acid; $P_1$ is absent, or is a group that comprises at least one thiol group and is covalently linked through an amide bond to (i) the C-terminus of Xaa$_9$ if Xaa$_9$ is not absent or (ii) the C-terminus of Xaa$_8$ if Xaa$_9$ is absent; the side chain amino group of one residue selected from the group consisting of 2,4-diaminobutanoic acid at Xaa$_8$, Orn at Xaa$_8$, Lys at Xaa$_8$, 2,4-diaminobutanoic acid at Xaa$_9$, Orn at Xaa$_9$, and Lys at Xaa$_9$ forms an amide bond with the side chain carboxylic acid group of one residue selected from the group consisting of Glu at Xaa$_2$, Asp at Xaa$_2$, Glu at Xaa$_3$, succinic acid at Xaa$_3$, and Asp at Xaa$_3$; and the C-terminus of Xaa$_8$ is optionally amidated if Xaa$_9$ and $P_1$ are absent, or the C-terminus of Xaa$_9$ is optionally amidated if $P_1$ is absent.

In certain embodiments, Xaa$_8$ is selected from the group consisting of Ile, Leu, norleucine (Nle), cyclopropylglycine, cyclobutylglycine, cyclopentylglycine, and cyclohexylglycine.

In certain embodiments, $R^{III}$ is a secondary or tertiary hydrocarbyl group. In other embodiments, $R^{III}$ is selected from the group consisting of cyclohexyl, —CH(CH$_3$)(C$_1$-C$_4$ alkyl), and —C(CH$_3$)$_2$ (C$_1$-C$_3$ alkyl).

In certain embodiments, the C-terminus of Xaa$_8$ is not amidated if Xaa$_9$ and $P_1$ are absent. In other embodiments, the C-terminus of Xaa$_9$ is not amidated if $P_1$ is absent. In yet other embodiments, the C-terminus of Xaa$_8$ is amidated if Xaa$_9$ and $P_1$ are absent. In yet other embodiments, the C-terminus of Xaa$_9$ is amidated if $P_1$ is absent. In yet other embodiments, if the carbon alpha to the carboxyl group of Xaa$_8$ is chiral, the stereochemistry of the alpha carbon is S. In yet other embodiments, the heteroaryl is thiophene.

In certain embodiments, $R^{IV}$ is selected from the group consisting of: —(C$_0$-C$_4$ alkyl)phenyl, wherein the phenyl is substituted with 1-2 $C_1$-$C_6$ alkyl groups, wherein one of the $C_1$-$C_6$ alkyl groups is at the para position of the phenyl group;

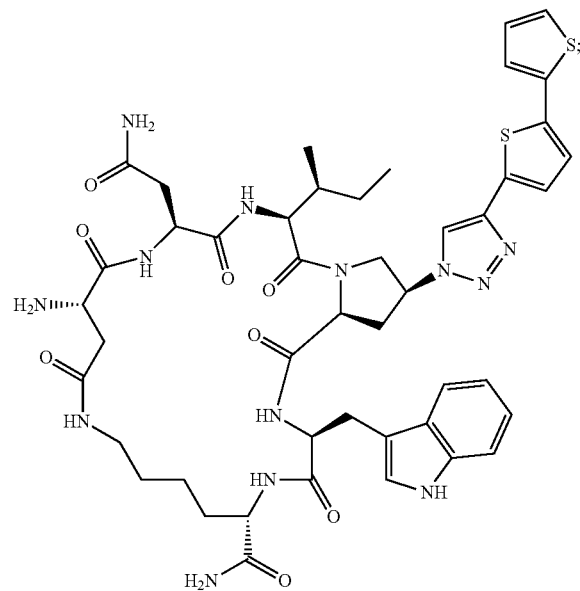
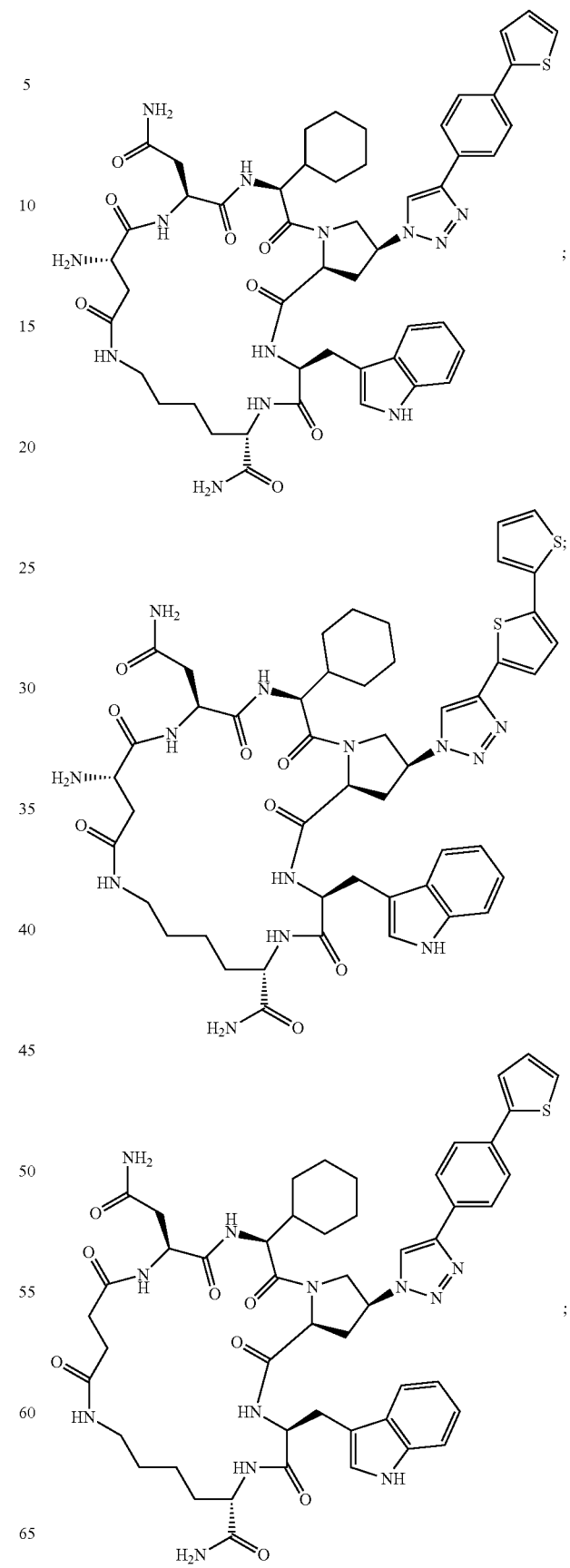

9
-continued
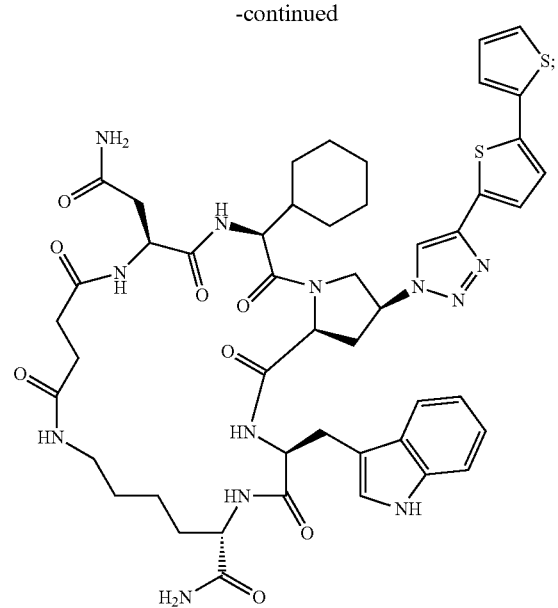
10
-continued
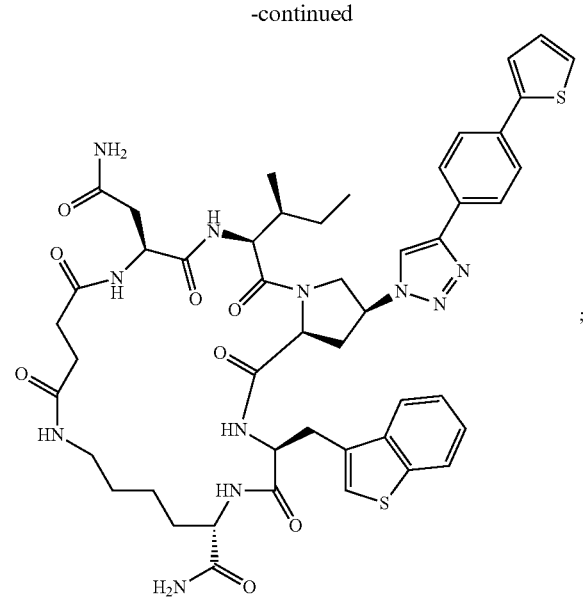
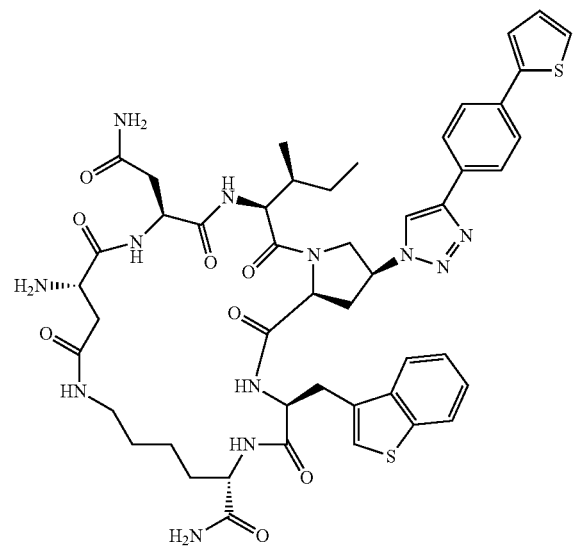
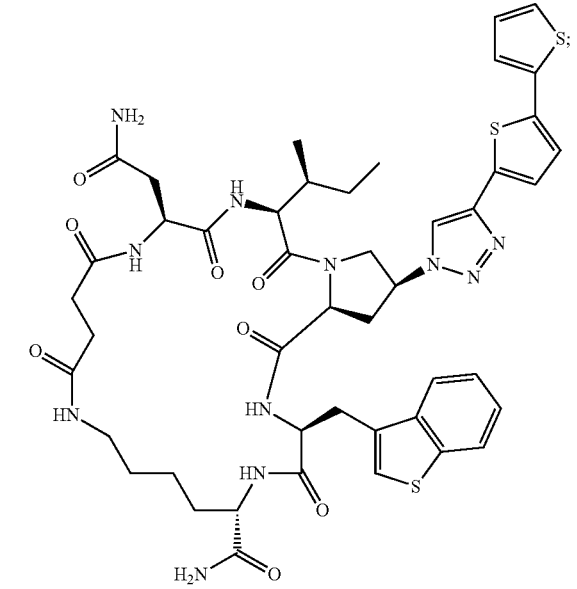
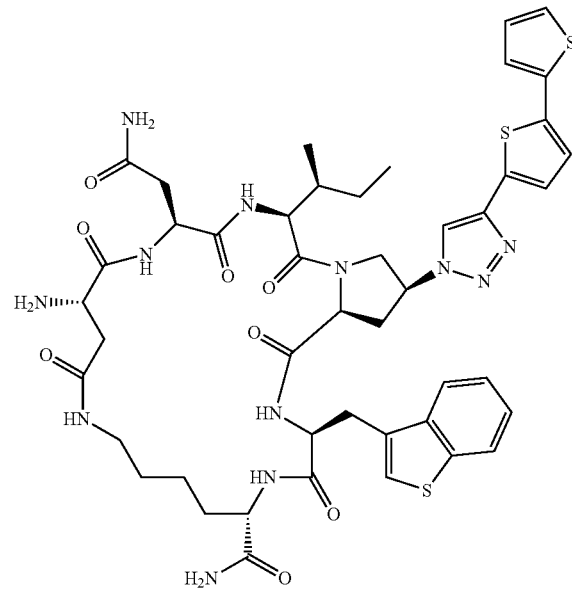
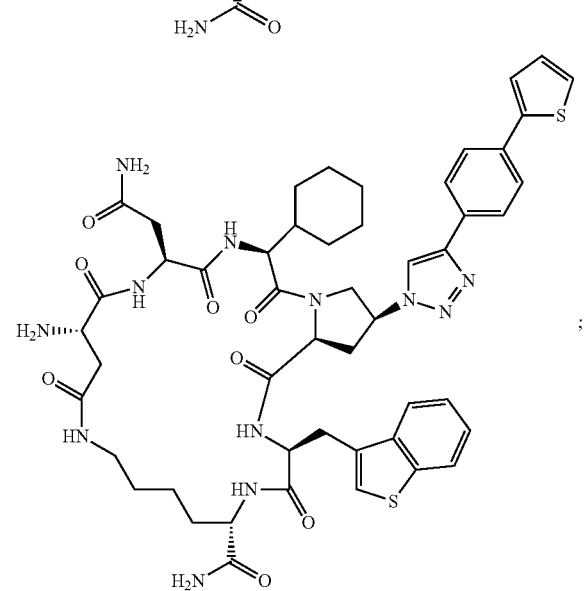

11
-continued
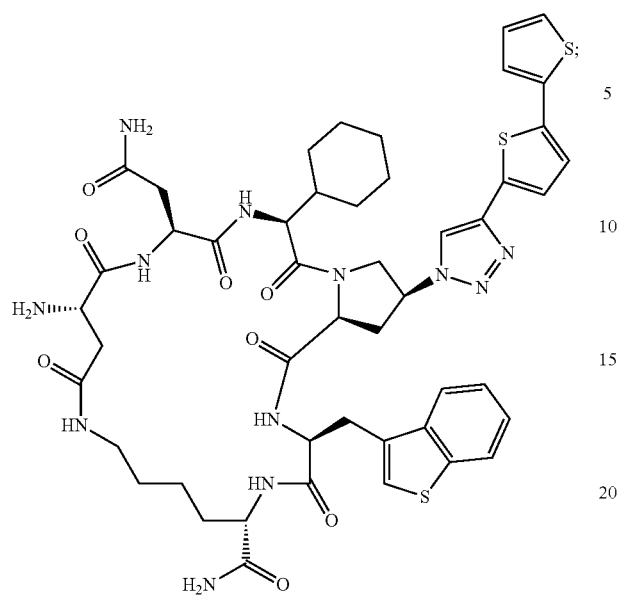
12
-continued
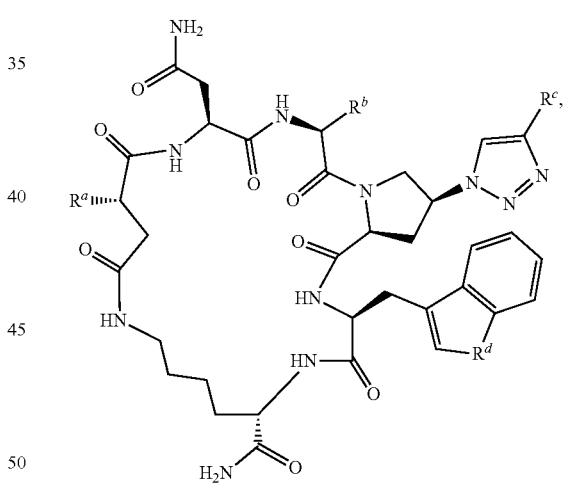
or a salt or solvate thereof.
In certain embodiments, the cyclic peptide is a compound of formula (V):
(V)
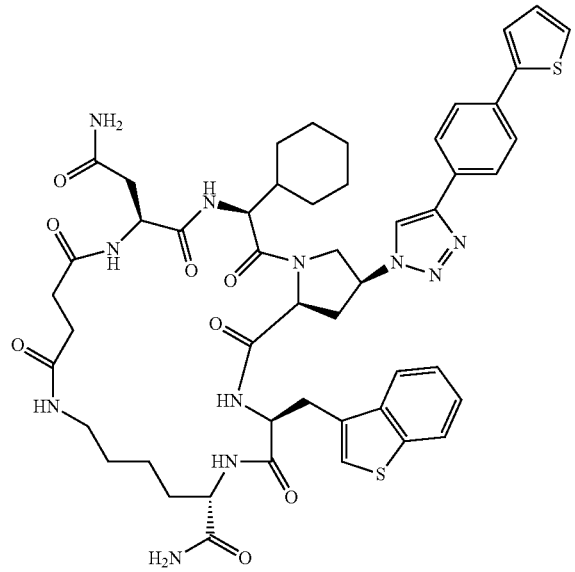
wherein: $R^a$ is $NH_2$ or H; $R^b$ is cyclohexyl or sec-butyl; $R^c$ is selected from the group consisting of:
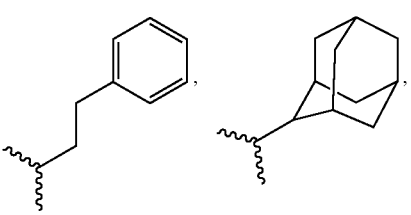

$R^d$ is NH or S; or a salt or solvate thereof.

In certain embodiments, $P_1$ is not absent and (I) is complexed through the at least one thiol group with at least one gold nanoparticle. In other embodiments, the at least one nanoparticle has an average diameter of about 20 nm.

In certain embodiments, the composition of the invention further comprises at least one additional compound useful for treating viral infections. In other embodiments, the at least one additional compound is selected from the group consisting of antiviral combination drugs, entry and fusion inhibitors, integrase inhibitors, non-nucleoside reverse transcriptase inhibitors, nucleoside reverse transcriptase inhibitors, protease inhibitors, and any combinations thereof.

In certain embodiments, the cyclic peptide is encapsulated in a hydrogel and/or liposome.

In certain embodiments, the mammal is further administered at least one additional compound useful for treating viral infections. In other embodiments, the mammal is human. In yet other embodiments, the virus comprises HIV-1.

BRIEF DESCRIPTION OF THE DRAWINGS

For the purpose of illustrating the invention, certain embodiments of the invention are depicted in the drawings. However, the invention is not limited to the precise arrangements and instrumentalities of the embodiments depicted in the drawings.

FIG. 8C: infection inhibition curves against HIV-$1_{Bal.01}$ for 36 & 37; FIG. 8D: cell viability assay for 36 & 37. SPR competition assay were used to determine the ability of 36 to inhibit gp120 binding to both 17b (FIG. 8E) and CD4 (FIG. 8F).

DETAILED DESCRIPTION OF THE INVENTION

The present invention relates in one aspect to the discovery of novel gp120-targeting cyclic peptide antagonists that inhibit both CD4 and co-receptor binding sites. In certain embodiments, the thiophene-containing cyclic peptide antagonists of the invention showed enhanced binding to Env gp120 and improved antiviral activity compared to the ferrocene-containing analogues. The invention also relates in another aspect to compositions comprising gold nanoparticles conjugated to the cyclic peptides of the invention, wherein the cyclic peptides comprise a thiol group.

Figure 1:
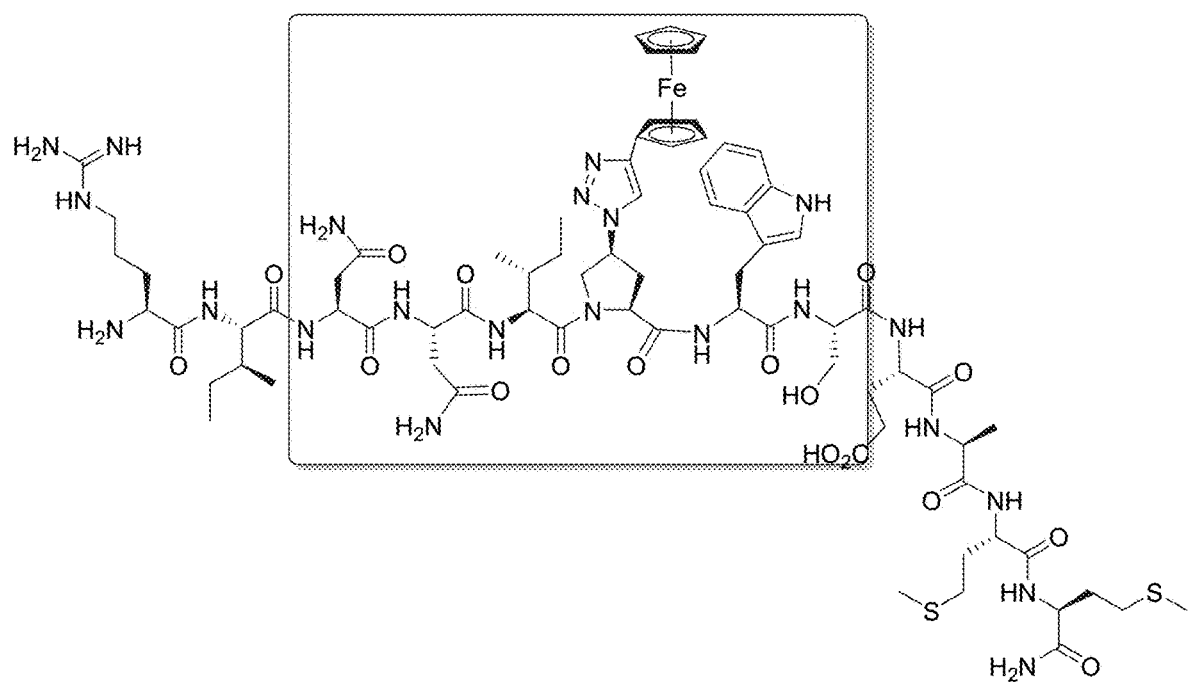
FIG. 1 comprises a schematic illustration of HNG156 (Arg Ile Asn Asn Ile X Trp Ser Glu Ala Met Met-$NH_2$; SEQ ID NO:1), wherein X is a modified proline.
Figure 2:
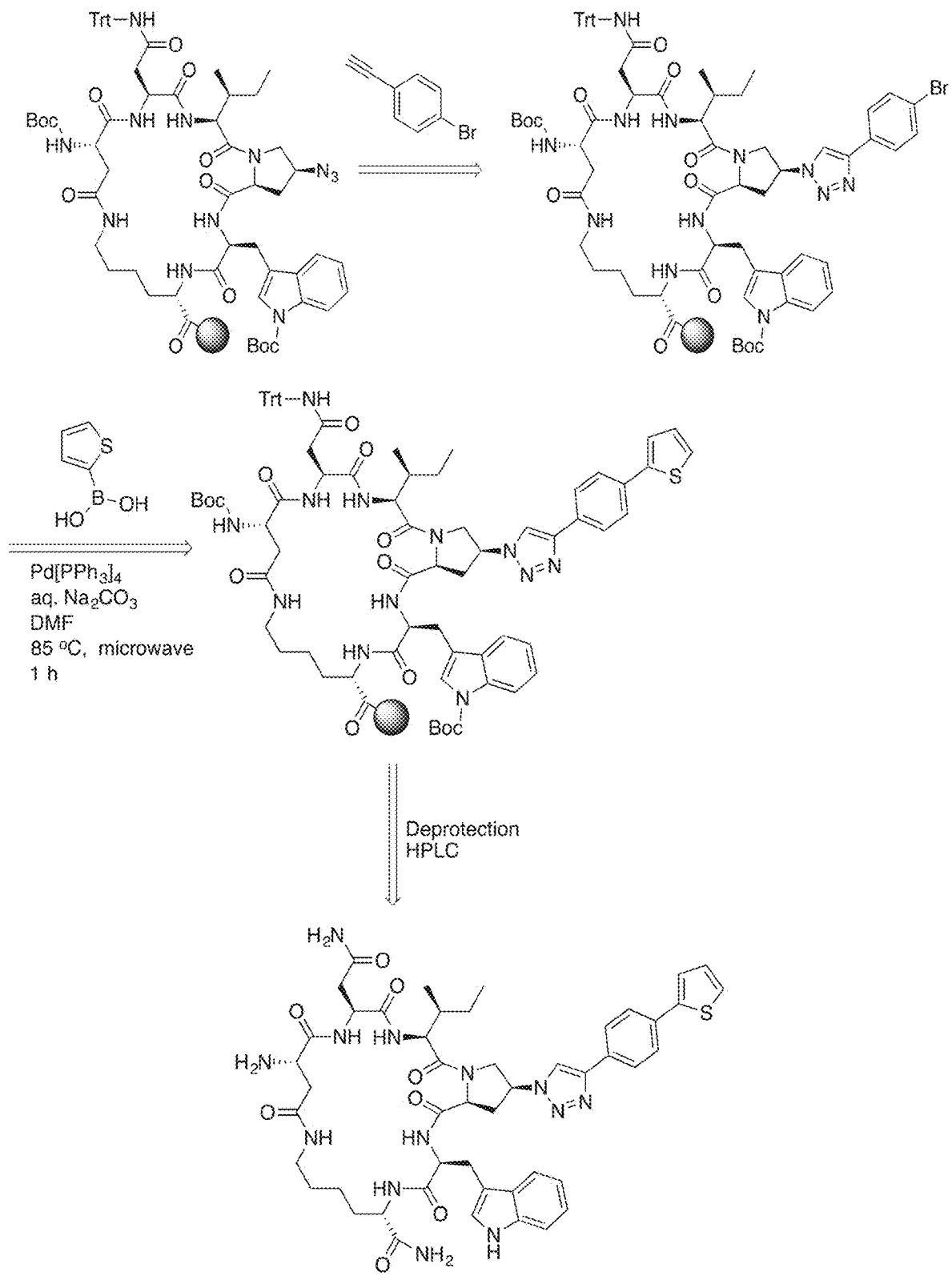
FIG. 2 comprises an illustrative synthetic scheme for a non-limiting cyclic peptide of the invention (Compound 29N-2).
Figure 3:
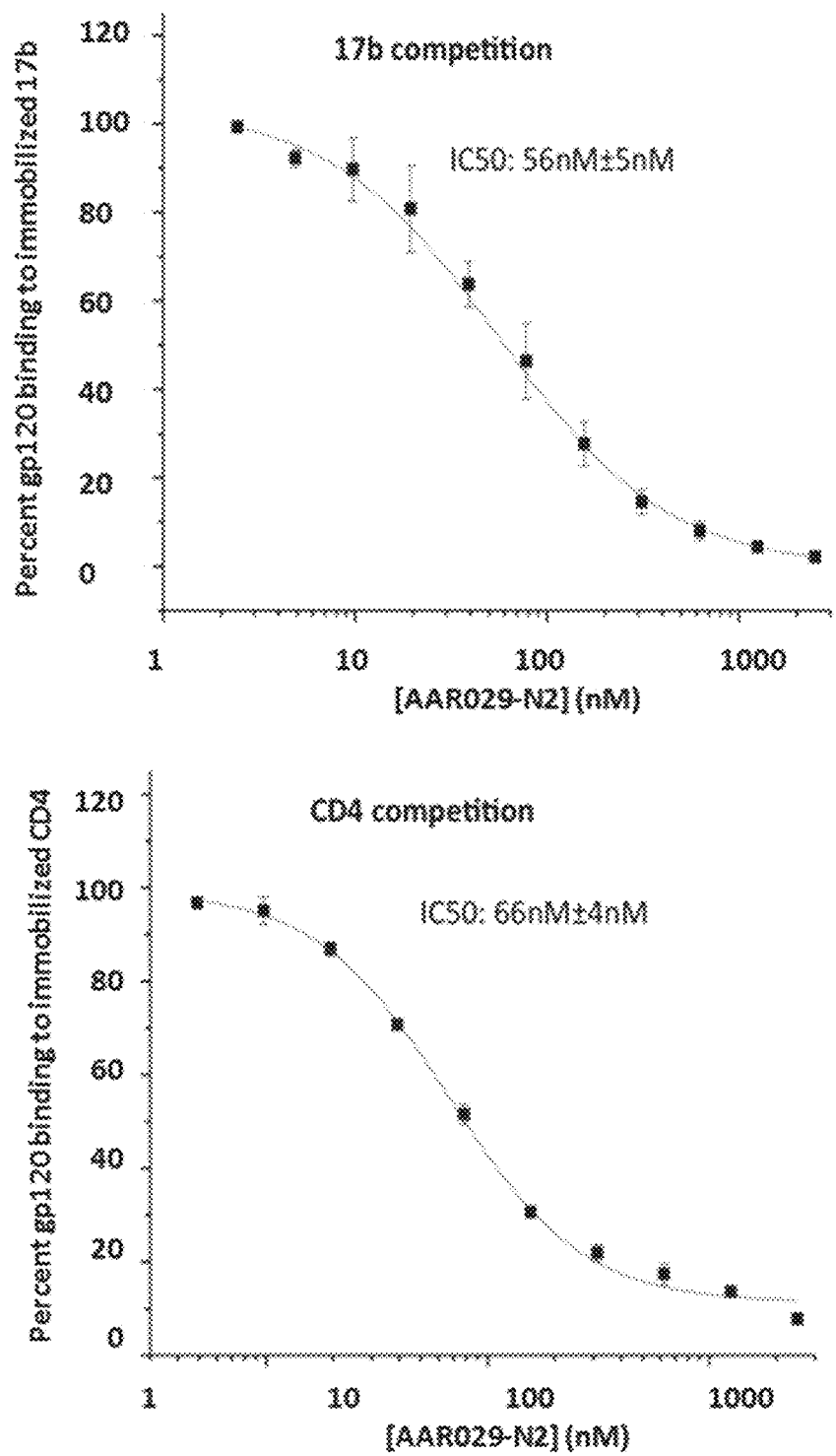
FIG. 3 comprises a set of graphs illustrating inhibition of binding of gp120 to CD4 or 17b by a non-limiting cyclic peptide of the invention (Compound 29N-2). CD4 inhibition, $IC_{50}$~66 nM; 17b inhibition, $IC_{50}$~56 nM; HIV-1, $IC_{50}$~105 nM.
Figure 4:
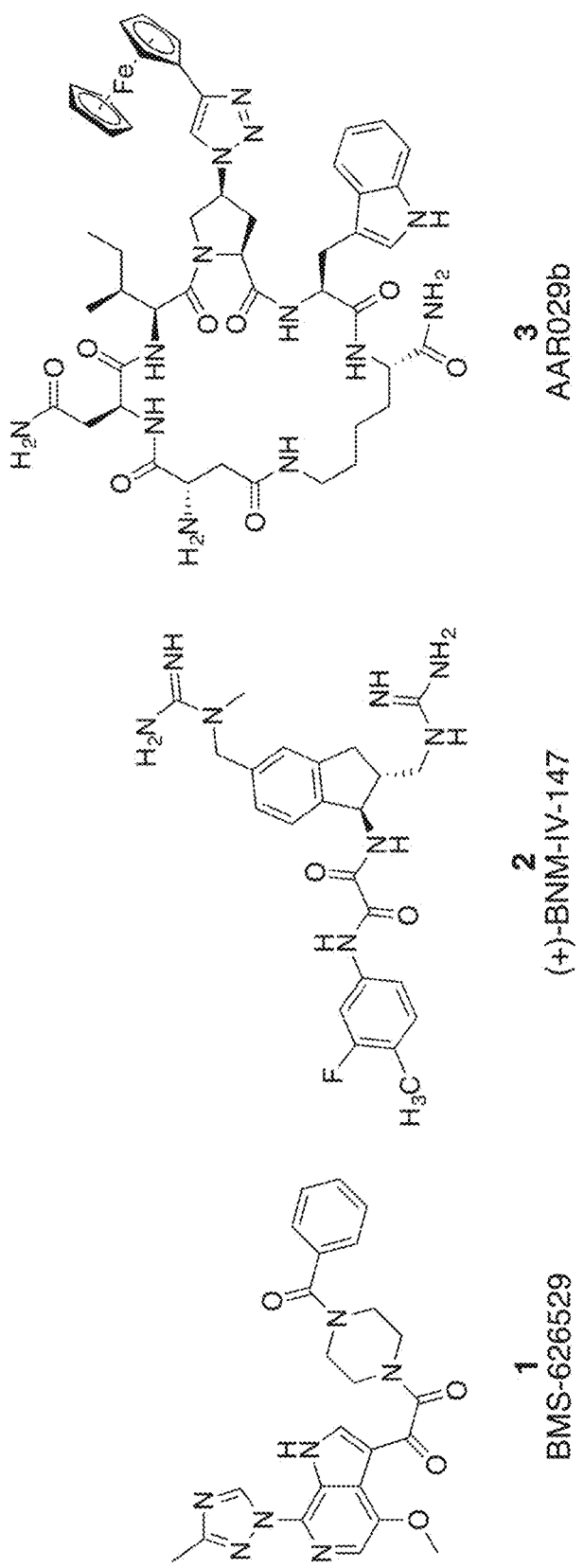
FIG. 4 illustrates chemical structures of small molecule and small macrocyclic gp120 targeting inhibitors. Shown are the conformational blocker attachment inhibitor BMS-626529 (1), small molecule CD4 mimetic (+)-BNM-IV-147 (2) and the conformational entrapping HIV-1 inactivator cPT AAR029b (3).

A class of small cyclic peptide triazoles (cPTs, represented by the first lead AAR029b, 3, FIG. 4) irreversibly inactivates HIV-1 virions, even before host cell encounter. They exert this unique mode of inactivation by hijacking the metastability of the Env protein complex, converting the gp120 into an inactive conformation that leads to gp120 shedding off the Env from the virion surface. The resultant gp41 coated virions become non-infectious. Interestingly, the binding site of cPTs seems to overlap both binding sites of BMS-626529 (FIG. 4) and the CD4 small molecule mimetics.

The present disclosure comprises chemical explorations around the scaffold of cPT, at least in part to better understand the structural requirements for function and to identify new methodologies to derive cPT compounds with an increased capacity for structural variation. As demonstrated herein, variations in many cPT structural elements were tolerated, though only within a narrow range of possibilities. In contrast, significant variations were tolerated in the substituted triazole component, leading to chemical space expansion, improved potency and molecular-structural properties.

Definitions

As used herein, each of the following terms has the meaning associated with it in this section.

Unless defined otherwise, all technical and scientific terms used herein generally have the same meaning as commonly understood by one of ordinary skill in the art to which this invention belongs. Generally, the nomenclature used herein and the laboratory procedures in cell culture, molecular genetics, peptide chemistry, and organic chemistry are those well-known and commonly employed in the art.

The following abbreviations were used herein: ACN, acetonitrile; βAla or bAla, beta-alanine or 3-aminopropionic acid; Boc, Tertbutyloxycarbonyl; CM5, carboxymethyl dextran; cPT, cyclic peptide triazole; Dab or Dbu, 2-diaminobutyric acid; DCM, dichloromethane; Dde, protective group 1-(4,4-Dimethyl-2,6-dioxocyclohex-1-ylidene)ethyl; DIC, N,N'-Diisopropylcarbodiimide; DIPEA, N,N-diisopropylethylamine; Dmab, protective group 4-(N-[1(4,4-Dimethyl-2,6-dioxocyclohexylidene)-3-methylbutyl]amino)benzyl ester; DMF, Dimethylformamide; EDC, 1-ethyl-3-(3-dimethylaminopropyl)carbodiimide; Env, HIV envelope gp160; ESI-MS, Electro-spray ionization mass spectrometry; Fmoc, 9-Fluorenylmethoxycarbonyl; HBTU, O-benzotriazole-N,N,N',N'-tetramethyl-uronium-hexafluoro-phosphate; HEK, Human embryonic kidney; HOBt, 1-hydroxybenzotriazole; HPLC, High performance liquid chromatography; IXW, Ile-ferrocenyltriazolePro-Trp; NHS, N-hydroxysuccinimide; Nle, norleucine or (2S)-2-aminohexanoic acid; NP, nanoparticle; Orn, ornithine or 2,5-diaminopentanoic acid; Oxyma, ethyl cyano (hydroxyimino)acetate; PBS, phosphate buffered saline; PT, Peptide triazole; SAR, Structure Activity Relationship; SDS-page, sodium dodecyl sulfate-polyacrylamide gel electrophoresis; SI, selectivity index; SPR, surface plasmon resonance; tBu, tert-butyl; TIPS, Triisoproylsilane; TFA, Trifluoroacetic acid; Trt, Triphenylmethyl; wt, wild type.

As used herein, the articles "a" and "an" refer to one or to more than one (i.e., to at least one) of the grammatical object of the article. By way of example, "an element" means one element or more than one element.

As used herein, the term "about" is understood by persons of ordinary skill in the art and varies to some extent on the context in which it is used. As used herein when referring to a measurable value such as an amount, a temporal duration and the like, the term "about" is meant to encompass variations of ±20%, more preferably ±10%, more preferably ±5%, even more preferably ±1%, and still more preferably ±0.1% from the specified value, as such variations are appropriate to perform the disclosed methods.

As used herein, the term "antiviral agent" means a composition of matter that, when delivered to a cell, is capable of preventing replication of a virus in the cell, preventing infection of the cell by a virus, or reversing a physiological effect of infection of the cell by a virus. Antiviral agents are well known and described in the literature. By way of example, AZT (zidovudine, RETROVIR®, Glaxosmithkline, Middlesex, UK) is an antiviral agent that is thought to prevent replication of HIV in human cells.

"Applicator," as the term is used herein, is used to identify any device including, but not limited to, a hypodermic syringe, a pipette, and the like, for administering the compounds and compositions used in the practice of the invention.

As used herein with respect to the compounds of the invention, "biologically active" means that the compounds elicit a biological response in a mammal that can be monitored and characterized in comparison with an untreated mammal. One possible biological response within the invention relates to the ability of the compound to avoid, reduce or treat HIV-1 infection in a mammal. In this particular case, the compound is administered to the mammal by an administration route selected from the group consisting of nasal, inhalational, topical, oral, buccal, rectal, pleural, peritoneal, vaginal, intramuscular, subcutaneous, transdermal, epidural, intratracheal, otic, intraocular, intrathecal and intravenous. The mammal and the HIV-1 viral load level in its body are monitored as a function of time, and the observation of a measurable and dose-dependent change in HIV-1 infection rate or viral load in the body is evidence that the compound displays biological activity. This preferred biological response does not limit or restrict the disclosures or embodiments of the invention in any way.

As used herein, the term "container" includes any receptacle for holding the compounds and/or compositions of the invention. For example, in certain embodiments, the container is the packaging that contains the compounds and/or compositions of the invention. In other embodiments, the container is not the packaging that contains the compounds and/or compositions of the invention, i.e., the container is a receptacle, such as a box or vial that contains the compounds and/or compositions of the invention or unpackaged compounds and/or compositions of the invention and the instructions for use of the compounds and/or compositions of the invention. Moreover, packaging techniques are well known in the art. It should be understood that the instructions for use of the compounds and/or compositions of the invention may be contained on the packaging containing the compounds and/or compositions of the invention, and as such the instructions form an increased functional relationship to the packaged product. However, it should be understood that the instructions can contain information pertaining to the compound's ability to perform its intended function, e.g., treating, ameliorating, or preventing HIV-1 infection in a subject.

As used herein, the term "gp120 binder" refers to a small molecule, peptide or antibody that binds to the envelope protein gp120 of HIV-1.

As used herein, the term "heteroaryl" or "heteroaromatic" refers to a heterocycle having aromatic character. A polycyclic heteroaryl may include one or more rings that are partially saturated. Examples include tetrahydroquinoline and 2,3-dihydrobenzofuryl. Examples of heteroaryl groups include pyridyl, pyrazinyl, pyrimidinyl (such as, but not limited to, 2- and 4-pyrimidinyl), pyridazinyl, thienyl, furyl, pyrrolyl, imidazolyl, thiazolyl, oxazolyl, pyrazolyl, isothiazolyl, 1,2,3-triazolyl, 1,2,4-triazolyl, 1,3,4-triazolyl, tetrazolyl, 1,2,3-thiadiazolyl, 1,2,3-oxadiazolyl, 1,3,4-thiadiazolyl and 1,3,4-oxadiazolyl.

As used herein, the term "medical intervention" means a set of one or more medical procedures or treatments that are required for ameliorating the effects of, delaying, halting or reversing a disease or disorder of a subject. A medical intervention may involve surgical procedures or not, depending on the disease or disorder in question. A medical intervention may be wholly or partially performed by a medical specialist, or may be wholly or partially performed by the subject himself or herself, if capable, under the supervision of a medical specialist or according to literature or protocols provided by the medical specialist.

As used herein, "natural amino acids" are represented by the full name thereof, by the three-letter code, as well as the one-letter code corresponding thereto, as known to those skilled in the art.

As used herein, the term "non-natural amino acid" corresponds to an amino acid that is not the L-isomer of one of the natural alpha-amino acids listed herein. Non-natural amino acids include, but are not limited to, the D-isomer of a natural amino acid, $H_2N(CH_2CH_2O)_nCH_2CH_2COOH$ (wherein MW varies from ~1000 Da to 10000 Da), $H_2N(CH_2)_nCOOH$ (wherein n is an integer that varies from 3 to 8), arginosuccinic acid, citrulline, cysteine sulfinic acid, 3,4-dihydroxy-phenylalanine, homocysteine, homoserine, ornithine, hydroxylysine, 4-hydroxy-proline, an N-Cbz-protected amino acid, 2,4-diaminobutyric acid, homoarginine, N-methyl-arginine, norleucine, N-methylaminobutyric acid, naphthylalanine, phenylglycine, beta-phenylproline, tert-leucine, 4-aminocyclohexyl-alanine, N-methyl-norleucine, 3,4-dehydroproline, N,N-dimethylaminoglycine, N-methylaminoglycine, 4-aminopiperidine-4-carboxylic acid, 6-aminocaproic acid (also known as Acp or 6-aminohexanoic acid), 6-aminocapramide (also known as $AcpNH_2$ or 6-aminohexanamide), beta-alanine (also known as bAla or βAla), $bAlaNH_2$ (or βAlaNH2, and also known as 3-aminopropanamide), trans-4-(aminomethyl)-cyclohexanecarboxylic acid, 2-(aminomethyl)-benzoic acid, 3-(aminomethyl)-benzoic acid, 4-(aminomethyl)-benzoic acid, 1-aminocyclopentanecarboxylic acid, 1-aminocyclopropanecarboxylic acid, and 2-benzyl-5-aminopentanoic acid. Preferentially, the non-natural amino acid is selected from the group consisting of Acp, $AcpNH_2$, bAla and $bAlaNH_2$.

As used herein, the terms "peptide," "polypeptide," or "protein" are used interchangeably, and refer to a compound comprised of amino acid residues covalently linked by peptide bonds. A protein or peptide must contain at least two amino acids, and no limitation is placed on the maximum number of amino acids that can comprise the sequence of a protein or peptide. Polypeptides include any peptide or protein comprising two or more amino acids joined to each other by peptide bonds. As used herein, the term refers to both short chains, which also commonly are referred to in the art as peptides, oligopeptides and oligomers, for example, and to longer chains, which generally are referred to in the art as proteins, of which there are many types. "Polypeptides" include, for example, biologically active fragments, substantially homologous polypeptides, oligopeptides, homodimers, heterodimers, variants of polypeptides, modified polypeptides, derivatives, analogs and fusion proteins, among others. The polypeptides include natural peptides, recombinant peptides, synthetic peptides or a combination thereof. A peptide that is not cyclic has a N-terminus and a C-terminus. The N-terminus has an amino group, which may be free (i.e., as a $NH_2$ group) or appropriately protected (e.g., with a BOC or a Fmoc group). The C-terminus has a carboxylic group, which may be free (i.e., as a COOH group) or appropriately protected (e.g., as a benzyl or a methyl ester). A cyclic peptide does not necessarily have free N- or C-termini, since they are covalently bonded through an amide bond to form the cyclic structure.

As used herein, a "pharmaceutically acceptable carrier" means a pharmaceutically acceptable material, composition or carrier, such as a liquid or solid filler, diluent, excipient, solvent or encapsulating material, involved in carrying or transporting a compound(s) of the present invention within or to the subject such that it may perform its intended function. Typically, such compounds are carried or transported from one organ, or portion of the body, to another organ, or portion of the body. Each carrier must be "acceptable" in the sense of being compatible with the other ingredients of the formulation, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; gar; buffering agents, such as magnesium hydroxide and aluminum hydroxide; alginic acid; pyrogen-free water; isotonic saline; Ringer's solution; ethyl alcohol; phosphate buffer solutions; diluent; granulating agent; lubricant; binder; disintegrating agent; wetting agent; emulsifier; coloring agent; release agent; coating agent; sweetening agent; flavoring agent; perfuming agent; preservative; antioxidant; plasticizer; gelling agent; thickener; hardener; setting agent; suspending agent; surfactant; humectant; carrier; stabilizer; and other non-toxic compatible substances employed in pharmaceutical formulations, or any combination thereof. As used herein, "pharmaceutically acceptable carrier" also includes any and all coatings, antibacterial and antifungal agents, and absorption delaying agents, and the like that are compatible with the activity of the compound, and are physiologically acceptable to the subject. Supplementary active compounds may also be incorporated into the compositions.

As used herein, a "prophylactic" or "preventive" treatment is a treatment administered to a subject who does not exhibit signs of a disease or disorder or exhibits only early signs of the disease or disorder for the purpose of decreasing the risk of developing pathology associated with the disease or disorder.

As used herein, a "subject" or a "mammal" includes a human or a non-human mammal. Non-human mammals include, for example, livestock and pets, such as ovine, bovine, porcine, canine, feline and murine mammals. Preferably, the subject or mammal is human.

As used herein, a "therapeutic" treatment is a treatment administered to a subject who exhibits signs of pathology of a disease or disorder for the purpose of diminishing or eliminating those signs.

As used herein, the language "therapeutically effective amount" or "effective amount" refers to a non-toxic but sufficient amount of the composition used in the practice of the invention that is effective to treat, prevent or ameliorate HIV-1 infection in the body of a mammal. The desired treatment may be prophylactic and/or therapeutic. That result may be reduction and/or alleviation of the signs, symptoms, or causes of a disease or disorder, or any other desired alteration of a biological system. An appropriate therapeutic amount in any individual case may be determined by one of ordinary skill in the art using routine experimentation.

As used herein, the term "treating" means ameliorating the effects of, or delaying, halting or reversing the progress of a disease or disorder. The word encompasses reducing the severity of a symptom of a disease or disorder and/or the frequency of a symptom of a disease or disorder.

As used herein, the term "viral envelope protein binder" refers to a small molecule, peptide or antibody that binds to at least one envelope protein of a virus.

Throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 5 2.7, 3, 4, 5, 5.1, 5.3, 5.5, and 6. This applies regardless of the breadth of the range.

DESCRIPTION

The invention relates to a novel class of gp120-targeting cyclic peptide antagonists that inhibit both CD4 and co-receptor binding sites. The invention further relates to novel compositions comprising gold nanoparticles conjugated to the cyclic peptides of the invention, wherein the cyclic peptides comprise a thiol group. The present application incorporates herein by reference the entire teachings of International Application Publication No. WO 2016/094518. In certain embodiments, the cyclic peptides of the invention are more stable chemically, biologically and/or metabolically than the corresponding acyclic peptides.

The present invention discloses a SAR investigation of the chemical space around the cPT scaffold in order to identify paths for chemical and potency optimization. This was achieved by examining the effects of chemical variations in different parts of the cPT scaffold, including the pharmacophore Ile-X-Trp (where X is the aryl-triazolo-Pro) and the other half of the molecule (the cyclization bridge). Within the pharmacophore Ile-X-Trp, the aryl moiety on the triazole can act as an activity tuner, whereas the SAR around the Ile and Trp side chains was more limited and changes were less permissible.

A non-limiting finding in this work was the successful replacement of the less drug-like ferrocene moiety (on the triazole ring) with other moieties that retained similar activities. The bulky ferrocene moiety on the triazole ring had been found, after a series of optimizations, to provide good activity. Here, new triazole substituent moieties that had not been previously explored were evaluated, and hits that can allow further chemical optimization were identified.

Installing a long planer arm on the triazole ring that contains aromatic electron system(s) was found to, not only preserve the activity previously observed with the bulky ferrocene moiety, but also tune the activity to improve potency and obtain more drug-like cPTs. A promising system found in this work was the bi-aryl system, such as but not limited to a biphenyl moiety. One non-limiting advantage of cPTs as an emerging class of HIV-1 inhibitors is the facile short solid phase mediated synthesis, an important feature in inhibitor development. An on-resin method was thus developed to install different bi-aryl systems on the triazole ring, keeping the case of synthesis unchanged.

Since newly discovered triazole substituent components come from synthetic building blocks, rather than the amino acids, it can also be helpful to tune the physiochemical properties of the molecule. One example was replacing the terminal phenyl ring in cPT 23 with a thiophene isostere, in cPT 36, which resulted in improved anti-HIV potency.

In the current work, the other half of the cPT scaffold, the cyclization bridge, was also found to greatly affect the anti-HIV activity. Without wishing to be limited by any theory, this could occur not through the direct effect of losing or gaining contacts with the target gp120 protein by this part of the molecule, but rather through correctly/incorrectly directing the pharmacophore Ile-X-Trp within the active binding site on gp120. In certain non-limiting embodiments, this part of the scaffold can be referred to as a "conformational tuner". Varying the length of this cyclization bridge has impact on activities, as demonstrated by changes in activities observed in response to changes in the cyclization bridge. Changing the chirality of $CPT_{Asp}$ residue from the S to R configuration was more tolerated (7-fold change) than the same change in the $cPT_{Lys}$ residue. Without wishing to be limited by any theory, this could be explained by the proximity of the $cPT_{Lys}$ residue to the pharmacophore-Trp, whereas the cPT Asp residue is one-residue apart from the pharmacophore-Ile. In certain non-limiting embodiments, conformational changes at the cPT Asp residue can be more easily overcome than those caused by $CPT_{Lys}$ residue disruption. Complete removal of the chiral center at the $cPT_{Asp}$ residue resulted in comparable 8-fold decrease in activity observed with the S to R conversion. As for the N terminal $NH_3^+$ group, removing the chirality by removing that group had the same conformational disturbance as did the S to R conversion.

Generally, macrocyclic drugs, both naturally derived and synthetic, have received increasing attention in the past years owing to their excellent ability to target poor druggable targets such as PPIs. Macrocycles possess good pharmaceutical properties despite their relatively larger molecular weights compared to the conventional small molecule drugs. The evolving cPT inhibitors of HIV-1 Env PPI interactions with the host cellular receptor proteins are a potentially important class of inhibitors that can be used as novel anti-HIV therapeutics, especially with their unique modes of action, namely inhibition of Env-cellular protein interactions and triggering gp120 shedding from the virions.

In certain embodiments of this invention, AuNPs (20 nm) can be synthesized using a one-step aqueous method leading to particles with a narrow size distribution (±4 nm), which can be characterized using UV-Vis spectroscopy, dynamic light scattering (DLS) and transmission electron microscopy (TEM). In other embodiments, multivalent peptide-AuNP significantly improve the inhibition potency of the cyclic peptide alone. In yet other embodiments, the conjugate increases viral envelop shedding compared to peptide alone. In yet other embodiments, nanoparticle conjugation increases the potency of cyclic peptides of the invention in both inhibiting the virus-cell infection and inactivating the virus itself. The cyclic peptides of the invention, as well as their complexes with gold nanoparticles, may be used as microbicidal and therapeutic agents.

Compounds

The invention includes cyclic compounds of formula (I), or a salt, solvate, enantiomer or diastereoisomer thereof:

$$Xaa_1\text{-}Xaa_2\text{-}Xaa_3\text{-}Xaa_4\text{-}Xaa_5\text{-}Xaa_6\text{-}Xaa_7\text{-}Xaa_8\text{-}Xaa_9\text{-} \atop P_1 \quad (I),$$

wherein $Xaa_1$-$Xaa_2$-$Xaa_3$-$Xaa_4$-$Xaa_5$-$Xaa_6$-$Xaa_7$-$Xaa_8$-$Xaa_9$ is SEQ ID NO:2, and wherein in (I):

$Xaa_1$ is selected from the group consisting of absent, Glu and Arg;

$Xaa_2$ is selected from the group consisting of absent, Gly, Phe, Lys, Asp, Glu, Ile, Arg and Cit;

$Xaa_3$ is selected from the group consisting of absent, Asn, Asp, Ile, Glu, butanedioic acid (succinic acid), and 2-cyclohexylglycine;

$Xaa_4$ is selected from the group consisting of Asn and Asp;

$Xaa_8$ is a modified glycine of formula (III)

wherein $R^{III}$ is selected from the group consisting of $C_1$-$C_6$ alkyl and $C_3$-$C_6$ cycloalkyl;

$Xaa_6$ is the modified proline of formula (IV)

wherein in (IV) $R^{IV}$ is selected from the group consisting of: adamantyl substituted with 0-2 $C_1$-$C_6$ alkyl groups; —($C_0$-$C_4$ alkyl)phenyl, wherein the phenyl is substituted with 0-2 $C_1$-$C_6$ alkyl groups; phenyl substituted with $R^1$ and with 0-2 $C_1$-$C_6$ alkyl groups; and heteroaryl substituted with $R^1$ and with 0-2 $C_1$-$C_6$ alkyl groups; wherein each occurrence of $R^1$ is independently selected from the group consisting of phenyl substituted with 0-2 $C_1$-$C_6$ alkyl groups and heteroaryl substituted with 0-2 $C_1$-$C_6$ alkyl groups; and wherein each occurrence of heteroaryl is independently selected from the group consisting of pyridine, pyrimidine, thiophene, furan, pyrrole, imidazole, oxazole, oxadiazole, thiazole, thiadiazolyl, isothiazole and tetrazole;

$Xaa_7$ is selected from the group consisting of Trp and 3-(3-benzothienyl)-L-alanine;

$Xaa_8$ is selected from the group consisting of Ser, Thr, 2,4-diaminobutanoic acid, Orn and Lys;

$Xaa_9$ is selected from the group consisting of absent, 2,4-diaminobutanoic acid, Orn, Lys, Glu, Glu-Ala, Glu-Ala-Met, Glu-Ala-Met-Met, and 2-(2-(2-aminoethoxy) ethoxy) acetic acid;

$P_1$ is absent, or is a group that comprises at least one thiol group and is covalently linked through an amide bond to (i) the C-terminus of $Xaa_9$ if $Xaa_9$ is not absent, or (ii) the C-terminus of $Xaa_8$ if $Xaa_9$ is absent;

the side chain amino group of one residue selected from the group consisting of 2,4-diaminobutanoic acid at $Xaa_8$, Orn at $Xaa_8$, Lys at $Xaa_8$, 2,4-diaminobutanoic acid at $Xaa_9$, Orn at $Xaa_9$, and Lys at $Xaa_9$ forms an amide bond with the side chain carboxylic acid group of one residue selected from the group consisting of Glu at $Xaa_2$, Asp at $Xaa_2$, Glu at $Xaa_3$, Asp at $Xaa_3$, succinic acid at $Xaa_3$, and Asp at $Xaa_4$; and the C-terminus of $Xaa_8$ is optionally amidated if $Xaa_9$ and $P_1$ are absent, or the C-terminus of $Xaa_9$ is optionally amidated if $P_1$ is absent.

In certain embodiments, the cyclic compound is selected from the group consisting of:

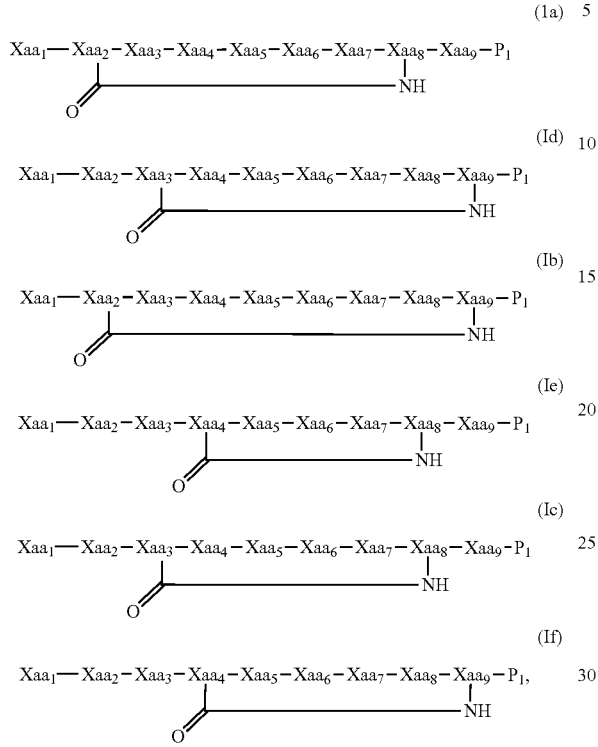

wherein in (Ia)-(If):
'NH' is derived from the side chain amino group of a residue selected from the group consisting of 2,4-diaminobutanoic acid at $Xaa_8$, Orn at $Xaa_8$, Lys at $Xaa_8$, 2,4-diaminobutanoic acid at $Xaa_9$, Orn at $Xaa_9$, and Lys at $Xaa_9$, and
'C=O' is derived from the side chain carboxylic acid group of a residue selected from the group consisting of Glu at $Xaa_2$, Asp at $Xaa_2$, Glu at $Xaa_3$, Asp at $Xaa_3$, succinic acid at $Xaa_3$, and Asp at $Xaa_4$.

In certain embodiments, the C-terminus of $Xaa_8$ is not amidated if $Xaa_9$ and $P_1$ are absent. In other embodiments, the C-terminus of $Xaa_9$ is not amidated if $P_1$ is absent.

In certain embodiments, the C-terminus of $Xaa_8$ is amidated if $Xaa_9$ and $P_1$ are absent. In other embodiments, the C-terminus of $Xaa_9$ is amidated if $P_1$ is absent.

In certain embodiments, $Xaa_8$ is selected from the group consisting of Ile, Leu, Nle, cyclopropylglycine, cyclobutylglycine, cyclopentylglycine and cyclohexylglycine.

In certain embodiments, $R^{III}$ is a secondary or tertiary hydrocarbyl group. In other embodiments, $R^{III}$ is selected from the group consisting of cyclohexyl, —CH(CH$_3$)(C$_1$-C$_4$ alkyl), and —C(CH$_3$)$_2$(C$_1$-C$_3$ alkyl).

In certain embodiments, if the carbon alpha to the carboxyl group of $Xaa_8$ is chiral, the stereochemistry of the alpha carbon is S.

In certain embodiments, in (IV) the heteroaryl is thiophene. In other embodiments, $R^{IV}$ is selected from the group consisting of: —(C$_0$-C$_4$ alkyl)phenyl, wherein the phenyl is substituted with 1-2 C$_1$-C$_6$ alkyl groups, wherein one of the C$_1$-C$_6$ alkyl groups is at the para position of the phenyl group;

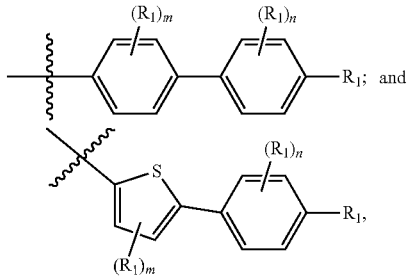

wherein each occurrence of $R_1$ is independently C$_1$-C$_6$ alkyl; m is 0, 1, or 2; and n is 0 or 1.

In certain embodiments, the cyclic compound is the cyclic compound of formula (II):

$$Xaa_1\text{-}Xaa_2\text{-}Xaa_3\text{-}Xaa_4\text{-}Xaa_5\text{-}Xaa_6\text{-}Xaa_7\text{-}Xaa_8\text{-}Xaa_9\text{-}P_1 \quad (II),$$

wherein $Xaa_1$-$Xaa_2$-$Xaa_3$-$Xaa_4$-$Xaa_5$-$Xaa_6$-$Xaa_7$-$Xaa_8$-$Xaa_9$ is SEQ ID NO:3, wherein in (II):
$Xaa_1$ is selected from the group consisting of absent, Glu and Arg;
$Xaa_2$ is selected from the group consisting of absent, Gly, Phe, Lys, Asp, Glu, Ile, Arg and Cit;
$Xaa_3$ is selected from the group consisting of Asn, Asp, succinic acid, and Glu;
$Xaa_4$ is Asn;
$Xaa_5$ is Ile;

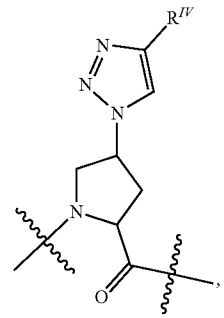

$Xaa_6$ is the modified proline of formula (IV) wherein in (IV) $R^{IV}$ is selected from the group consisting of: adamantyl substituted with 0-2 C$_1$-C$_6$ alkyl groups; —(C$_0$-C$_4$ alkyl)phenyl, wherein the phenyl is substituted with 0-2 C$_1$-C$_6$ alkyl groups; phenyl substituted with $R^1$ and with 0-2 C$_1$-C$_6$ alkyl groups; and heteroaryl substituted with $R^1$ and with 0-2 C$_1$-C$_6$ alkyl groups; wherein each occurrence of $R^1$ is independently selected from the group consisting of phenyl substituted with 0-2 C$_1$-C$_6$ alkyl groups and heteroaryl substituted with 0-2 C$_1$-C$_6$ alkyl groups; and wherein each occurrence of heteroaryl is independently selected from the group consisting of pyridine, pyrimidine, thiophene, furan, pyrrole, imidazole, oxazole, oxadiazole, thiazole, thiadiazolyl, isothiazole and tetrazole;
$Xaa_7$ is Trp;
$Xaa_8$ is selected from the group consisting of Ser, Thr, 2,4-diaminobutanoic acid, Orn and Lys;
$Xaa_9$ is selected from the group consisting of absent, 2,4-diaminobutanoic acid, Orn, Lys, Glu, Glu-Ala, Glu-Ala-Met, Glu-Ala-Met-Met, and 2-(2-(2-aminoethoxy) ethoxy) acetic acid;

P₁ is absent, or is a group that comprises at least one thiol group and is covalently linked through an amide bond to (i) the C-terminus of Xaa₉ if Xaa₉ is not absent or (ii) the C-terminus of Xaa₈ if Xaa₉ is absent;

the side chain amino group of one residue selected from the group consisting of 2,4-diaminobutanoic acid at Xaa₈, Orn at Xaa₈, Lys at Xaa₈, 2,4-diaminobutanoic acid at Xaa₉, Orn at Xaa₉, and Lys at Xaa₉ forms an amide bond with the side chain carboxylic acid group of one residue selected from the group consisting of Glu at Xaa₂, Asp at Xaa₂, Glu at Xaa₃, succinic acid at Xaa₃, and Asp at Xaa₃ and the C-terminus of Xaa₈ is optionally amidated if Xaa₉ and P₁ are absent, or the C-terminus of Xaa₉ is optionally amidated if P₁ is absent.

In certain embodiments, in (IV) R¹ is at the ortho position of R. In other embodiments, in (IV) R¹ is at the meta position of R. In yet other embodiments, in (IV) R¹ is at the para position of R.

In certain embodiments, P₁ is not absent. In other embodiments, P₁ comprises at least one cysteine residue. In yet other embodiments, P₁ comprises at least one natural or unnatural amino acid. In yet other embodiments, P₁ is a peptide consisting of at least two natural or unnatural amino acids. In yet other embodiments, P₁ is selected from the group consisting of:

βAla Gln βAla Cys-NH₂ (SEQ ID NO:4), βAla Gln βAla Cys (SEQ ID NO:5),
NH₂(CH₂CH₂O)₀₋₁₀CH₂C(=O)NHCH(CH₂SH)C(=O)OH,
NH₂(CH₂CH₂O)₀₋₁₀CH₂C(=O)NHCH(CH₂SH)C(=O)NH₂,
NH₂(CH₂)₀₋₁₂CH₂C(=O)NHCH(CH₂SH)C(=O)OH,
NH₂(CH₂)₀₋₁₂CH₂C(=O)NHCH(CH₂SH)C(=O)NH₂, and
NH₂CH₂CH₂OCH₂CH₂OC(=O)NHCH(CH₂SH)C(=O)NH₂.

In certain embodiments, the compound is at least one selected from the group consisting of:

29N-2 or 36 [also known as (3S,6S,14S,17S,20S,24S,25aS)-3-((1H-indol-3-yl)methyl)-14-amino-17-(2-amino-2-oxoethyl)-20-((S)-sec-butyl)-1,4,12,15,18,21-hexaoxo-24-(4-(4-(thiophen-2-yl)phenyl)-1H-1,2,3-triazol-1-yl)tetracosahydro-1H-pyrrolo[2,1-f][1,4,7,10,13,18]hexaazacyclotricosine-6-carboxamide]

37 [also known as (3S,6S,14S,17S,20S,24S,25aS)-3-((1H-indol-3-yl)methyl)-24-(4-([2,2'-bithiophen]-5-yl)-1H-1,2,3-triazol-1-yl)-14-amino-17-(2-amino-2-oxoethyl)-20-((S)-sec-butyl)-1,4,12,15,18,21-hexaoxotetracosahydro-1H-pyrrolo[2,1-f][1,4,7,10,13,18]hexaazacyclotricosine-6-carboxamide]

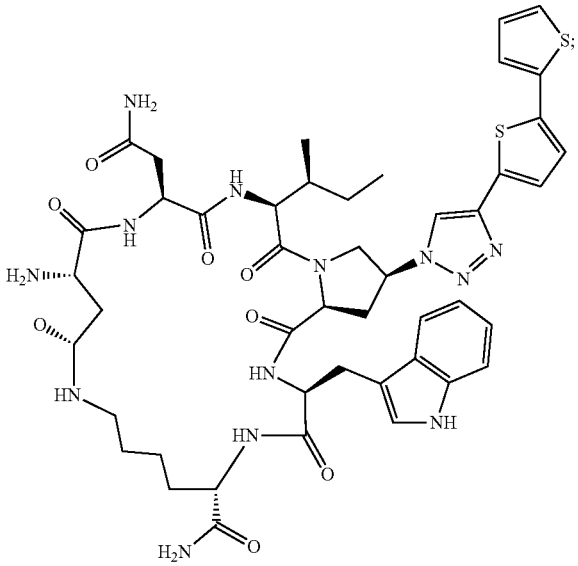 [SMILES: CC[C@H](C)[C@@H]1NC(=O)[C@H](CC(N)=O)NC(=O)[C@@H](N)C[C@@H](O)NCCCC[C@@H](C(N)=O)NC(=O)[C@H](Cc2c[nH]c3ccccc23)NC(=O)[C@@H]2C[C@H](n3cc(-c4ccc(-c5cccs5)s4)nn3)CN2C1=O]

38 [also known as (3S,6S,17S,20S,24S,25aS)-3-((1H-indol-3-yl)methyl)-17-(2-amino-2-oxoethyl)-20-((S)-sec-butyl)-1,4,12,15,18,21-hexaoxo-24-(4-(4-(thiophen-2-yl)phenyl)-1H-1,2,3-triazol-1-yl)tetracosahydro-1H-pyrrolo[2,1-f][1,4,7,10,13,18]hexaazacyclotricosine-6-carboxamide]

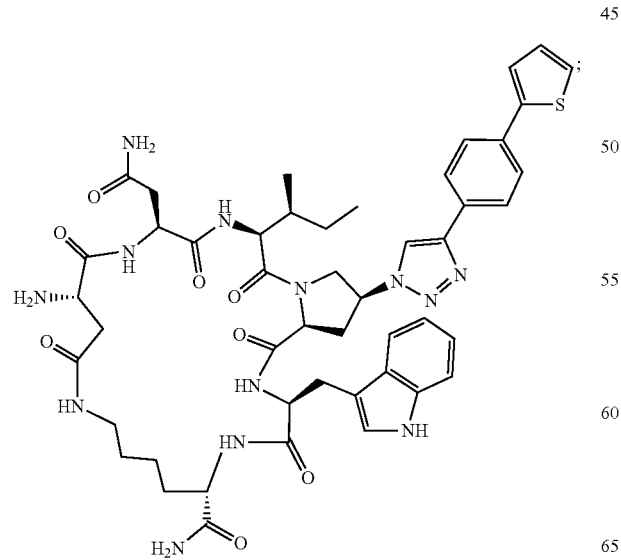

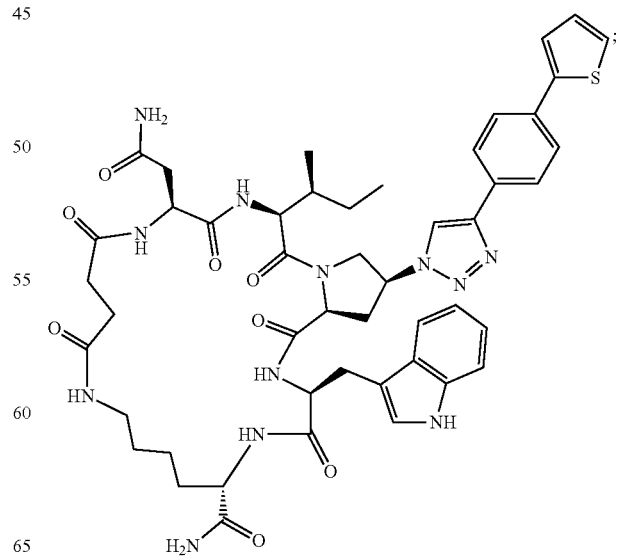

27

(3S,6S,17S,20S,24S,25aS)-3-((1H-indol-3-yl)methyl)-24-(4-([2,2'-bithiophen]-5-yl)-1H-1,2,3-triazol-1-yl)-17-(2-amino-2-oxoethyl)-20-((S)-sec-butyl)-1,4,12,15,18,21-hexaoxotetracosahydro-1H-pyrrolo[2,1-f][1,4,7,10,13,18]hexaazacyclotricosine-6-carboxamide

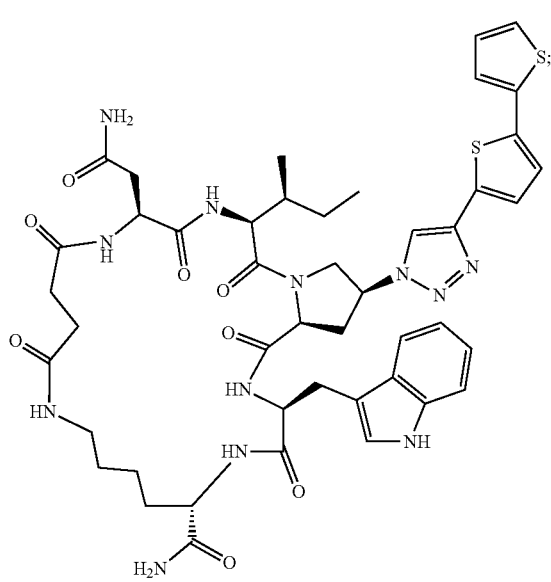 [SMILES: CC[C@H](C)[C@@H]1NC(=O)[C@H](CC(N)=O)NC(=O)CCC(=O)NCCCC[C@@H](C(N)=O)NC(=O)[C@H](Cc2c[nH]c3ccccc23)NC(=O)[C@@H]2C[C@H](n3cc(-c4ccc(-c5cccs5)s4)nn3)CN2C1=O]

28

(3S,6S,14S,17S,20S,24S,25aS)-3-((1H-indol-3-yl)methyl)-24-(4-([2,2'-bithiophen]-5-yl)-1H-1,2,3-triazol-1-yl)-14-amino-17-(2-amino-2-oxoethyl)-20-cyclohexyl-1,4,12,15,18,21-hexaoxotetracosahydro-1H-pyrrolo[2,1-f][1,4,7,10,13,18]hexaazacyclotricosine-6-carboxamide

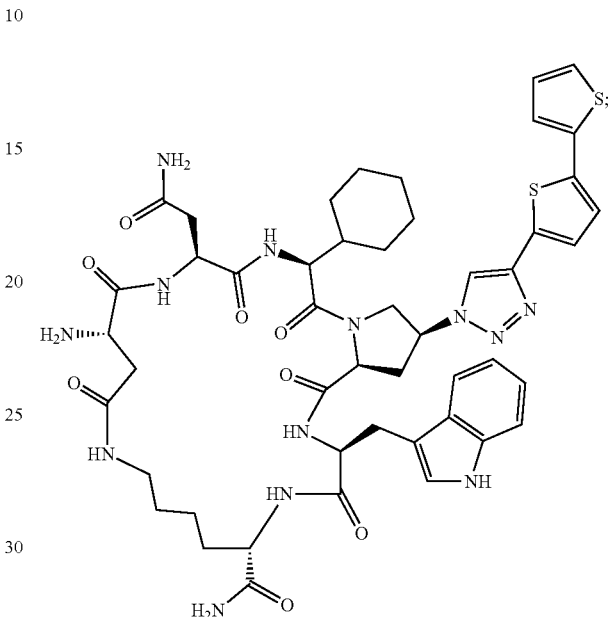

(3S,6S,14S,17S,20S,24S,25aS)-3-((1H-indol-3-yl)methyl)-14-amino-17-(2-amino-2-oxoethyl)-20-cyclohexyl-1,4,12,15,18,21-hexaoxo-24-(4-(4-(thiophen-2-yl)phenyl)-1H-1,2,3-triazol-1-yl)tetracosahydro-1H-pyrrolo[2,1-f][1,4,7,10,13,18]hexaazacyclotricosine-6-carboxamide (3S,6S,17S,20S,24S,25aS)-3-((1H-indol-3-yl)methyl)-17-(2-amino-2-oxoethyl)-20-cyclohexyl-1,4,12,15,18,21-hexaoxo-24-(4-(4-(thiophen-2-yl)phenyl)-1H-1,2,3-triazol-1-yl)tetracosahydro-1H-pyrrolo[2,1-f][1,4,7,10,13,18]hexaazacyclotricosine-6-carboxamide

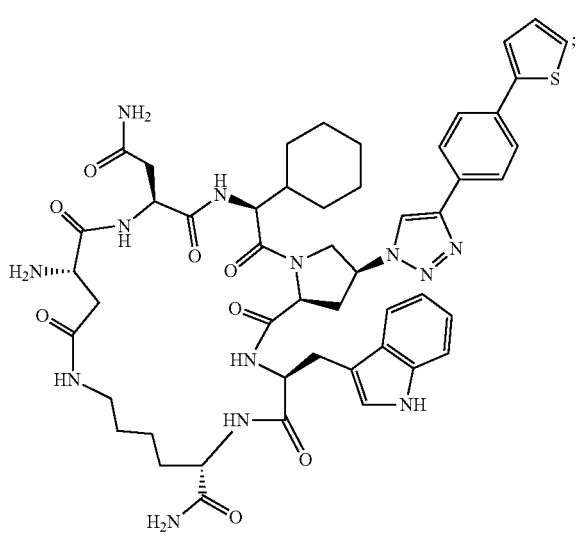 [SMILES: NC(=O)C[C@@H]1NC(=O)[C@@H](N)CC(=O)NCCCC[C@@H](C(N)=O)NC(=O)[C@H](Cc2c[nH]c3ccccc23)NC(=O)[C@@H]2C[C@H](n3cc(-c4ccc(-c5cccs5)cc4)nn3)CN2C(=O)[C@H](C2CCCCC2)NC1=O]

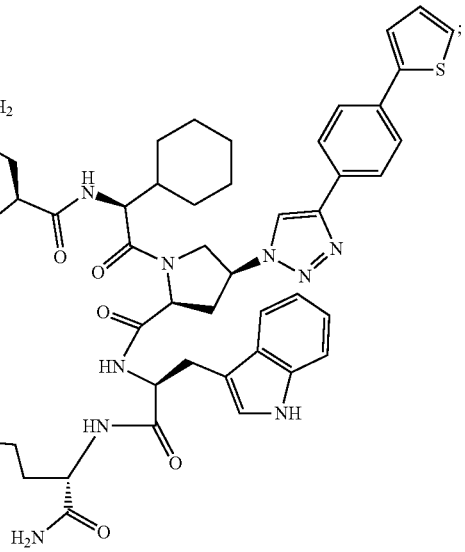

29

(3S,6S,17S,20S,24S,25aS)-3-((1H-indol-3-yl)methyl)-24-(4-([2,2'-bithiophen]-5-yl)-1H-1,2,3-triazol-1-yl)-17-(2-amino-2-oxoethyl)-20-cyclohexyl-1,4,12,15,18,21-hexaoxotetracosahydro-1H-pyrrolo[2,1-f][1,4,7,10,13,18]hexaazacyclotricosine-6-carboxamide

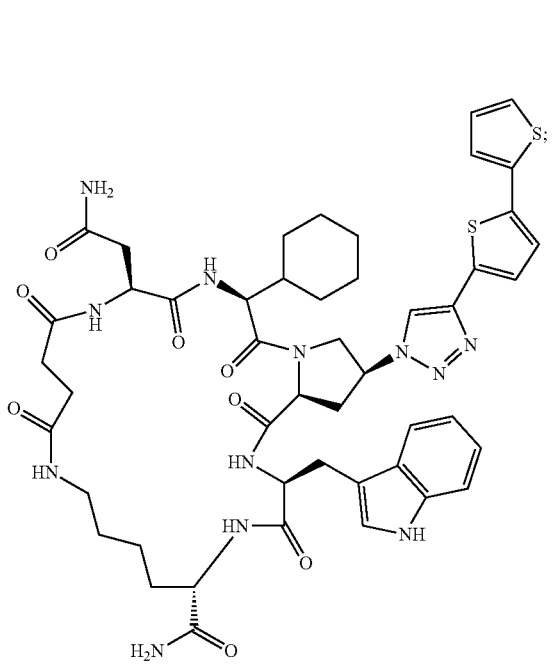 [SMILES: NC(=O)C[C@@H]1NC(=O)CCC(=O)NCCCC[C@@H](C(N)=O)NC(=O)[C@H](Cc2c[nH]c3ccccc23)NC(=O)[C@@H]2C[C@H](n3cc(-c4ccc(-c5cccs5)s4)nn3)CN2C(=O)[C@H](C2CCCCC2)NC1=O]

(3S,6S,14S,17S,20S,24S,25aS)-14-amino-17-(2-amino-2-oxoethyl)-3-(benzo[b]thiophen-3-ylmethyl)-20-((S)-sec-butyl)-1,4,12,15,18,21-hexaoxo-24-(4-(4-(thiophen-2-yl)phenyl)-1H-1,2,3-triazol-1-yl)tetracosahydro-1H-pyrrolo[2,1-f][1,4,7,10,13,18]hexaazacyclotricosine-6-carboxamide

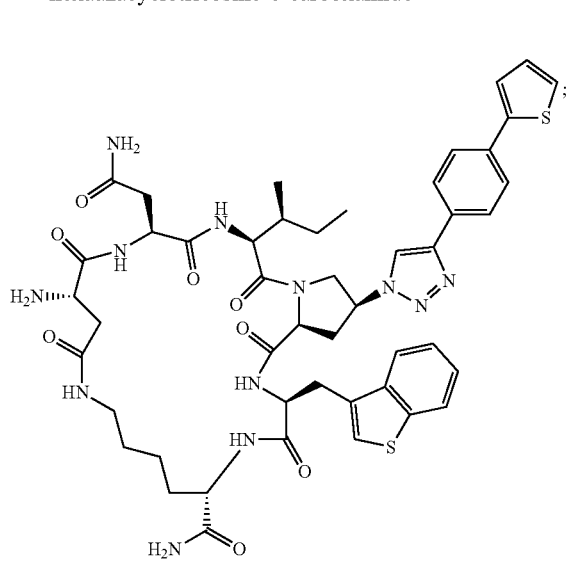

30

(3S,6S,14S,17S,20S,24S,25aS)-24-(4-([2,2'-bithiophen]-5-yl)-1H-1,2,3-triazol-1-yl)-14-amino-17-(2-amino-2-oxoethyl)-3-(benzo[b]thiophen-3-ylmethyl)-20-((S)-sec-butyl)-1,4,12,15,18,21-hexaoxotetracosahydro-1H-pyrrolo[2,1-f][1,4,7,10,13,18]hexaazacyclotricosine-6-carboxamide

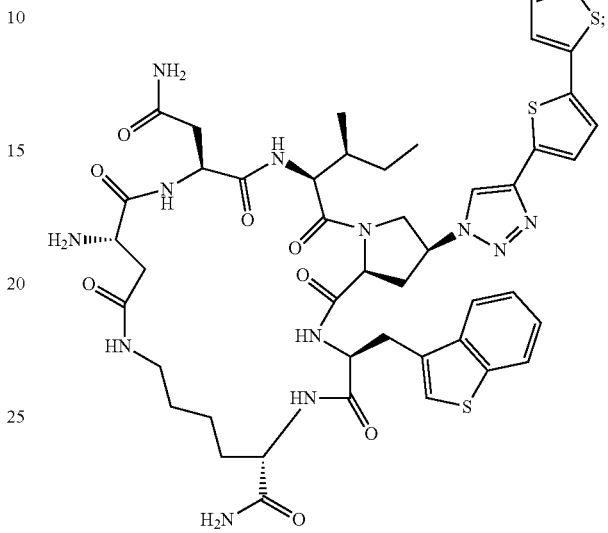

(3S,6S,17S,20S,24S,25aS)-17-(2-amino-2-oxoethyl)-3-(benzo[b]thiophen-3-ylmethyl)-20-((S)-sec-butyl)-1,4,12,15,18,21-hexaoxo-24-(4-(4-(thiophen-2-yl)phenyl)-1H-1,2,3-triazol-1-yl)tetracosahydro-1H-pyrrolo[2,1-f][1,4,7,10,13,18]hexaazacyclotricosine-6-carboxamide

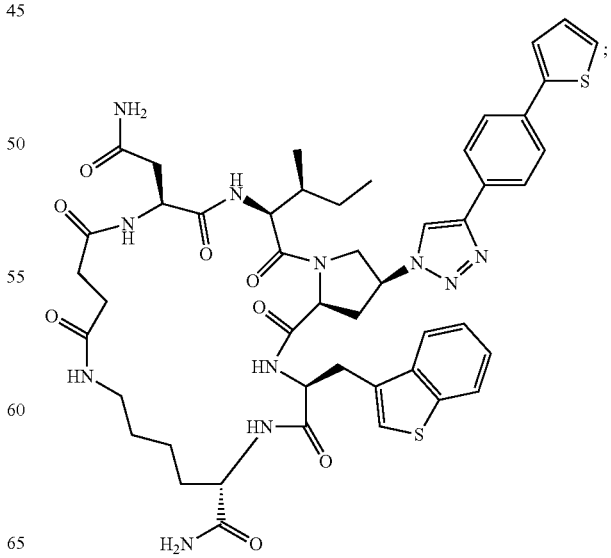

31

(3S,6S,17S,20S,24S,25aS)-24-(4-([2,2'-bithiophen]-5-yl)-1H-1,2,3-triazol-1-yl)-17-(2-amino-2-oxoethyl)-3-(benzo[b]thiophen-3-ylmethyl)-20-((S)-sec-butyl)-1,4,12,15,18,21-hexaoxotetracosahydro-1H-pyrrolo[2,1-f][1,4,7,10,13,18]hexaazacyclotricosine-6-carboxamide

32

((3S,6S,14S,17S,20S,24S,25aS)-24-(4-([2,2'-bithiophen]-5-yl)-1H-1,2,3-triazol-1-yl)-14-amino-17-(2-amino-2-oxoethyl)-3-(benzo[b]thiophen-3-ylmethyl)-20-cyclohexyl-1,4,12,15,18,21-hexaoxotetracosahydro-1H-pyrrolo[2,1-f][1,4,7,10,13,18]hexaazacyclotricosine-6-carboxamide

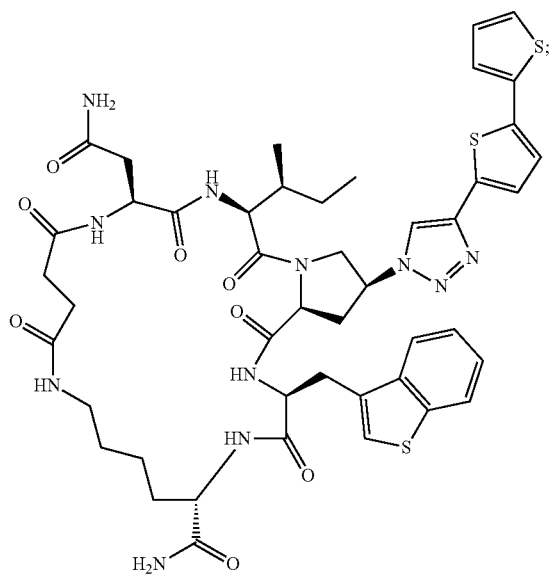 [SMILES: CC[C@H](C)[C@@H]1NC(=O)[C@H](CC(N)=O)NC(=O)CCC(=O)NCCCC[C@@H](C(N)=O)NC(=O)[C@H](Cc2csc3ccccc23)NC(=O)[C@@H]2C[C@H](n3cc(-c4ccc(-c5cccs5)s4)nn3)CN2C1=O]

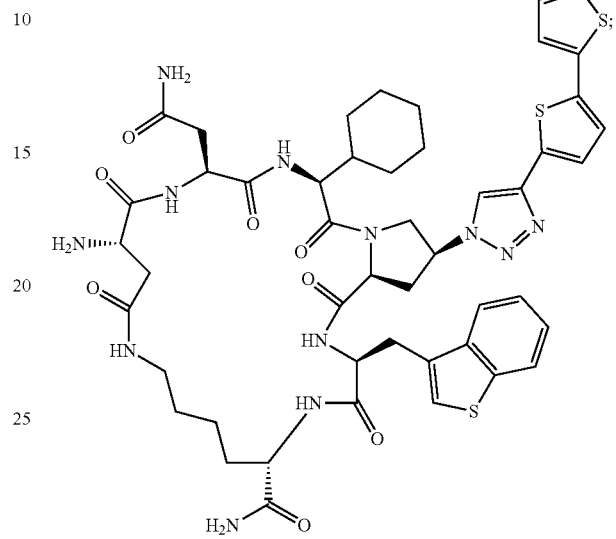

(3S,6S,14S,17S,20S,24S,25aS)-14-amino-17-(2-amino-2-oxoethyl)-3-(benzo[b]thiophen-3-ylmethyl)-20-cyclohexyl-1,4,12,15,18,21-hexaoxo-24-(4-(4-(thiophen-2-yl)phenyl)-1H-1,2,3-triazol-1-yl)tetracosahydro-1H-pyrrolo[2,1-f][1,4,7,10,13,18]hexaazacyclotricosine-6-carboxamide (3S,6S,17S,20S,24S,25aS)-17-(2-amino-2-oxoethyl)-3-(benzo[b]thiophen-3-ylmethyl)-20-cyclohexyl-1,4,12,15,18,21-hexaoxo-24-(4-(4-(thiophen-2-yl)phenyl)-1H-1,2,3-triazol-1-yl)tetracosahydro-1H-pyrrolo[2,1-f][1,4,7,10,13,18]hexaazacyclotricosine-6-carboxamide

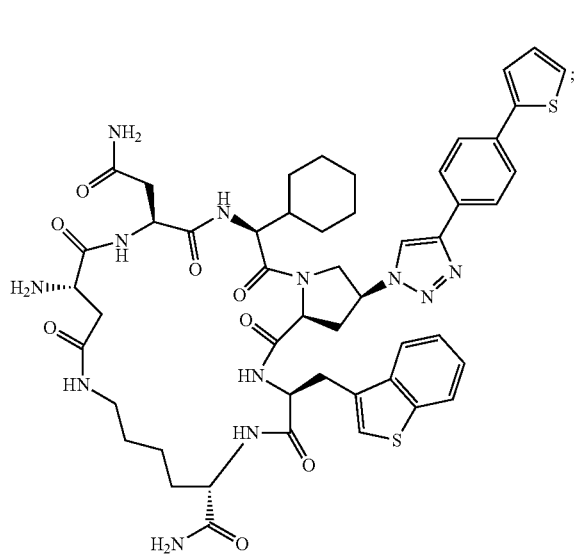 [SMILES: NC(=O)C[C@@H]1NC(=O)[C@@H](N)CC(=O)NCCCC[C@@H](C(N)=O)NC(=O)[C@H](Cc2csc3ccccc23)NC(=O)[C@@H]2C[C@H](n3cc(-c4ccc(-c5cccs5)cc4)nn3)CN2C(=O)[C@H](C2CCCCC2)NC1=O]

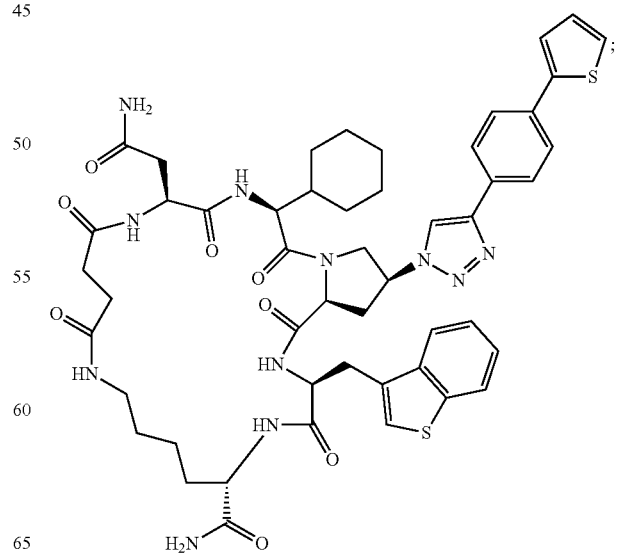

(3S,6S,17S,20S,24S,25aS)-24-(4-([2,2'-bithiophen]-5-yl)-1H-1,2,3-triazol-1-yl)-17-(2-amino-2-oxoethyl)-3-(benzo[b]thiophen-3-ylmethyl)-20-cyclohexyl-1,4,12,15,18,21-hexaoxotetracosahydro-1H-pyrrolo[2,1-f][1,4,7,10,13,18]hexaazacyclotricosine-6-carboxamide

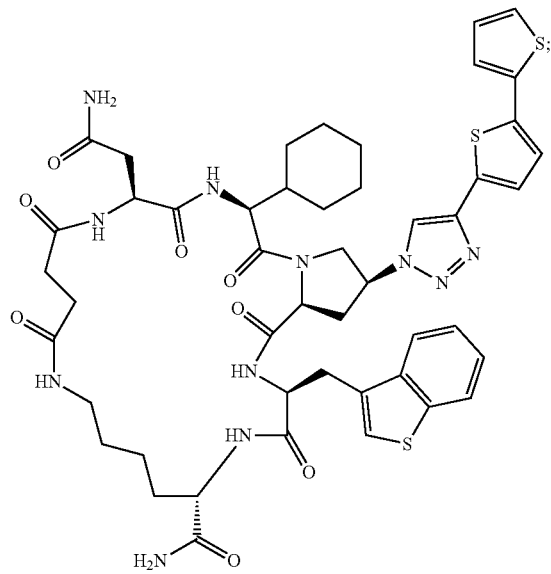 [SMILES: NC(=O)C[C@@H]1NC(=O)CCC(=O)NCCCC[C@@H](C(N)=O)NC(=O)[C@H](Cc2csc3ccccc23)NC(=O)[C@@H]2C[C@H](n3cc(-c4ccc(-c5cccs5)s4)nn3)CN2C(=O)[C@H](C2CCCCC2)NC1=O]

or a salt or solvate thereof.

In certain embodiments, the compound is a compound of formula (V):

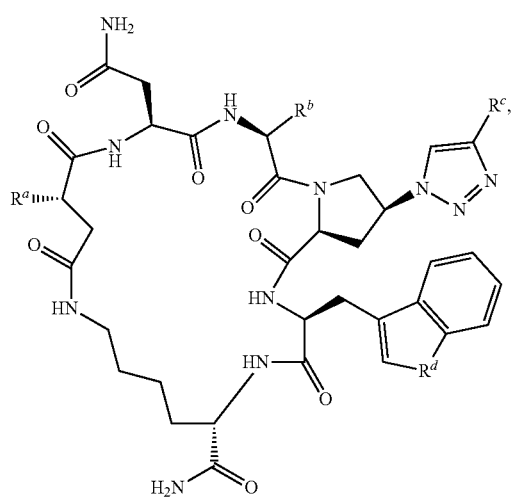

(V)

wherein:

$R^a$ is $NH_2$ or H;

$R^b$ is cyclohexyl or sec-butyl;

$R^c$ is selected from the group consisting of:

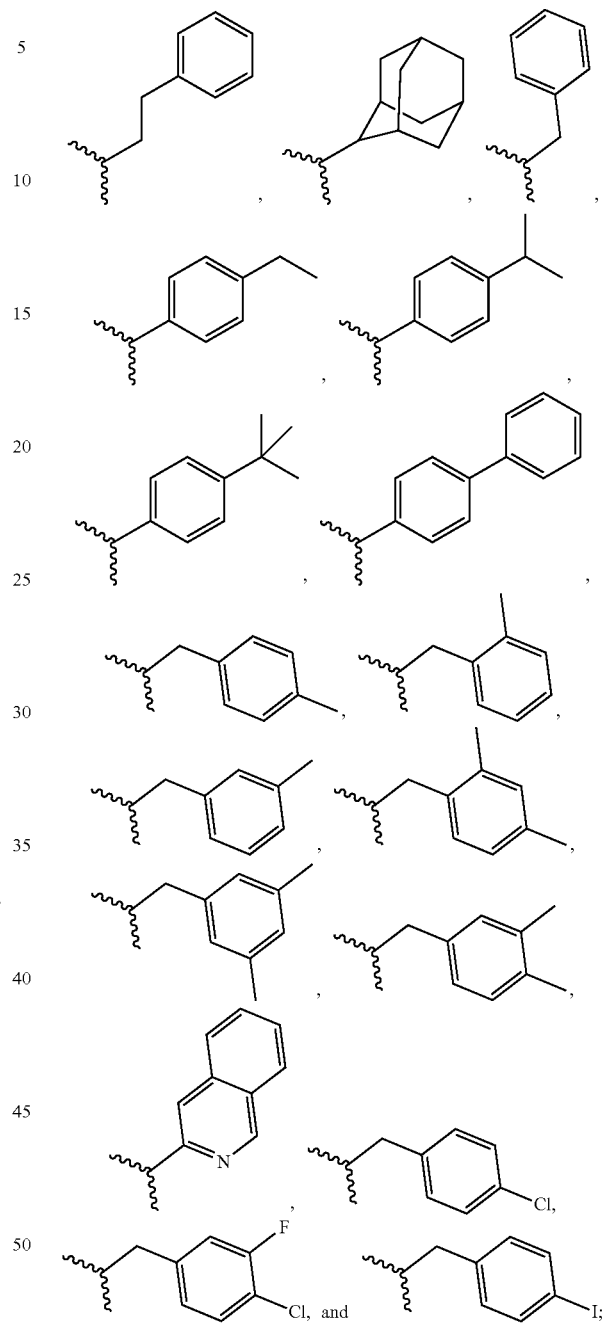

$R^d$ is NH or S;

or a salt or solvate thereof.

The invention further includes a cyclic peptide of the invention, or a salt or solvate thereof, wherein $P_1$ is not absent. In certain embodiments, the cyclic peptide is complexed through the at least one thiol group with at least one gold nanoparticle.

In certain embodiments, the at least one nanoparticle has an average diameter of about 20 nm. In other embodiments, the cyclic peptide of the invention complexed to the at least one gold nanoparticle is in a pharmaceutical composition. In yet other embodiments, the composition further comprises at least one pharmaceutically acceptable carrier. In yet other embodiments, the composition further comprises at least one additional compound useful for treating viral infections. In yet other embodiments, the at least one additional compound is selected from the group consisting of antiviral combination drugs, entry and fusion inhibitors, integrase inhibitors, non-nucleoside reverse transcriptase inhibitors, nucleoside reverse transcriptase inhibitors, protease inhibitors, and combinations thereof. In yet other embodiments, the peptide is encapsulated in a hydrogel and/or liposome. In yet other embodiments, the hydrogel and/or liposome is pH-responsive. In yet other embodiments, the hydrogel comprises a polymerized mixture of methacrylic acid and PEG-monomethyl ether monomethacrylate.

In certain embodiments, at least one compound of the invention is a component of a pharmaceutical composition further including at least one pharmaceutically acceptable carrier.

The compounds of the invention may possess one or more stereocenters, and each stereocenter may exist independently in either the (R)- or (S)-configuration. In certain embodiments, compounds described herein are present in optically active or racemic forms. The compounds described herein encompass racemic, optically-active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically-active starting materials, chiral synthesis, or chromatographic separation using a chiral stationary phase. In certain embodiments, a mixture of one or more isomer is utilized as the therapeutic compound described herein. In other embodiments, compounds described herein contain one or more chiral centers. These compounds are prepared by any means, including stereoselective synthesis, enantioselective synthesis and/or separation of a mixture of enantiomers and/or diastereomers. Resolution of compounds and isomers thereof is achieved by any means including, by way of non-limiting example, chemical processes, enzymatic processes, fractional crystallization, distillation, and chromatography.

The methods and formulations described herein include the use of N-oxides (if appropriate), crystalline forms (also known as polymorphs), solvates, amorphous phases, and/or pharmaceutically acceptable salts of compounds having the structure of any compound of the invention, as well as metabolites and active metabolites of these compounds having the same type of activity. Solvates include water, ether (e.g., tetrahydrofuran, methyl tert-butyl ether) or alcohol (e.g., ethanol) solvates, acetates and the like. In certain embodiments, the compounds described herein exist in solvated forms with pharmaceutically acceptable solvents such as water, and ethanol. In other embodiments, the compounds described herein exist in unsolvated form.

In certain embodiments, the compounds of the invention exist as tautomers. All tautomers are included within the scope of the compounds recited herein.

In certain embodiments, compounds described herein are prepared as prodrugs. A "prodrug" is an agent converted into the parent drug in vivo. In certain embodiments, upon in vivo administration, a prodrug is chemically converted to the biologically, pharmaceutically or therapeutically active form of the compound. In other embodiments, a prodrug is enzymatically metabolized by one or more steps or processes to the biologically, pharmaceutically or therapeutically active form of the compound.

In certain embodiments, sites on, for example, the aromatic ring portion of compounds of the invention are susceptible to various metabolic reactions. Incorporation of appropriate substituents on the aromatic ring structures may reduce, minimize or eliminate this metabolic pathway. In certain embodiments, the appropriate substituent to decrease or eliminate the susceptibility of the aromatic ring to metabolic reactions is, by way of example only, a deuterium, a halogen, or an alkyl group.

Compounds described herein also include isotopically-labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In certain embodiments, isotopically-labeled compounds are useful in drug and/or substrate tissue distribution studies. In other embodiments, substitution with heavier isotopes such as deuterium affords greater metabolic stability (for example, increased in vivo half-life or reduced dosage requirements). In yet other embodiments, substitution with positron emitting isotopes, such as $^{11}C$, $^{18}F$, $^{15}O$ and $^{13}N$, is useful in Positron Emission Topography (PET) studies for examining substrate receptor occupancy. Isotopically-labeled compounds are prepared by any suitable method or by processes using an appropriate isotopically-labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

Salts

The compositions described herein may form salts with acids or bases, and such salts are included in the present invention. In certain embodiments, the salts are pharmaceutically acceptable salts. The term "salts" embraces addition salts of free acids or free bases that are compositions of the invention. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compositions of the invention.

Suitable pharmaceutically acceptable acid addition salts may be prepared from an inorganic acid or from an organic acid. Examples of inorganic acids include hydrochloric, hydrobromic, hydriodic, nitric, carbonic, sulfuric, and phosphoric acids. Appropriate organic acids may be selected from aliphatic, cycloaliphatic, aromatic, aralphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Suitable pharmaceutically acceptable base addition salts of compositions of the invention include, for example, ammonium salts and metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. Examples of pharmaceutically unacceptable base addition salts include lithium salts and cyanate salts. All of these salts may be prepared from the corresponding composition by reacting, for example, the appropriate acid or base with the composition.

Methods

The invention includes a method of treating, reducing or preventing HIV-1 infection in a mammal in need thereof. The method comprises administering to the mammal a therapeutically effective amount of a compound or composition of the invention.

The invention further includes a method of reducing the risk of HIV-1 infection in a mammal at risk of HIV-1 exposure. The method comprises administering to the mammal a therapeutically effective amount of a compound or composition of the invention.

The method further includes a method of preparing a derivatized gold nanoparticle, wherein the gold nanoparticle is complexed with a cyclic peptide of the invention, wherein the cyclic peptide comprises at least one thiol group. The method comprises contacting a solution of the cyclic peptide with the nanoparticle, to generate a reaction system. The method further comprises stirring the reaction system for an amount of time, whereby the derivatized gold nanoparticle is formed. The method further comprises isolating the derivatized gold nanoparticle from the reaction system.

The invention also includes a method of promoting virolysis of a virus. The method comprises contacting the virus with a therapeutically effective amount of a compound or composition of the invention. In certain embodiments, the virus is in a mammal, for example a human.

The invention further includes a method of reducing the rate of or preventing entry of a virus into a cell of a mammal. The method comprises administering to the mammal a therapeutically effective amount of a compound or composition of the invention.

In certain embodiments, the virus comprises HIV-1. In other embodiments, the virus is HIV-1.

In certain embodiments, the mammal is further administered at least one additional compound useful for treating viral infections. In other embodiments, the at least one additional compound is selected from the group consisting of antiviral combination drugs, entry and fusion inhibitors, integrase inhibitors, non-nucleoside reverse transcriptase inhibitors, nucleoside reverse transcriptase inhibitors, protease inhibitors, and combinations thereof. In yet other embodiments, the at least one additional compound and the peptide are co-formulated.

In certain embodiments, the peptide is encapsulated in a hydrogel and/or liposome. In other embodiments, the hydrogel and/or liposome is pH-responsive. In yet other embodiments, the hydrogel comprises a polymerized mixture of methacrylic acid and PEG-monomethyl ether monomethacrylate.

In certain embodiments, the composition is administered to a mammal by a route selected from the group consisting of nasal, inhalational, topical, oral, buccal, rectal, pleural, peritoneal, vaginal, intramuscular, subcutaneous, transdermal, epidural, intratracheal, otic, intraocular, intrathecal and intravenous. In yet other embodiments, the mammal is human.

Combination Therapies

The compositions of the invention are useful in the methods of the invention in combination with one or more additional compounds useful for treating viral infections, such as but not limited to HIV infections. These additional compounds may comprise compounds or compositions identified herein, or compounds (e.g., commercially available compounds) known to treat, prevent, or reduce the symptoms of viral infections.

In non-limiting examples, the compositions of the invention may be used in combination with one or more of the following anti-HIV drugs:

HIV Combination Drugs: efavirenz, emtricitabine or tenofovir disoproxil fumarate (ATRIPLa®/BMS, Gilead); lamivudine or zidovudine (COMBIVIR®/GSK); abacavir or lamivudine (EPZICOM®/GSK); abacavir, lamivudine or zidovudine (TRIZIVIR®/GSK); emtricitabine, tenofovir disoproxil fumarate (TRUVADA®/Gilead).

Entry and Fusion Inhibitors: maraviroc (CELSENTRI®, SELZENTRY®/Pfizer); pentafuside or enfuvirtide (FUZEON®/Roche, Trimeris).

Integrase Inhibitors: raltegravir or MK-0518 (ISENTRESS®/Merck).

Non-Nucleoside Reverse Transcriptase Inhibitors: delavirdine mesylate or delavirdine (RESCRIPTOR®/Pfizer); nevirapine (VIRAMUNE®/Boehringer Ingelheim); stocrin or efavirenz (SUSTIVA®/BMS); etravirine (INTELENCE®/Tibotec).

Nucleoside Reverse Transcriptase Inhibitors: lamivudine or 3TC (EPIVIR®/GSK); FTC, emtricitabina or coviracil (EMTRIVA®/Gilead); abacavir (ZIAGEN®/GSK); zidovudina, ZDV, azidothymidine or AZT (RETROVIR®/GSK); ddI, dideoxyinosine or didanosine (VIDEX®/BMS); abacavir sulfate plus lamivudine (EPZICOM®/GSK); stavudine, d4T, or estavudina (ZERIT®/BMS); tenofovir, PMPA prodrug, or tenofovir disoproxil fumarate (VIREAD®/Gilead).

Protease Inhibitors: amprenavir (AGENERASE®/GSK, Vertex); atazanavir (REYATAZ®/BMS); tipranavir (APTIVUS®/Bochringer Ingelheim); darunavir (PREZIST®/Tibotec); fosamprenavir (TELZIR®, LEXIVAR/GSK, Vertex); indinavir sulfate (CRIXIVAN®/Merck); saquinavir mesylate (INVIRASE®/Roche); lopinavir or ritonavir (KALETRA®/Abbott); nelfinavir mesylate (VIRACEPT®/Pfizer); ritonavir (NORVIR®/Abbott).

A synergistic effect may be calculated, for example, using suitable methods such as, for example, the Sigmoid-$E_{max}$ equation (Holford & Scheiner, 19981, Clin. Pharmacokinet. 6:429-453), the equation of Loewe additivity (Loewe & Muischnek, 1926, Arch. Exp. Pathol Pharmacol. 114:313-326) and the median-effect equation (Chou & Talalay, 1984, Adv. Enzyme Regul. 22:27-55). Each equation referred to above may be applied to experimental data to generate a corresponding graph to aid in assessing the effects of the drug combination. The corresponding graphs associated with the equations referred to above are the concentration-effect curve, isobologram curve and combination index curve, respectively.

Administration/Dosage/Formulations

Routes of administration of any of the compounds and/or compositions of the invention include oral, nasal, rectal, intravaginal, parenteral (e.g., IM, IV and SC), buccal, sublingual or topical. The regimen of administration may affect what constitutes an effective amount. The therapeutic formulations may be administered to the subject either prior to or after the onset of a viral infection. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a subject, preferably a mammal, more preferably a human, may be carried out using known procedures, at dosages and for periods of time effective to treat a viral infection in the subject. An effective amount of the therapeutic compound necessary to achieve a therapeutic effect may vary according to factors such as the state of the disease or disorder in the subject; the age, sex, and weight of the subject; and the ability of the therapeutic compound to treat a viral infection in the subject. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound useful within the invention is from about 1 and 5,000 mg/kg of body weight/per day. One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular subject, composition, and mode of administration, without being toxic to the subject.

In particular, the selected dosage level depends upon a variety of factors, including the activity of the particular compound employed, the time of administration, the rate of excretion of the compound, the duration of the treatment, other drugs, compounds or materials used in combination with the compound, the age, sex, weight, condition, general health and prior medical history of the subject being treated, and like factors well, known in the medical arts.

A medical doctor, e.g., physician or veterinarian, having ordinary skill in the art may readily determine and prescribe the effective amount of the pharmaceutical composition required. For example, the physician or veterinarian may start doses of the compounds useful within the invention employed in the pharmaceutical composition at levels lower than that required in order to achieve the desired therapeutic effect and gradually increase the dosage until the desired effect is achieved.

In certain embodiments, it is especially advantageous to formulate the compound in dosage unit form for case of administration and uniformity of dosage. Dosage unit form as used herein refers to physically discrete units suited as unitary dosages for the subjects to be treated; each unit containing a predetermined quantity of therapeutic compound calculated to produce the desired therapeutic effect in association with the required pharmaceutical vehicle. The dosage unit forms of the invention are dictated by and directly dependent on the unique characteristics of the therapeutic compound and the particular therapeutic effect to be achieved, and the limitations inherent in the art of compounding/formulating such a therapeutic compound for the treatment of an HIV-1 infection in a subject.

In certain embodiments, the compositions of the invention are formulated using one or more pharmaceutically acceptable excipients or carriers. In certain embodiments, the pharmaceutical compositions of the invention comprise a therapeutically effective amount of a compound useful within the invention and a pharmaceutically acceptable carrier.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it will be preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

In certain embodiments, the compositions of the invention are administered to the subject in dosages that range from one to five times per day or more. In other embodiments, the compositions of the invention are administered to the subject in range of dosages that include, but are not limited to, once every day, every two, days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any subject are determined by the attending physical taking all other factors about the subject into account.

Compounds useful within the invention for administration may be in the range of from about 1 mg to about 10,000 mg, about 20 mg to about 9,500 mg, about 40 mg to about 9,000 mg, about 75 mg to about 8,500 mg, about 150 mg to about 7,500 mg, about 200 mg to about 7,000 mg, about 3050 mg to about 6,000 mg, about 500 mg to about 5,000 mg, about 750 mg to about 4,000 mg, about 1 mg to about 3,000 mg, about 10 mg to about 2,500 mg, about 20 mg to about 2,000 mg, about 25 mg to about 1,500 mg, about 50 mg to about 1,000 mg, about 75 mg to about 900 mg, about 100 mg to about 800 mg, about 250 mg to about 750 mg, about 300 mg to about 600 mg, about 400 mg to about 500 mg, and any and all whole or partial increments therebetween.

In certain embodiments, the dose of a compound useful within the invention is from about 1 mg and about 2,500 mg. In other embodiments, a dose of a compound useful within the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in certain embodiments, a dose of a second compound (i.e., an HIV-1 antiviral) as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments therebetween.

In certain embodiments, the present invention is directed to a packaged pharmaceutical composition comprising a container holding a therapeutically effective amount of a compound useful within the invention, alone or in combination with a second pharmaceutical agent; and instructions for using the compound to treat, prevent, or reduce one or more symptoms of an HIV-1 infection in a subject.

Granulating techniques are well known in the pharmaceutical art for modifying starting powders or other particulate materials of an active ingredient. The powders are typically mixed with a binder material into larger permanent free-flowing agglomerates or granules referred to as a "granulation." For example, solvent-using "wet" granulation processes are generally characterized in that the powders are combined with a binder material and moistened with water or an organic solvent under conditions resulting in the formation of a wet granulated mass from which the solvent must then be evaporated.

Melt granulation generally consists in the use of materials that are solid or semi-solid at room temperature (i.e. having a relatively low softening or melting point range) to promote granulation of powdered or other materials, essentially in the absence of added water or other liquid solvents. The low melting solids, when heated to a temperature in the melting point range, liquefy to act as a binder or granulating medium. The liquefied solid spreads itself over the surface of powdered materials with which it is contacted, and on cooling, forms a solid granulated mass in which the initial materials are bound together. The resulting melt granulation may then be provided to a tablet press or be encapsulated for preparing the oral dosage form. Melt granulation improves the dissolution rate and bioavailability of an active (i.e. drug) by forming a solid dispersion or solid solution.

U.S. Pat. No. 5,169,645 discloses directly compressible wax-containing granules having improved flow properties. The granules are obtained when waxes are admixed in the melt with certain flow improving additives, followed by cooling and granulation of the admixture. In certain embodiments, only the wax itself melts in the melt combination of the wax(es) and additives(s), and in other cases both the wax(es) and the additives(s) will melt.

The present invention also includes a multilayer tablet comprising a layer providing for the delayed release of one or more compounds useful within the invention, and a further layer providing for the immediate release of a medication for HIV-1 infection. Using a wax/pH-sensitive polymer mix, a gastric insoluble composition may be obtained in which the active ingredient is entrapped, ensuring its delayed release.

Formulations may be employed in admixtures with conventional excipients, i.e., pharmaceutically acceptable organic or inorganic carrier substances suitable for oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents, e.g., other analgesic agents.

For oral application, particularly suitable are tablets, dragees, liquids, drops, suppositories, or capsules, caplets and gelcaps. The compositions intended for oral use may be prepared according to any method known in the art and such compositions may contain one or more agents selected from the group consisting of inert, non-toxic pharmaceutically excipients that are suitable for the manufacture of tablets. Such excipients include, for example an inert diluent such as lactose; granulating and disintegrating agents such as cornstarch; binding agents such as starch; and lubricating agents such as magnesium stearate. The tablets may be uncoated or they may be coated by known techniques for elegance or to delay the release of the active ingredients. Formulations for oral use may also be presented as hard gelatin capsules wherein the active ingredient is mixed with an inert diluent.

The compounds for use in the invention may be formulated for administration by any suitable route, such as for oral or parenteral, for example, transdermal, transmucosal (e.g., sublingual, lingual, (trans) buccal, (trans) urethral, vaginal (e.g., trans- and perivaginally), (intra) nasal and (trans) rectal), intravesical, intrapulmonary, intraduodenal, intragastrical, intrathecal, subcutaneous, intramuscular, intradermal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Oral Administration:

For oral administration, the compositions of the invention may be in the form of tablets or capsules prepared by conventional means with pharmaceutically acceptable excipients such as binding agents (e.g., polyvinylpyrrolidone, hydroxypropylcellulose or hydroxypropylmethylcellulose); fillers (e.g., cornstarch, lactose, microcrystalline cellulose or calcium phosphate); lubricants (e.g., magnesium stearate, talc, or silica); disintegrates (e.g., sodium starch glycollate); or wetting agents (e.g., sodium lauryl sulphate). If desired, the tablets may be coated using suitable methods and coating materials such as OPADRY™ film coating systems available from Colorcon, West Point, Pa. (e.g., OPADRY™ OY Type, OYC Type, Organic Enteric OY—P Type, Aqueous Enteric OY-A Type, OY-PM Type and OPADRY™ White, 32K18400). Liquid preparation for oral administration may be in the form of solutions, syrups or suspensions. The liquid preparations may be prepared by conventional means with pharmaceutically acceptable additives such as suspending agents (e.g., sorbitol syrup, methyl cellulose or hydrogenated edible fats); emulsifying agent (e.g., lecithin or acacia); non-aqueous vehicles (e.g., almond oil, oily esters or ethyl alcohol); and preservatives (e.g., methyl or propyl p-hydroxy benzoates or sorbic acid).

Parenteral Administration

For parenteral administration, the compositions of the invention may be formulated for injection or infusion, for example, intravenous, intramuscular or subcutaneous injection or infusion, or for administration in a bolus dose and/or continuous infusion. Suspensions, solutions or emulsions in an oily or aqueous vehicle, optionally containing other formulatory agents such as suspending, stabilizing and/or dispersing agents may be used.

Additional Administration Forms

Additional dosage forms of this invention include dosage forms as described in U.S. Pat. Nos. 6,340,475, 6,488,962, 6,451,808, 5,972,389, 5,582,837, and 5,007,790. Additional dosage forms of this invention also include dosage forms as described in U.S. Patent Applications Nos. 2003/0147952, 2003/0104062, 2003/0104053, 2003/0044466, 2003/0039688, and 2002/0051820. Additional dosage forms of this invention also include dosage forms as described in PCT Applications Nos. WO 03/35041, WO 03/35040, WO 03/35029, WO 03/35177, WO 03/35039, WO 02/96404, WO 02/32416, WO 01/97783, WO 01/56544, WO 01/32217, WO 98/55107, WO 98/11879, WO 97/47285, WO 93/18755, and WO 90/11757.

Controlled Release Formulations and Drug Delivery Systems:

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material which provides sustained release properties to the compounds. As such, the compounds for use the method of the invention may be administered in the form of microparticles, for example, by injection or in the form of wafers or discs by implantation.

In a preferred embodiment of the invention, the compounds useful within the invention are administered to a subject, alone or in combination with another pharmaceutical agent, using a sustained release formulation.

The term delayed release is used herein in its conventional sense to refer to a drug formulation that provides for an initial release of the drug after some delay following drug administration and that may, although not necessarily, include a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, or about 10 minutes, and any and all whole or partial increments thereof after drug administration.

Dosing:

The therapeutically effective amount or dose of a compound of the present invention will depend on the age, sex and weight of the subject, the current medical condition of the subject and the nature of the infection by an HIV-1 being treated. The skilled artisan will be able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 4 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days.

The compounds for use in the method of the invention may be formulated in unit dosage form. The term "unit dosage form" refers to physically discrete units suitable as unitary dosage for subjects undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 4 or more times per day). When multiple daily doses are used, the unit dosage form may be the same or different for each dose.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood, that modifications in reaction conditions, including but not limited to reaction times, reaction size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

The following examples further illustrate aspects of the present invention. However, they are in no way a limitation of the teachings or disclosure of the present invention as set forth herein.

Examples

The invention is now described with reference to the following Examples. These Examples are provided for the purpose of illustration only, and the invention is not limited to these Examples, but rather encompasses all variations that are evident as a result of the teachings provided herein.

Materials

All chemical reagents, unless specified, were purchased from commercial sources or prepared according to published procedures. A CEM microwave synthesizer (Liberty Blue) is used for solid phase peptide synthesis. Fmoc-4-azido-Proline was synthesized as previously reported (Rashad, et al., 2015, J. Med. Chem. 58:7603-8). All other Fmoc-, Boc-protected amino acids, N,N'-diisopropylcarbodiimide (DIC), ethyl (hydroxyimino) cyanoacetate (OxymaPure) and rink amide resin (100-200 mesh size, 0.53 meq/g substitution)

were purchased from Chem-Impex International, INC. CuI catalyst for the click reaction, and hydrazine, were purchased from Sigma Aldrich. HPLC purifications were performed using a Waters® HPLC system with reverse phase $C_{18}$ semi-prep/prep columns. Purity checks of PTs were carried out by analytical $C_{18}$ RP-HPLC, using a Beckman-Coulter® HPLC system. All synthesized cPTs were >95% pure, as judged by purity checks using an analytical $C_{18}$ RP-HPLC column and BeckmanCoulter HPLC system. HPLC grade ACN, Millipore-MilliQ water and 0.1% TFA were used as solvents for the HPLC purification. Mass validation was performed in-house (using Thermo Scientific LTQ XL Ion Trap LC/MS) and at the Wistar Proteomics Facility (using MALDI-TOF Mass Spectrometry). All data were collected on an ABI/PerSeptive (Framingham, MA) Voyager DE-PRO MALDI-TOF instrument in positive-ion mode; samples were spotted onto a 96 well plate coated using alpha-cyano-4-cinnamic acid matrix (Sigma) at 10 mg/mL.

Expression and purification of wild-type gp120YU-2 was performed as described in International Application Publication No. WO 2016/094518, which is incorporated herein by reference in its entirety.

General methods for gold nanoparticle (AuNP) synthesis and characterization are described in International Application Publication No. WO 2016/094518, which is incorporated herein by reference in its entirety Example 1: Cyclic Peptides Cyclic peptides of the invention can be prepared using intramolecular cyclization according to the methods disclosed in International Application Publication No. WO 2016/094518, which is incorporated herein by reference in its entirety.

Chemical Synthesis of cPTs (3-38)

Alkynes a10-a16 were synthesized from the corresponding benzyl bromides a1-a9 following the procedures previously described (Louvel, et al., 2013, J. Med. Chem. 56:9427-40). Alkynes a10-a16 were used in click reactions without purification, because they are volatile and unstable upon storage. Mass validation of all cPTs was performed using Thermo Scientific LTQ XL Ion Trap LC/MS (Table 4).

General Synthesis of Alkynes a9-a16

To a solution of ethynyltrimethylsilane (40 mmol) in 20 mL THF at 0° C., was added i-PrMgCl (2 M solution in THF) dropwise, and the mixture was stirred at 0° C. for 30 min, and allowed to warm up to r.t. for 30 min. CuBr (6 mmol) was added, and the mixture was stirred at r.t. for 1 h. The corresponding benzyl bromide a1-a8 was added, and the mixture was heated under reflux for 4 h. The reaction mixture was then cooled to r.t. before pouring onto saturated $NH_4Cl$ solution (500 mL). The mixture was extracted twice with diethyl ether, the combined organic layers were washed with water and brine and then dried over $MgSO_4$. Diethyl ether was evaporated under vacuum, and the crude residues were used for the next step without purification. The residues were dissolved in MeOH, and then cooled to 0° C. before adding $K_2CO_3$ (40 mmol). The mixture was stirred at 0° C. for 2 h before adding 20 mL water. After layer separation, the aqueous layer was extensively extracted with diethyl ether, and the combined ethereal layer was washed with brine and dried over $MgSO_4$. Ether was removed under vacuum, and the remaining liquid alkyne was immediately used for the click reaction with the resin-bound cyclic peptide.

On-Resin Synthesis of the Bi-Aryl System on cPT

After the on-resin click reaction with the bromo-alkyne (Scheme 2), the resin-bound protected cPT was washed sequentially with 5% HCl, DMF and DCM before transferring to a 25 mL round bottom flask for Suzuki reaction. The flask was charged with 5 mol % tetrakis(triphenylphosphine) palladium (0) $(Pd[PPh_3]_4)$, aqueous 2 M $Na_2CO_3$ (5 equivalents) and 5 equivalents of thiophen-2-ylboronic acid dissolved in 5 mL DMF, and the reaction mixture was flushed with $N_2$ for 10 min. The flask was then capped and microwave irradiated at 85° C. for 30 min to 1 h. Few resin beads were collected and subjected to cleavage conditions to check the coupling, which indicated complete reaction, without traces of the starting material (~ 87% yield for the coupling step based on cleavage from 0.1 g resin). The vessel was then cooled and the resin was extensively washed with 5% HCl, water, DMF and DCM. Cleavage from resin, deprotection and HPLC purification were performed. The overall yield of 36 and 37 was 55% and 49%, respectively. The same coupling procedures were applied during the synthesis of the amine-free cPT 38 with overall yield of 61%

Example 2: Pseudovirus Production, Antiviral Assay and Cytotoxicity Assay

Pseudoviruses were produced as previously described (Umashankara, et al., 2010, ChemMedChem 5:1871-9). Briefly, HEK 293T cells ($3\times10^6$) were co-transfected with 4 µg of BaL.01 gp160 plasmid and 8 µg of NL4-3 R-E-Luc+ core DNA (obtained from the NIH AIDS Reagent Program), using Polyethyleneimine (PEI) as a transfection vehicle. After 72 hours, the supernatant containing virus was collected and filtered using a 0.45 µm syringe filter (Corning). The supernatant was then loaded on a 10 ml Iodixanol gradient; 6%-20% (Optiprep, Sigma Aldrich) and centrifuged on SW41Ti rotor (Beckman Coulter) at 30,000 RPM for 2 hours at 4° C. Virus samples were pooled from fractions 6 through 9 in 1 ml aliquots and diluted in serum free media, before storage in −80° C. All batches of virus were titrated for infectivity and p24 content immediately after production.

Pseudoviral infection assays were carried out as previously described (Emilch, et al., 2013, Biochem. 52:2245-2261). Briefly, 7500 HOS.T4.R[5] cells were seeded in 96 well plates on day one. 24 hours later, virus stocks were diluted in growth media such that the final dilution gave $1\times10^6$ luminescence counts. Inhibitors to be tested were solubilized in 1xPBS containing 2% DMSO and serially diluted in 1.5 mL tubes. Virus was then added to these inhibitors-containing tubes, 1:1 (v/v), and the tubes were mixed by repeated inversions. Positive control (100%) contained virus treated with PBS while the negative control (0%) contained no virus. The samples were incubated at 37° C. for 45 minutes before addition to the cells. The plates were incubated for 24 hours at 37° C. before the medium was changed. 24 hours post media change infection, the cells were lysed using Passive Lysis Buffer (Promega). Lysed cells were then transferred to a 96 well white plate (Greiner) and mixed with Luciferin salt (Anaspec) in 0.1 M potassium phosphate buffer containing 0.1 M magnesium sulfate and the luminescence measured using a Wallace 1450 Microbeta Luminescence reader.

Luminiscence reading for each inhibitor concentration was normalized to the controls and plotted against the inhibitor concentration. Inhibition potencies were then determined by calculating the inhibitor concentration required for 50% inhibition of maximal binding ($IC_{50}$) after fitting the plot using the four parameter Logistic sigmoidal fit in Origin 8.0.

Cytotoxicity Assay:

cPTs 36 and 37 were tested for cytotoxicity in vitro with HOS.T4.R5 cells. The latter were seeded at 75,00 cells per well and incubated with peptides as described elsewhere herein for the infection inhibition assays. Cell viability was determined using the tetrazolium salt premix reagent WST-1 from TaKaRa Bio, Inc., by following the manufacturer's protocol. The formazan product was measured 24 h post-exposure using a microplate reader (Molecular Devices) at an absorbance wavelength of 450 nm.

Example 3: Production of HIV-1 gp120 and Soluble CD4 Proteins

Reagents:

*Escherichia coli* strain Stbl2 cells were products of Novagen Inc. (Madison, WI). DNA plasmids encoding BaL.01 gp160 and NL4-3 R-E-Luc+ were obtained from the NIH AIDS Reagent Program, Division of AIDS, NIAID. pcDNA3.1 vector carrying CD4 was a gift from Navid Madani. 17b IgG was purchased from Strategic Diagnostics Inc. (Newark, DE). All other reagents used were of the highest analytical grade available.

Expression and Purification of Wild-Type gp120YU-2:

The DNA for gp120YU-2 in pcDNA3.1 vector for transient transfection was purified using a Qiagen MaxiPrep kit (Qiagen) after transforming into Stbl2 competent cells. The purified DNA encoding gp120 YU-2 was transfected into HEK 293F cells according to manufacturer's protocol (Invitrogen). Five days after transfection was initiated, cells were harvested and spun down (3000 RPM), and the supernatant was filtered through 0.2 µm filters. Purification was performed over a 17b antibody-coupled column prepared using an NHS-activated Sepharose, HiTrap HP column (GE Healthcare). gp120 was eluted from the column using 0.1 M Glycine buffer pH 2.4. The pH of the eluted protein was rapidly neutralized by addition of IM Tris pH 8.0. Identity of the eluted fractions was confirmed by SDS-PAGE and Western blotting using antibody D7324 (Aalto Bioreagents). Eluted protein was immediately buffer exchanged into PBS using spin-columns (Amicon Ultra Ultracell-30K, Millipore). Protein was filtered through 0.45 µm syringe filters (Millex-LH, Millipore) and separated by size exclusion on a HiLoad 26/60 Superdex 200 HR prepacked gel filtration column (GE). Purity of eluted fractions and monomeric state of gp120 were identified by SDS-PAGE. Monomeric fractions were pooled, concentrated, frozen and stored at −80° C.

Four Domain Soluble CD4 Production:

Hexa histidine-tagged 4-domain soluble CD4 (CD4) was produced by transient transfection into 293F cells using standard protocols (Gibco). CD4 was separated from the expression medium by Nickel affinity purification on HiTrap columns (GE) using an Akta FPLC System (GE). CD4 was further purified by size-exclusion on a Superdex 200 column (GE). Protein size and functionality were verified by SDS PAGE and anti-gp120 ELISA, respectively.

Example 4: Inhibition of HIV-1 gp120 Proteins

Surface Plasmon Resonance (SPR) assays:

SPR experiments are performed on a Biacore 3000 optical biosensor (GE Healthcare). All experiments are carried out at 25° C. using standard PBS buffer pH=7.4 with 0.005% surfactant Tween and 2% DMSO.

Three flow cells in the CM5 chip were used for amine coupling of different ligands through standard 1-ethyl-3-(3-(dimethylamino) propyl) carbodiimide (EDC)/N-hydroxysuccinamide (NHS) chemistry. Flow cell 1 containing 2000 RUs of immobilized antibody 2B6R (α-human IL5R) served as a negative control for flow cells 2 and 3 each of which contained 2000 RUs of immobilized CD4 and 17b respectively.

For kinetic analyses, typically 2000-3000 RUs of protein reagents are immobilized on SPR chips, and analytes are passed over the surface at 50-100 µL/min. Surface regeneration is achieved by a 5 µL injection of 10 mM HCl solution at 100 µL/min. Analysis of peptide-mediated inhibition of gp120 binding to sCD4 and mAb 17b is achieved by injecting a fixed concentration of HIV-1YU-2 gp120 (250 nM), with increasing peptide concentrations, over sCD4 (2000 RU) and mAb 17b (1000 RU) surfaces for 5 minute association and 5 minute dissociation at a flow rate of 50 µl min-1 in PBS. Regeneration of the surface is achieved by a single 10 second pulse of 1.3 M NaCl/35 mM NaOH and single 5-second pulse of 10 mM glycine, pH 1.5, for sCD4 and mAb 17b, respectively.

Data analysis of SPR competition data was performed using BIAevaluation v4.1.1 software (GE). To correct for nonspecific binding, response signals from buffer injection and from control flow cell were subtracted from all sensorgrams. Inhibition potencies were determined by calculating the inhibitor concentration required for 50% inhibition of maximal binding ($IC_{50}$). The inhibition curve was plotted and then fitted using the four-parameter equation as shown below using OriginPro 8 graphing software.

$$\text{Response} = R_{high} - \frac{(R_{high} - R_{low})}{1 + \left(\frac{Conc}{A_1}\right)^{A_2}} \quad (1)$$

where $R_{high}$ is the response value at high inhibitor concentrations and $R_{low}$ is response at low inhibitor concentrations. Conc. is the concentration of inhibitor, and $A_1$ and $A_2$ are fitting parameters. At the $IC_{50}$ the following is true:

$$\text{Response} = R_{high} - \frac{(R_{high} - R_{low})}{2} \quad (2)$$

Under this condition, $A_1$=Conc and is thus taken as the desired $IC_{50}$ parameter.

The cyclic peptides of the invention are tested against HIV-1 gp120 by SPR competition assays. A mixture of the cyclic peptide/gp120 solutions is passed over SPR chip immobilized with CD4 and 17b separately. The competition assay evaluates the ability of each peptide to inhibit the binding between gp120 and both soluble CD4 and 17b antibody, a surrogate for co-receptor. 29N-2 was found to be dual inhibitors of both CD4 and 17b binding to gp120.

Example 5: Binding Studies of cPTs 3 & 36 to Gp120 YU-2 Using ITC cPT dissociation constants were determined at 25° C. on a VP-Isothermal Titration calorimeter (VP-ITC) system (MicroCal™, GE Healthcare, Freiburg). 200 μM (for 36) or 390 μM (for 3) compound solutions were in 8 μL steps titrated into 30 μM of wild type gp120 YU-2 at 25° C. using 1×PBS buffer at pH 7.3. The resulting heat change upon injection was integrated over a time range of 300 sec, and the obtained values were fitted to a standard single-site binding model using ORIGIN®.

Example 6: Changing Stereocenters at Lys and Asp Centers

Figure 5:
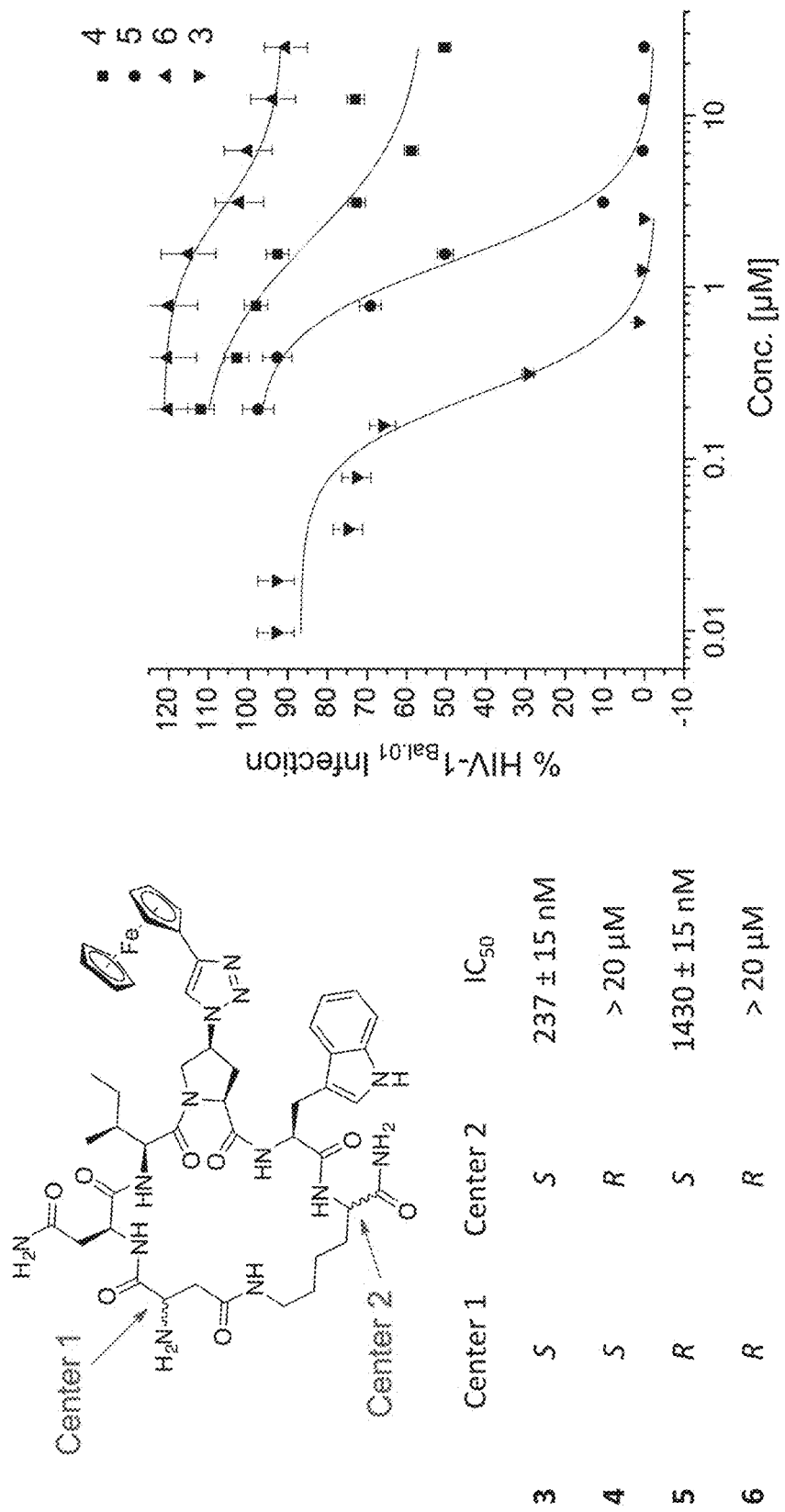
FIG. 5 illustrates structures and biological activities of cPTs with altered stereochemistry at the Asp and Lys chiral centers. Each cPT was synthesized starting from pure L- or D-amino acids. The cutoff used in the infection inhibition assay was 20 μM.

The stereocenters of the active core (Ile-triazoloPro-Trp) in the linear peptide triazoles have to be in the S configuration for optimal activity, whereas the R configuration can be tolerated only at the most N and C terminal residues. The effect of modifying the stereocenters at both the Asp and Lys residues, used for the cyclization, was investigated to determine whether changes of these positions could tune the activity. As shown in FIG. 5, the newly introduced R configuration can be tolerated only at the Asp chiral center (center 1, cPT 5), with 7-fold decrease in activity compared to the lead cPT 3. In contrast, changing the configuration of the Lys chiral center (center 2, cPT 4) from S to R had a more devastating effect (>50 fold decrease) on the activity. Therefore, the S configuration at both the Asp and Lys centers was judged to be optimal for cPT functions, though there is a degree of allowable tolerance at the Asp chiral center that can be an optimization point.

Figure 6:
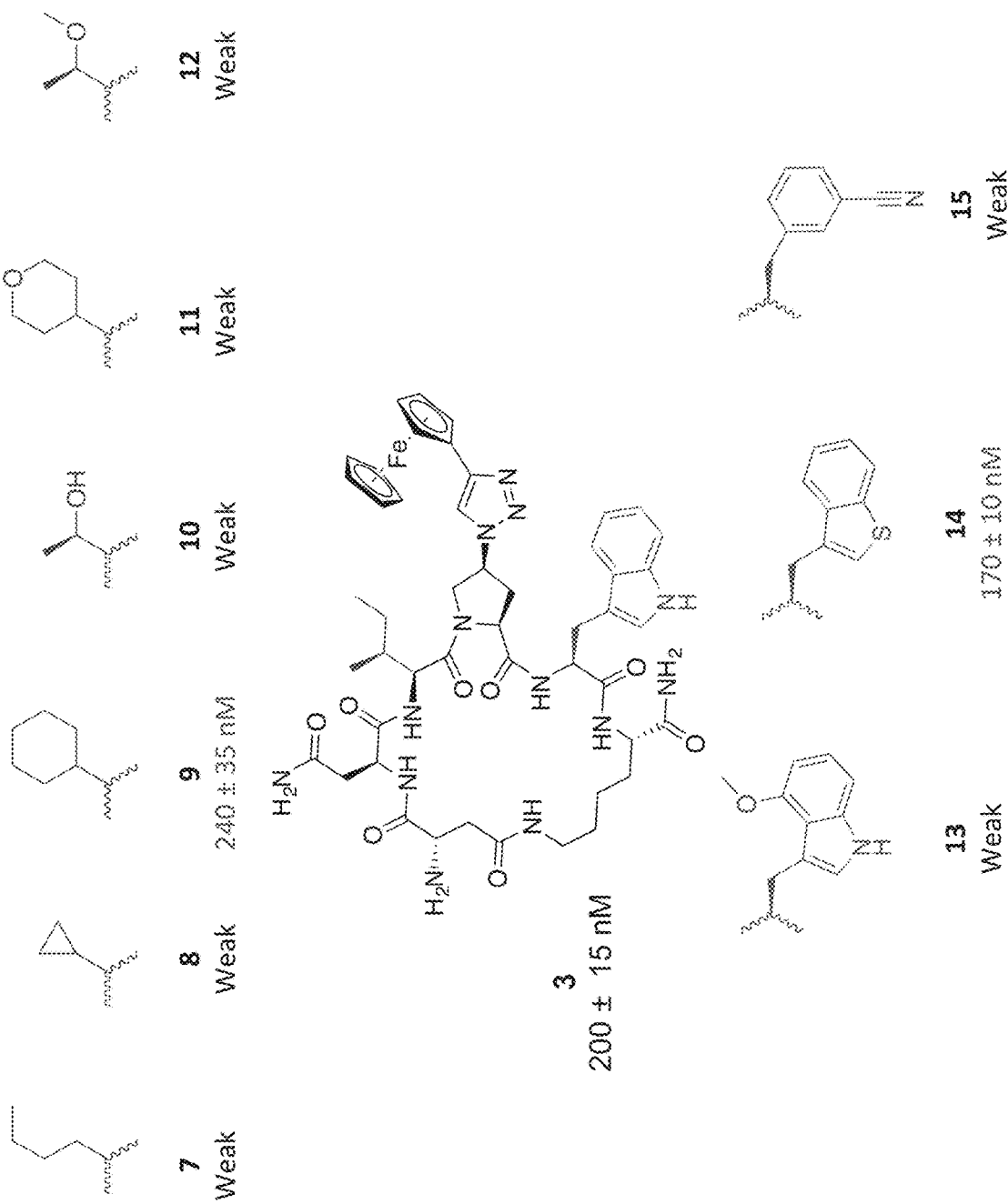
FIG. 6 illustrates structural changes in the indole and sec-butyl moieties of cPT. Activities shown are from HIV-$1_{Bal.01}$ infection inhibition assay. The designation weak means the compound showed weak inhibition (less than 50%) at 10 μM.

Example 7: Side Chain Variations (Ile Sec-Butyl and Trp Indole) in the Pharmacophore Region Non-natural replacements for the pharmacophore IXW, where X=aryl-triazole-Pro were investigated, with the non-limiting objectives of exploring the chemical space around this pharmacophore and/or identifying non-natural replacements that allow functionalization and derivatization at each pharmacophore site. FIG. 6 illustrates variations for both the indole and the sec-butyl side chains of the pharmacophore. The unsubstituted indole ring can be replaced with the isostere benzo[b]thiophene (14, $IC_{50}$~170 nM, FIG. 6). Additions on the indole ring with a methoxy group resulted in very weak activity (13, FIG. 6), indicating that this added group might prevent docking of the indole ring onto its target site on gp120 protein. The same weakening effect was also observed when benzonitrile, as an aromatic ring carrying a H-bond acceptor, was evaluated as a side chain (cPT 15). In certain non-limiting embodiments, unsubstituted indole and benzo[b]thiophene provide good activity at that pharmacophore site.

The Ile sec-butyl side chain was then explored. The branched nature of the sec-butyl group was found important where a methyl shuffle to the terminal carbon (7, FIG. 6) resulted in massive reduction in activity. A similar effect was observed when the two terminal methyl groups were tethered in a cyclopropyl form (8, FIG. 6). Without wishing to be limited by any theory, these weaker activities suggested that increasing the bulkiness/branching of the hydrocarbon at this position might improve the activity. The bulky cyclohexyl group showed retained activity (9, $IC_{50}$~240 nM, FIG. 6) compared to 3 ($IC_{50}$~ 237 nM). The effect of a polar group on this hydrophobic hydrocarbon was then investigated. In certain non-limiting embodiments, the hydrocarbon side chain can occupy a hydrophobic protein pocket, and an added electronegative atom may be able to abstract a H-bond from the protein backbone amide NHs, if they were close enough to the protein surface. In addition, adding a polar atom on these hydrocarbon groups might improve aqueous solubility. Adding an oxygen atom to the original sec-butyl side chain (as in 12, FIG. 6) and to the cyclohexyl (as in 11, FIG. 6) resulted in very weak activities. The same weakening effect also was observed when the sec-butyl group was changed to a smaller group containing unmasked OH group (10, FIG. 6). In certain embodiments, a conclusion from this polar atom addition is that increasing the total polar surface area (tPSA) of these hydrocarbon moieties at the sec-butyl position leads to a massive reduction in functions.

Example 8: Changes in the Aryl Group on the Triazole Moiety

Studies were performed to find alternatives for the ferrocene moiety, which affords good activities with both linear PTs as well as cPTs. As shown in Table 1, both commercially available alkynes and also synthesized additional key alkynes were used (Scheme 1) to identify triazole substituents that would enhance exploration of the chemical space on the triazole ring. The new triazole derivatives retained the dual host-cell receptor antagonism signature of the ferrocene-containing lead cPT 3 (Table 3).

T

TABLE 1-continued

Structure activity relationship around the triazole moiety.
A general structure is shown with the R group specified in the table,
each with the HIV-1$_{Bal.01}$ infection inhibition IC$_{50}$ value. Asterisk (*)
indicates that the cPT was made "in house" using a synthetic alkyne
that was incorporated in the click reaction during the cPT synthesis.

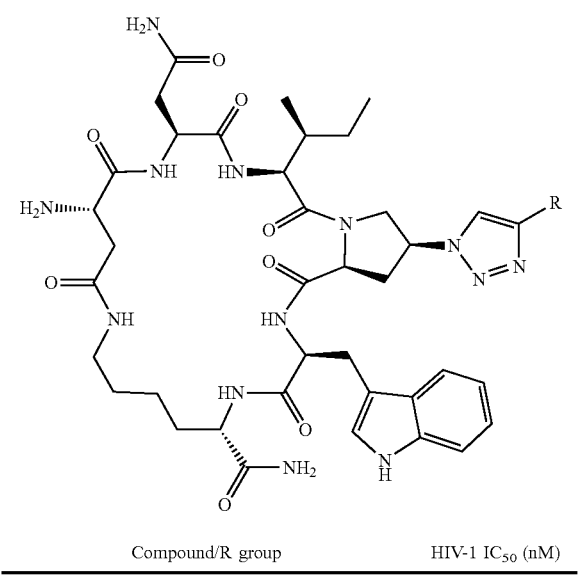

| Compound/R group | HIV-1 IC$_{50}$ (nM) |
|---|---|
| 18 | 1400 ± 200 |
| 19 | 438 ± 12 |
| 20 | 1200 ± 500 |
| 21 | 900 ± 45 |

TABLE 1-continued

Structure activity relationship around the triazole moiety.
A general structure is shown with the R group specified in the table,
each with the HIV-1$_{Bal.01}$ infection inhibition IC$_{50}$ value. Asterisk (*)
indicates that the cPT was made "in house" using a synthetic alkyne
that was incorporated in the click reaction during the cPT synthesis.

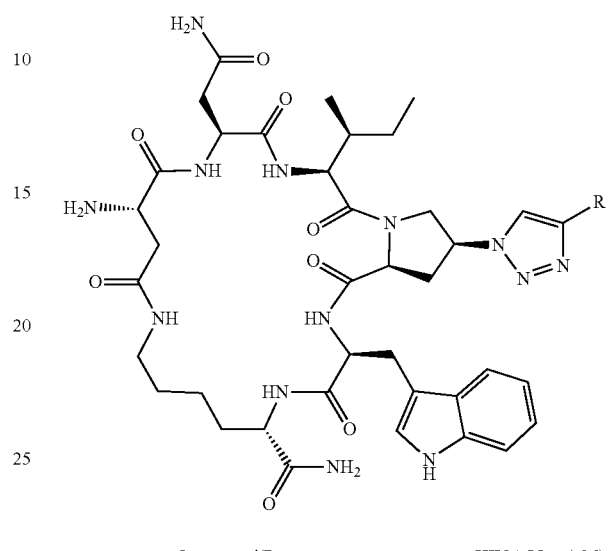

| Compound/R group | HIV-1 IC$_{50}$ (nM) |
|---|---|
| 22 | 350 ± 25 |
| 23 | 269 ± 32 |
| 24* | 180 ± 9 |
| 25* | 5100 ± 220 |

TABLE 1-continued

Structure activity relationship around the triazole moiety.
A general structure is shown with the R group specified in the table,
each with the HIV-1$_{Bal.01}$ infection inhibition IC$_{50}$ value. Asterisk (*)
indicates that the cPT was made "in house" using a synthetic alkyne
that was incorporated in the click reaction during the cPT synthesis.

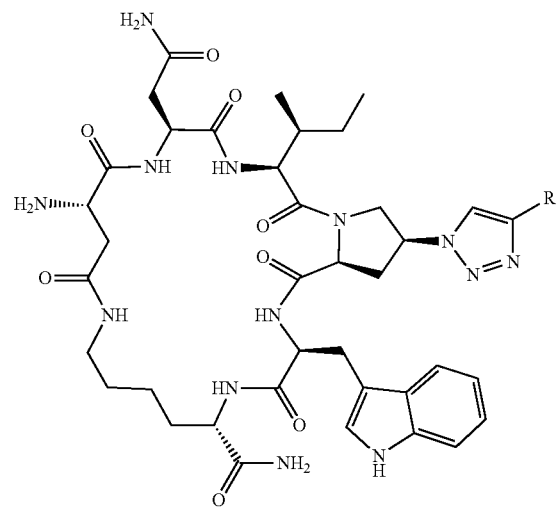

| Compound/R group | HIV-1 IC$_{50}$ (nM) |
|---|---|
| 26* 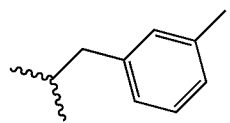 [SMILES: *Cc1cccc(C)c1] | 220 ± 42 |
| 27* 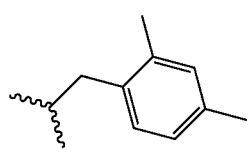 [SMILES: *Cc1ccc(C)cc1C] | 302 ± 50 |
| 28* 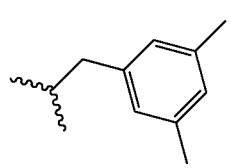 [SMILES: *Cc1cc(C)cc(C)c1] | 2000 ± 390 |
| 29* 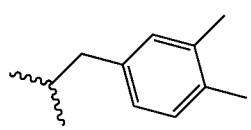 [SMILES: *Cc1ccc(C)c(C)c1] | 8000 ± 250 |

TABLE 1-continued

Structure activity relationship around the triazole moiety.
A general structure is shown with the R group specified in the table,
each with the HIV-1$_{Bal.01}$ infection inhibition IC$_{50}$ value. Asterisk (*)
indicates that the cPT was made "in house" using a synthetic alkyne
that was incorporated in the click reaction during the cPT synthesis.

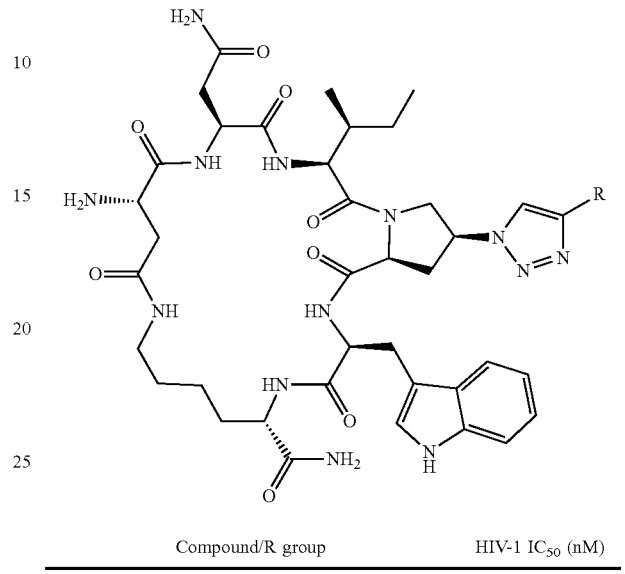

| Compound/R group | HIV-1 IC$_{50}$ (nM) |
|---|---|
| 30 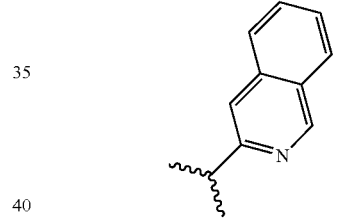 | 5000 ± 850 |
| 31  | 1800 ± 500 |
| 32*  | 7300 ± 740 |
| 33*  | 6000 ± 450 |

Several alkynes were synthesized starting from the commercially available benzyl bromides (Scheme 1). The prepared alkynes were relatively unstable and hence were utilized immediately for synthesizing cPTs (Table 1).

Scheme 1. Chemical synthesis of alkynes a9-a16

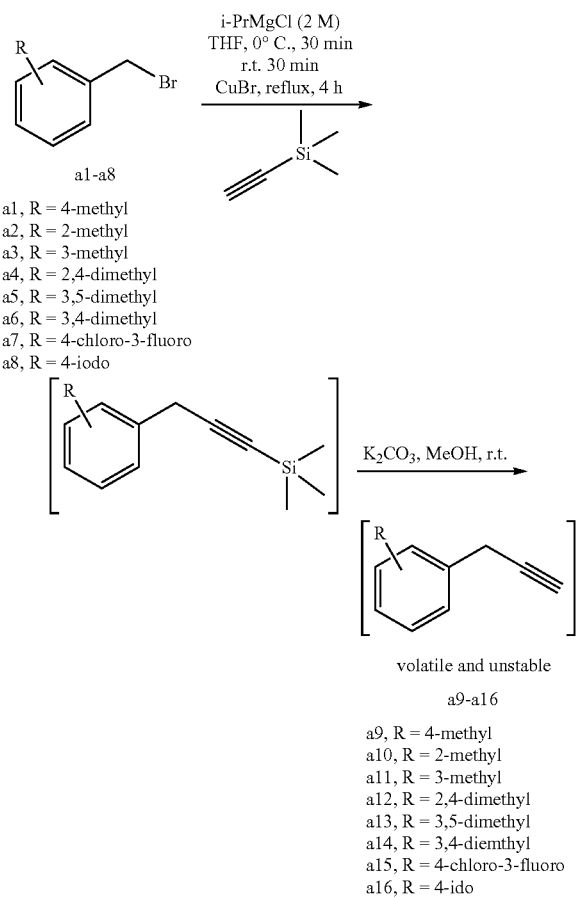

Final alkynes were volatile and unstable, and were used immediately for the click reaction with the resin-bound azido-cPT to produce the triazole variant denoted "*" in Table 1.

Example 9: Structure Activity Relationship (SAR) of the Triazole Variant

The HIV-1 cell infection inhibition activities of the new triazole derivatives were evaluated (Table 1 and FIG. 6). The hydrophobicity and aromaticity of the R group on the triazole ring were found to be important, as well as the spacing atoms between the triazole and the aryl group. Using the basic N-methyl imidazole in cPT 17 gave the only triazole derivative was completely inactive. Comparing cPT 16 and 20, bringing the phenyl closer to the triazole ring slightly improved the activity ($IC_{50}$~1.2 μM for 20 compared to $IC_{50}$~2 μM for 16). Building up on 20 by adding extra methyl group(s) further improved the activity as shown for the isopropyl group (21, $IC_{50}$~0.9 μM) and the tert-butyl group (22, $IC_{50}$~0.35 μM). This observation indicated the importance of increasing the bulkiness at the para-position of the phenyl ring. Replacing the tert-butyl group (in 22) with a phenyl group further confirmed this hypothesis, where the biphenyl containing cPT 23 exhibited an $IC_{50}$ value of 269 nM. Introducing a bulky, non-aromatic moiety resulted in an active cPT (18, $IC_{50}$~1.3 μM), though less active than the aromatic biphenyl system (23).

The isoquinoline moiety was also investigated (30, $IC_{50}$~5 μM), which was not as active as the biphenyl system (23). The phenyl methyl moiety was also evaluated (in 19). The activity improved ($IC_{50}$~438 nM for 19) compared to the two-spacer atoms (as in 16) and the directly attached phenyl (as in 20). This enhanced potency indicated the importance of a single spacer atom in directing the phenyl ring to an optimal position. As shown in Scheme 1, a series of alkynes were prepared to investigate the SAR around the phenyl of 19. Introducing an electron donating methyl group at the para-position further improved potency (24, $IC_{50}$~180 nM versus $IC_{50}$~438 nM for 19). A methyl shuffle from the para-position to the meta-position was well tolerated (26, $IC_{50}$~220 nM). However, when introduced at the ortho-position, activity was greatly decreased (25, $IC_{50}$~5.1 μM, about 28-fold lower potency compared to 24). Adding a para-methyl group to 25 restored the activity (27, $IC_{50}$~302 nM). Without wishing to be limited by any theory, this added para-methyl can have enabled a contact with a hot spot on gp120 that was not reached in the case of 25. A combination of either para-methyl and meta-methyl groups (in 29) or two meta-methyl groups (in 28) resulted in decreased anti-HIV activity (8 μM for 29 and 2 μM for 28). These results argue that increasing the bulkiness around the closer sides of the para-position may have negative effects on correctly positioning the phenyl ring on its target site on the gp120 protein, though addition of methyl far from the para-position could be tolerated (ortho-position as in 27). Introducing electron-withdrawing halogens on the phenyl ring of 19 resulted in decreased activities (31 with $IC_{50}$~1.8 μM, 32 with $IC_{50}$~7.3 μM and 33 with $IC_{50}$~6 μM). Without wishing to be limited by any theory, the electron-withdrawing nature of the halogens may have reduced the electron density, on the phenyl ring, which may be required for essential π-π interactions with gp120 residues.

Figure 7:
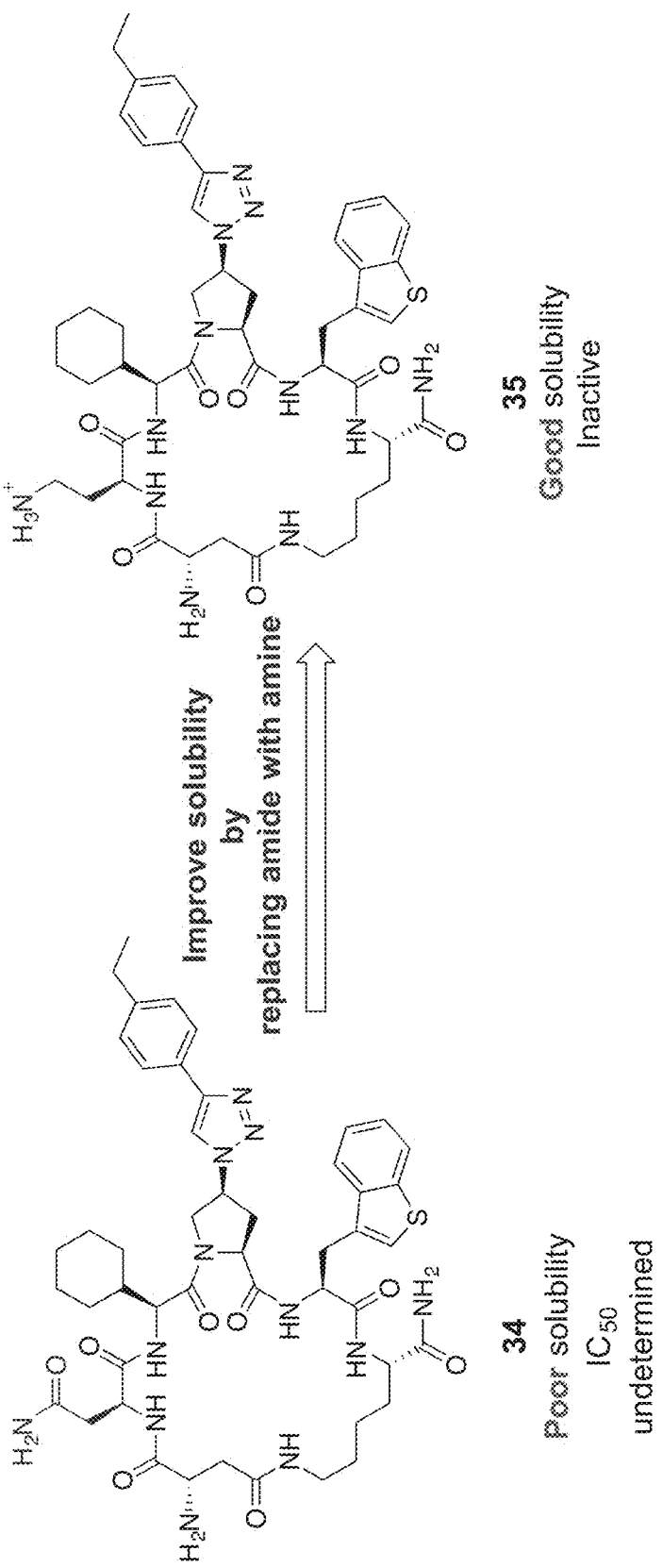
FIG. 7 illustrates certain modifications in cPT scaffold to improve solubility of cPT 34. Each cPT was synthesized starting from the corresponding amino acids: Asn for 34 and Dab for 35. Designation of "poor" and "good" solubility was based on behavior of cPT in PBS buffer or PBS buffer with 5% DMSO.
Figure 8A:
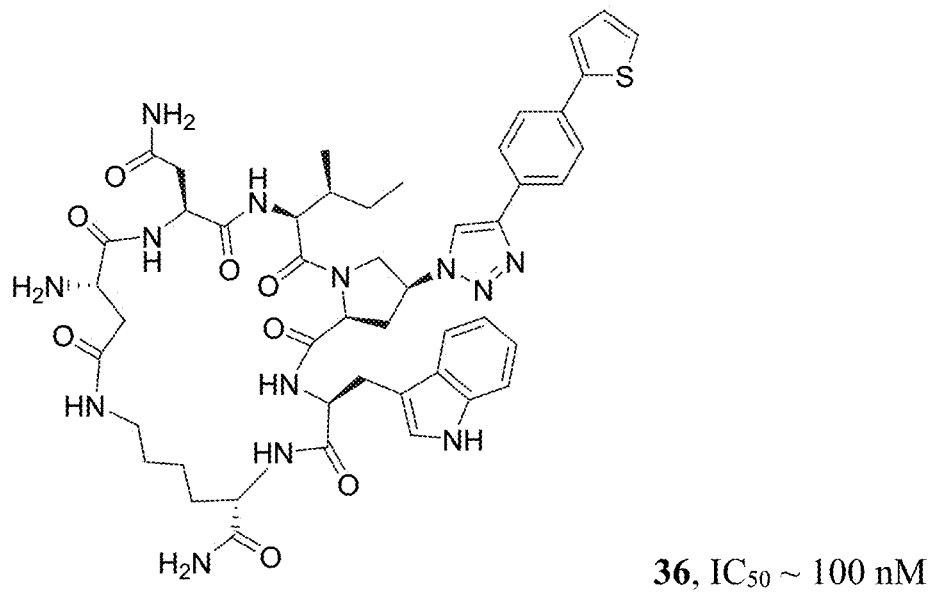
FIGS. 8A-8F illustrate structures and functional properties of cPTs 36 (FIG. 8A) & 37 (FIG. 8B).
Figure 8B:
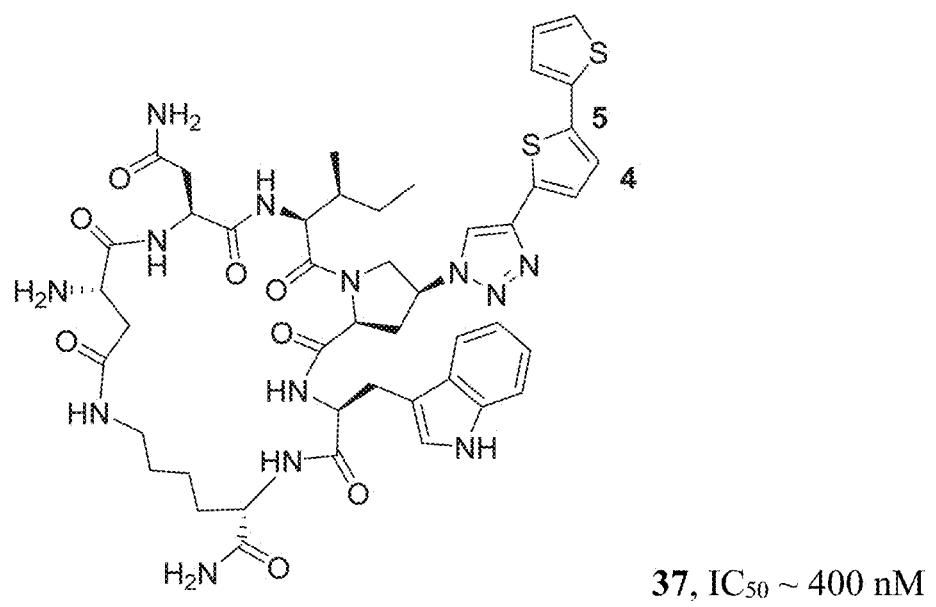
Figure 8C:
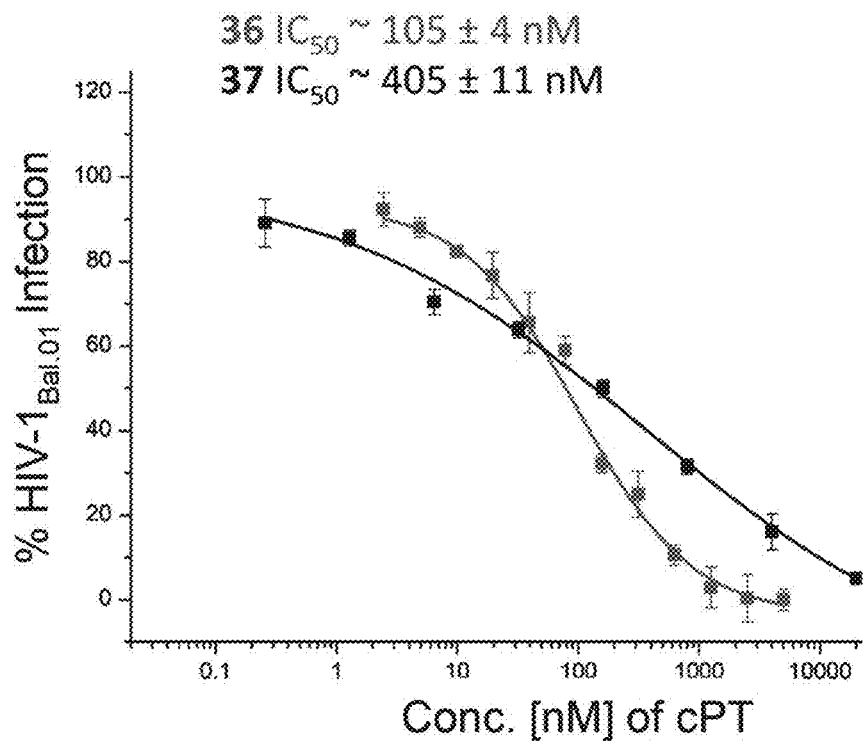
Figure 8D:
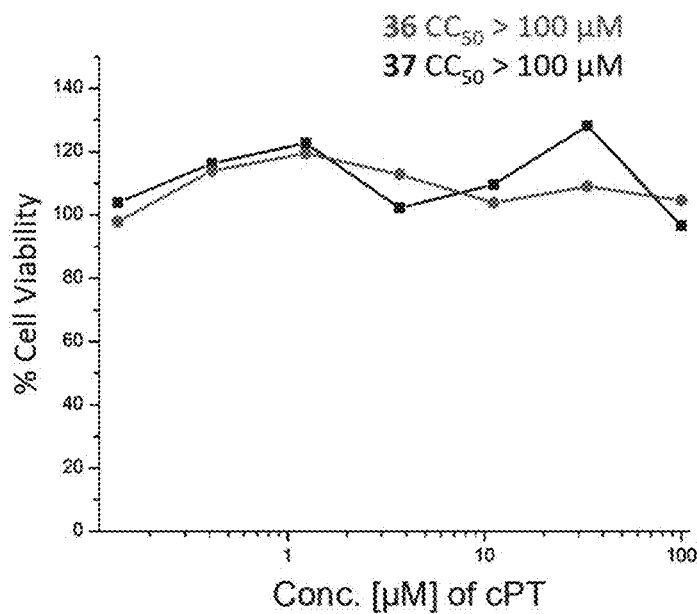
Figure 8E:
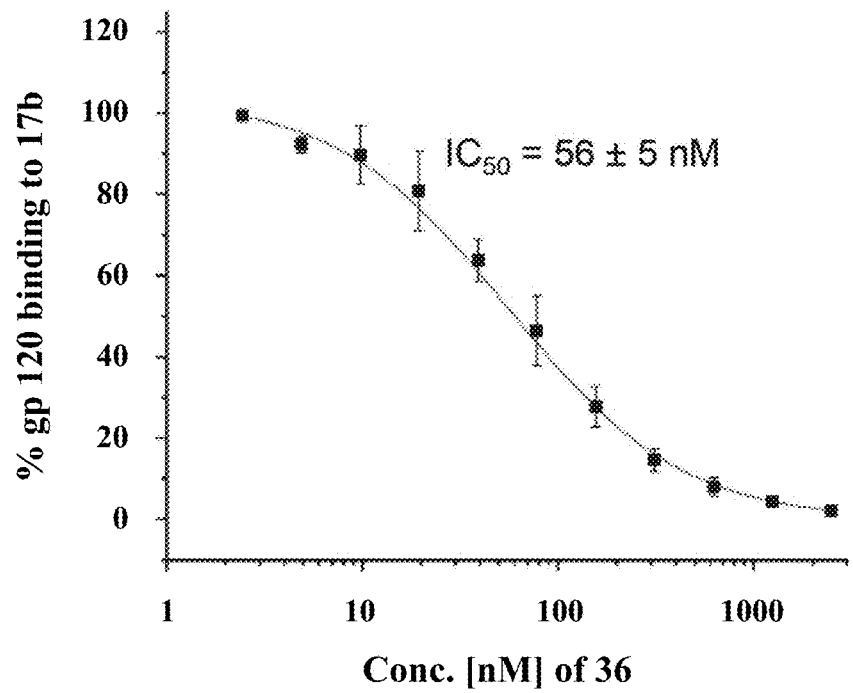
Figure 8F:
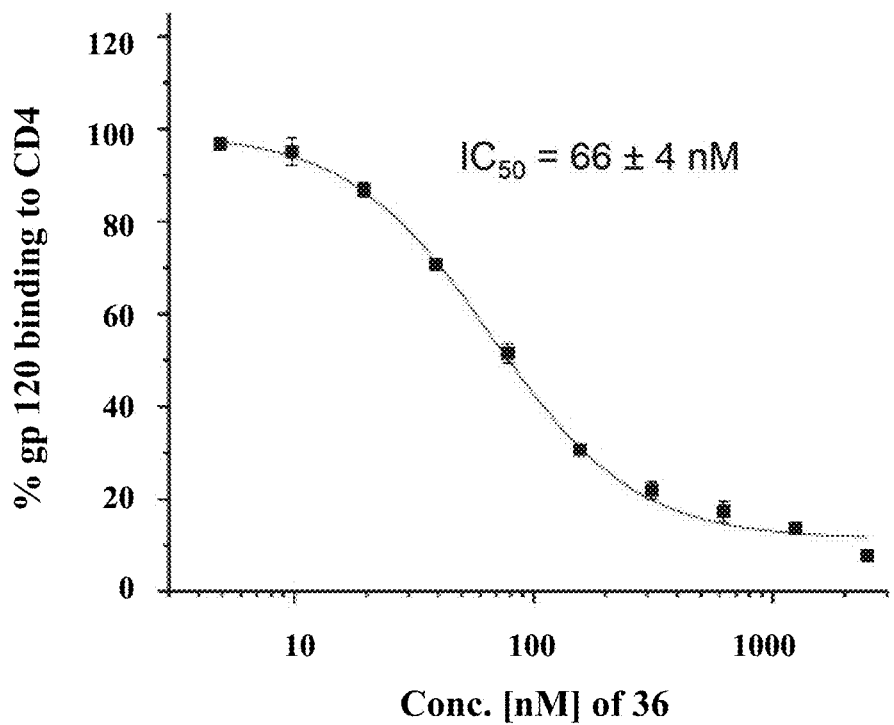

Based on the above-described variations (FIG. 6 and Table 1), it was envisioned that a combination of the pharmacophore side chain substituents would enhance the potency. cPT 34, with benzo[b]thiophene, cyclohexyl and ethyl-phenyl moieties as hydrophobic groups was synthesized (FIG. 7) to evaluate the activity of these combined variations. However, this cPT variant had poor solubility, and $IC_{50}$ determination was challenging because of precipitation problems during the infection inhibition assay. In an attempt to increase the aqueous solubility of 34, 35 (FIG. 7) was synthesized in which the amide side chain of Asn was replaced with an amine using a Dab amino acid during the cPT synthesis. As expected, 35 had better solubility because of the newly introduced amino group. However this cPT was found to be inactive. Without wishing to be limited by any theory, this indicates the importance of the amide functionality of the Asn residue or the unfavored positioning of the positively charged amine functionality within gp120.

Example 10: On-Resin Synthesis of Bi-Aryl Containing cPT

Based on the observation that the bi-phenyl containing cPT 23 (Table 1) has a comparable potency ($IC_{50}$ value of 269 nM) to the parent ferrocene containing cPT 3 ($IC_{50}$ value of 237 nM), the bi-aryl system was explored as a potential activity-tuning moiety. A facile on-resin microwave-assisted synthetic pathway was designed to allow exploring different bi-aryl systems (Scheme 2). Briefly, after assembling the cPT sequence and on-resin cyclization, click reaction with the bromo-alkyne was achieved. The bromine handle was then used for an on-resin cross-coupling reaction using a boronic acid in presence of a palladium catalyst and a base. Mild reaction conditions were enough to achieve the complete formation of the bi-aryl system (Scheme 2). Replacing the terminal phenyl ring of 23 (Table 1, IC$_{50}$ value of 269 nM) with its isostere thiophene ring resulted in >2-fold improvement in potency (36, IC$_{50}$ value of 105 nM, FIG. 8). This suggests, in certain embodiments, that the lipophilic nature of the aryl moiety in this part of the molecule is important for the activity. SPR competition assays showed that the newly derived thiophene-phenyl system retained the dual host-cell receptor antagonism signature of cPTs: 36 inhibited gp120 binding to both CD4 and 17b, the latter used as a co-receptor surrogate (FIG. 8). However, replacing the middle phenyl ring (between the triazole and the thiophene of 36) with another thiophene ring (a bi-thiophene containing cPT 37) resulted in reduced activity (IC$_{50}$ value of 405 nM for 37). Without wishing to be limited by any theory, this change in activity can be related to the change in the orientation of the long arm triazole-thiophene-thiophene relative to the gp120-binding site. In this view, the terminal thiophene of 37 installed in position 4 of the middle thiophene (FIG. 8) could have resulted in slight bending of this long triazole arm compared to the straight arm in 36. Cell viability was assessed for 36 and 37; no cytotoxicity was detected at the highest concentrations used (100 μM, FIG. 8). Therefore, the selectivity index (SI) for 36 can be estimated to be >>1000 based on the IC$_{50}$ and the CC$_{50}$ values, indicating a good cellular safety profile for this compound.

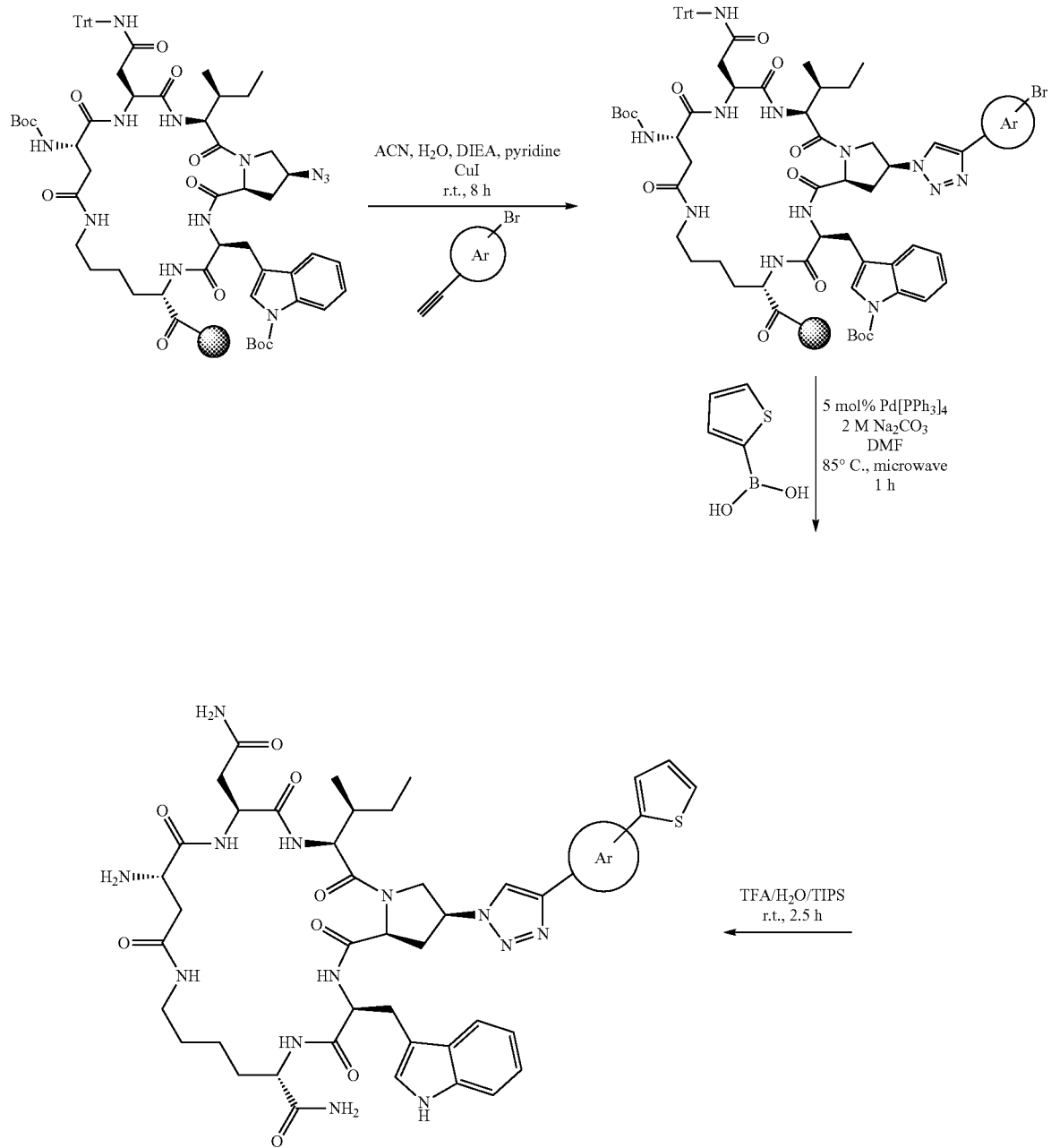

Scheme 2. On-resin synthesis of the bi-aryl system on cPT

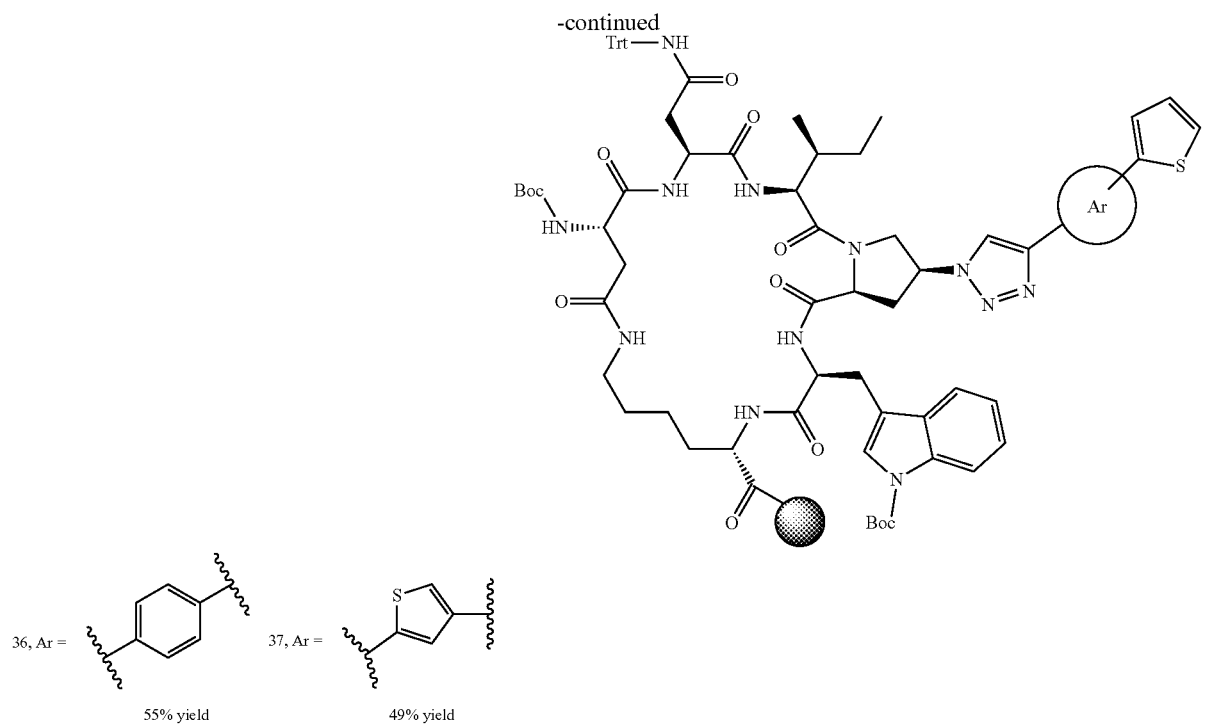

Example 11: Isothermal Titration Calorimetry (ITC) of 3 Versus 36

Figure 9A:
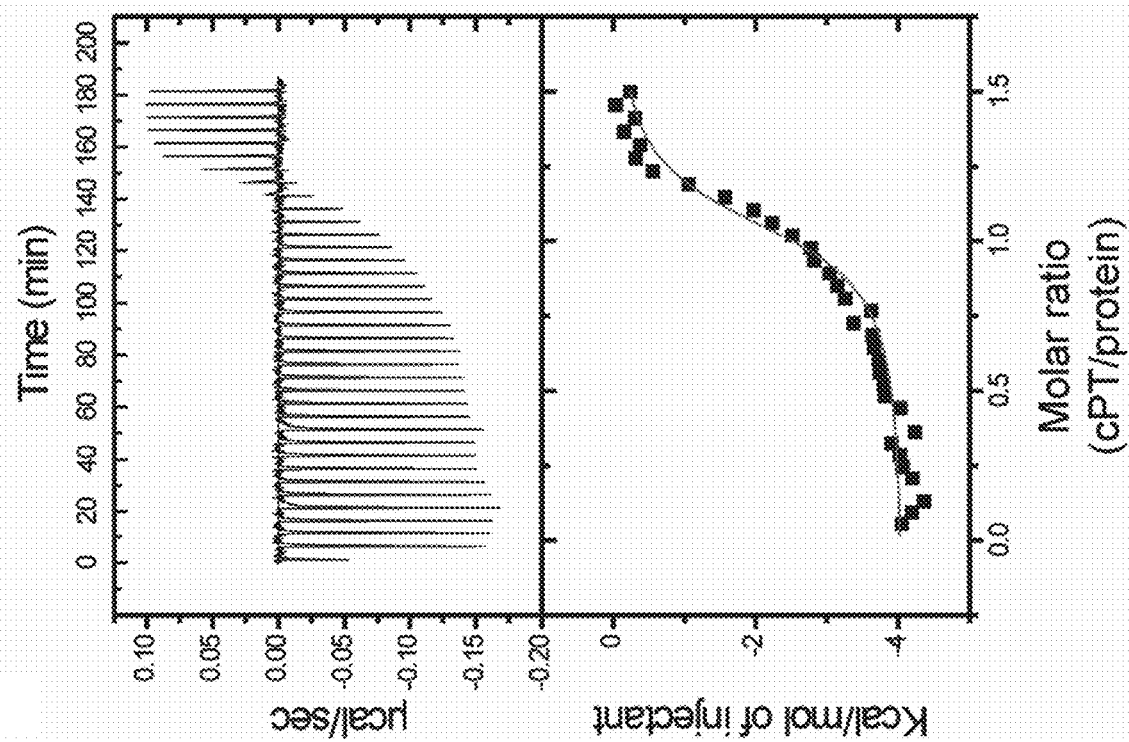
FIGS. 9A-9C illustrate cPT binding and thermodynamic profile of monomeric wild type gp120 YU-2 for cPTs 3 (FIGS. 9A and 9C) and 36 (FIGS. 9B and 9C). Compound solution, 390 µM (for 3) or 200 µM (for 36), was titrated in 8 µL steps into 30 µM of YU2 full-length gp120 at 25° C. in the reaction chamber of a VP-ITC instrument using 1×PBS buffer at pH 7.3. The resulting heat changes were integrated, and the values obtained were fitted to a quadratic binding equation (one site binding model). The following $K_D$ and thermodynamic values were derived: 3 (FIGS. 9A and 9C): $K_D$=415±98 nM, n=1.06±0.02, ΔH=−5.96±0.13 kcal/mol, ΔS=9.22 cal/mol; 36 (FIGS. 9B and 9C): $K_D$=350±62 nM, n=1.06±0.01, ΔH=−4.07±0.06 kcal/mol, ΔS=15.9 cal/mol.
Figure 9B:
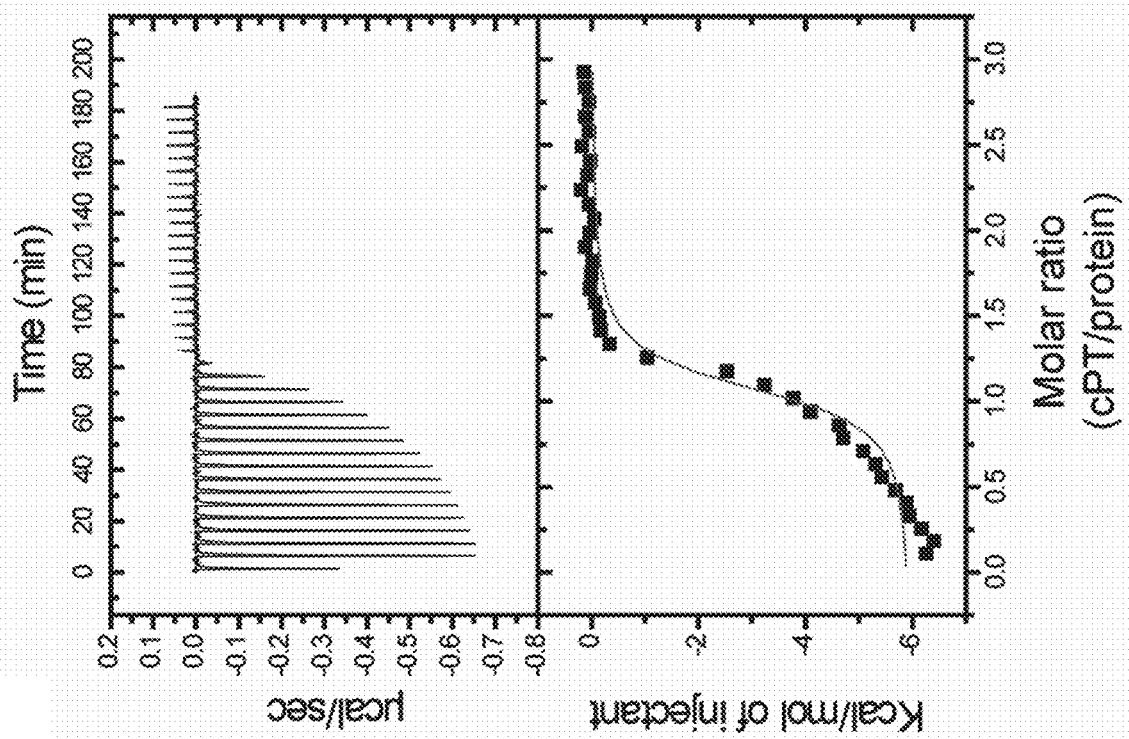
Figure 9C:
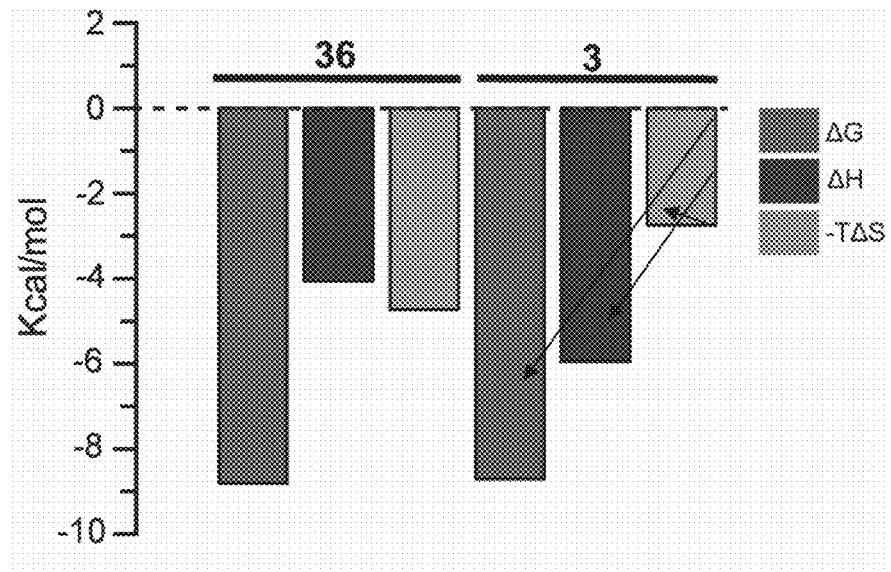

To better explain the differences in antiviral potencies between cPTs 3 and 36, their binding affinities and thermodynamic profiles were determined by isothermal titration calorimetry (ITC). Binding was measured in the monomeric gp120-YU-2 context. Glycoprotein gp120 YU-2 bound 3 with an affinity of 415 nM and a stoichiometry of one cPT per gp120 molecule (FIG. 9A). The binding mode was mainly enthalpy driven, with a ΔH value of −5.96 kcal/mol (FIG. 9C). The new cPT 36 showed improved binding affinity with dissociation constant of 350 nM and was bound by one gp120 molecule, comparable to 3 in the binding comparison (FIG. 9B). The thermodynamic profile of 36 indicated a slight increase towards an entropically favored (−TΔS=−4.74 kcal/mol) binding mechanism compared to 3 (−TΔS=−2.75 kcal/mol, FIG. 9C). The effect of peptide cyclization can be observed in the thermodynamic signature by comparing cPTs and PTs. In this study, both 3 and 36 showed positive ΔS values, suggesting an entropically favored binding mechanism. In contrast, the thermodynamic signature for linear PTs previously showed negative ΔS values, reflecting a large unfavorable entropy change.

Example 12: Binding Model of 36 with HIV-1 Env Gp120 Unit (Pdb: 5FUU)

PTs and cPTs bind to an inactive state of the conformationally dynamic HIV-1 Env that lacks a formed bridging sheet, possibly by inserting a hydrophobic part of the molecule under the $\beta_{20/21}$ loop of the bridging sheet. To investigate the binding mode of new cPT 36 with the dynamic HIV-1 Env gp120, Glide InducedFit Extended Sampling was used to allow flexibility of the protein at the active site. Multiple conformers of 36 were generated (Schrödinger Macrocycle Conformational Sampling) and clustered using heavy atoms. This yielded 30 clusters, for each of which one conformer was selected as a cluster representative. The 30 cluster representatives were docked (using Schrödinger InducedFit Extended Sampling), and the returning pose/protein complexes were sorted according to their Glide gscores. Examination of the top scored poses was based on the selection criteria (Table 2) that were extracted from structure activity relationships in prior work as well as from the current study.

Figure 10:
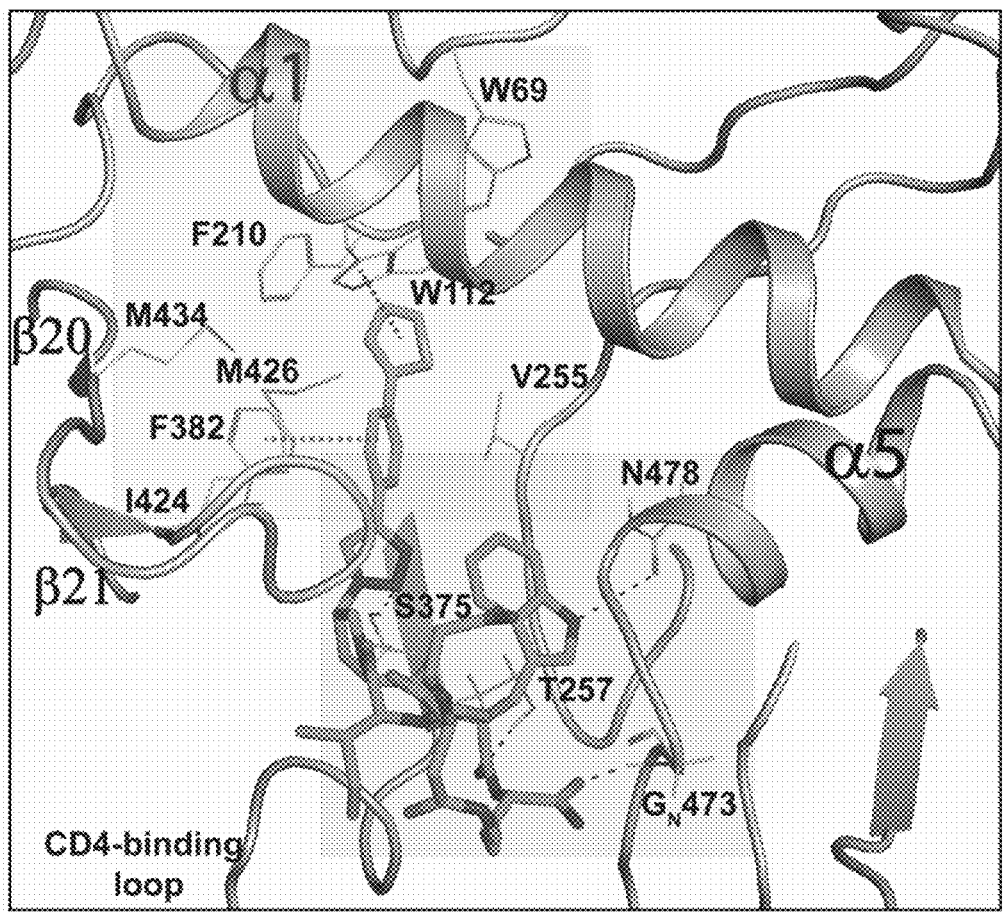
FIG. 10 illustrates putative binding pose 4 (from Table 2) of cPT 36 docked onto gp120 from the pdb 5FUU. cPT 36 is shown in cyan sticks, H-bonds are shown as black dashed lines, and π-π stacking interactions are shown in red dashed lines.
Figure 11:
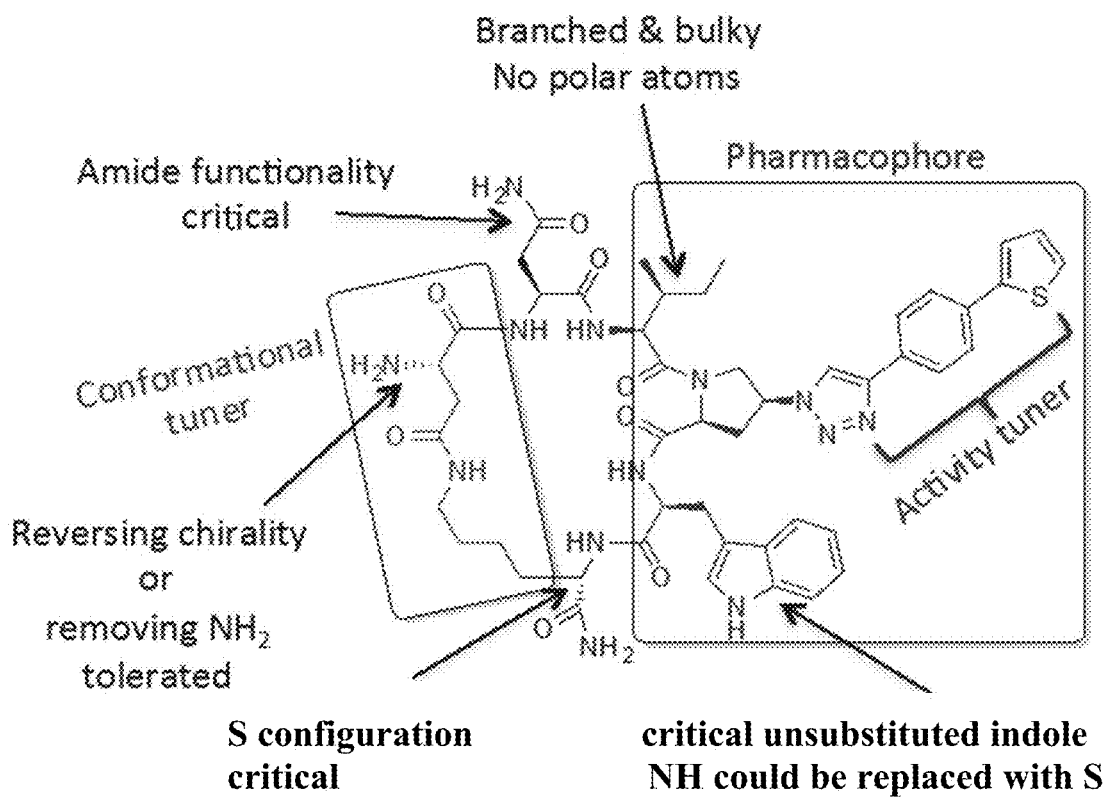
FIG. 11 illustrates overall structure activity relationship of cPTs depicted with cPT 36. Molecular properties of 36 were calculated using MarvinSketch software (version 15.11.9.0, 2015, ChemAxon, www dot chemaxon dot com).
Figure 12:
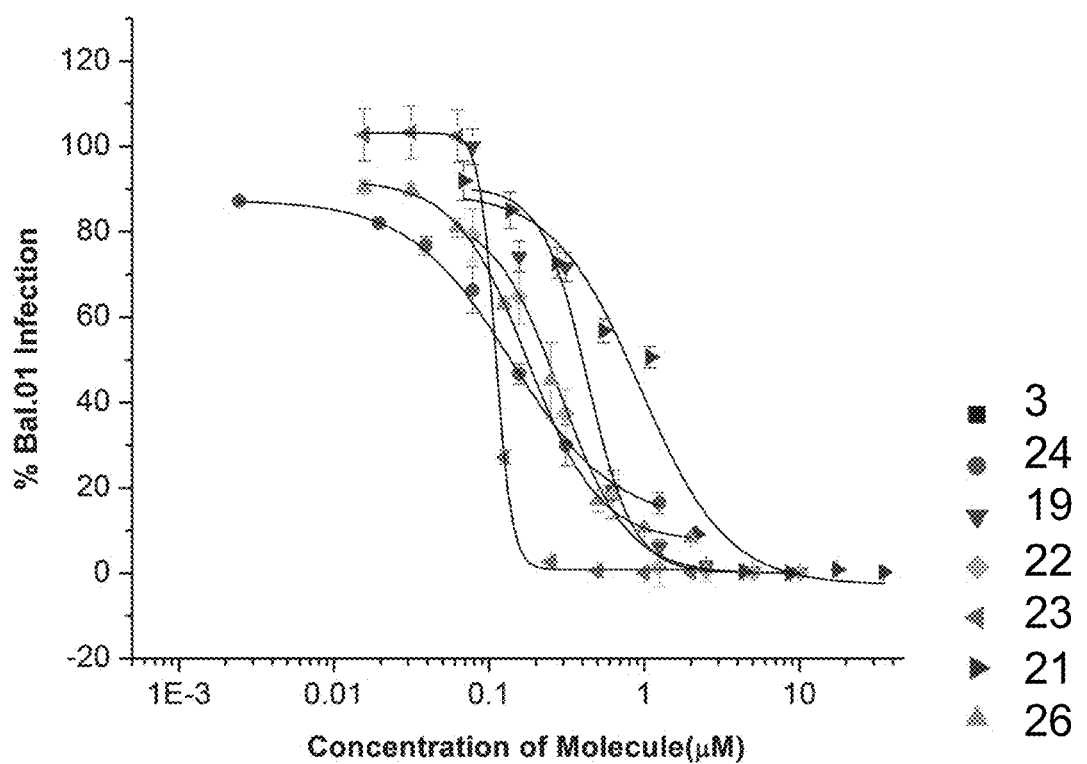
FIG. 12 comprises HIV-1$_{Bal.01}$ cell infection inhibition curves by representative new triazole derivatives listed in Table 1.

The first pose that meets all the selection criteria (pose 4 from Table 2) was selected as a representative putative binding mode (FIG. 10) for 36 within gp120. The overall ligand-protein interaction energy for this pose was calculated using SZYBKI (v1.8.0.1: OpenEye Scientific Software, Santa Fe, N M. www dot eyes open dot com) and found to be −27.13 kcal/mol, indicating high stability within this binding conformation. The newly introduced thiophene-phenyl on the triazole nicely penetrates through the pre-identified sub-site 2 within gp120 located under the al-helix and B20/21 loop (yellow shading in FIG. 10), and the Trp indole buries itself in sub-site 1 in proximity to residue Thr257 and the α5-helix residue Asn478 (light blue shading in FIG. 10). The bi-aromatic system stabilizes itself in the gp120 pocket through two possible T-shaped and edge-to-face stacking interactions. The thiophene stacks to the important residue Trp112 indole ring, whereas the phenyl (between the triazole and thiophene) stacks with residue Phe382 (FIG. 10). Without wishing to be limited by any theory, such interactions could be the reason for activity retention by the bi-aryl systems comparable to the bulkier ferrocene moiety. The putative model also shows the sec-butyl moiety of the cPT-Ile buried between the β20/21 loop and the CD4 binding loop (FIG. 10). This finding might explain the importance of this branched/bulky moiety compared to less branched or tethered moieties (FIG. 6). In addition, this model is consistent with the finding that adding polar atoms to this cPT-Ile side chain moiety/substituent would cause solvation of this part of the molecule, therefore could be pulling the molecule out into the solvent and preventing the proper docking onto the active site.

TABLE 2

Selection criteria of a putative binding pose of B with gp120 (pdb code 5FUU).

| | Glide gscore | Trp/Ile/ aryl- triazoloPro buried | C terminal amide exposed | N terminal amine exposed | Contact with Thr257/Ser37 5 cluster* | Contact with Trp112 cluster* |
|---|---|---|---|---|---|---|
| Pose 1 | −15.494 | Y☐☐ | No | Yes | Yes | Yes |
| Pose 2 | −14.388 | Yes | No | No | Yes | Yes |
| Pose 3 | −13.938 | Yes | No | Yes | Yes | Yes |
| Pose 4 | −13.741 | Yes | Yes | Yes | Yes | Yes |

*Areja, et al., 2015, J. Med. Chem. 58:3843-3858
"Yes" marks mean that the pose fits the criterion, (No" marks mean that the pose does not fit the criterion.
Pose 4 was the first pose to meet all criteria.

Example 13: Effect of Removing of the Primary Amine Group from 36

The above-described model (FIG. 10) showed that the N terminal of 36 is solvent exposed. Removal of this primary $NH_2$ from the cPT scaffold was investigated. This would allow exploring the importance of this part of the scaffold, which acts as a connecting bridge to the important cPT pharmacophore. Additionally, this $NH_2$ removal would reduce the total polar surface area of the scaffold and increase the lipophilicity. Controlled lipophilicity could be a step towards optimizing the scaffold for enhanced oral bioavailability.

Figure 13:
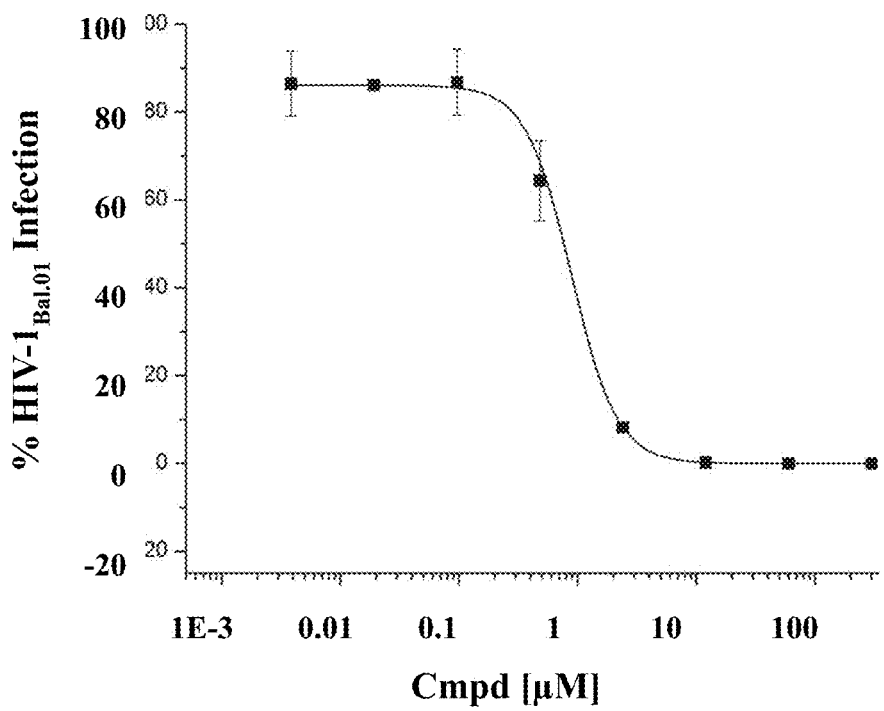
FIG. 13 comprises a HIV-1$_{Bal.01}$ cell infection inhibition curve by cPT 38. IC$_{50}$=882±44 nM.
Figure 13:
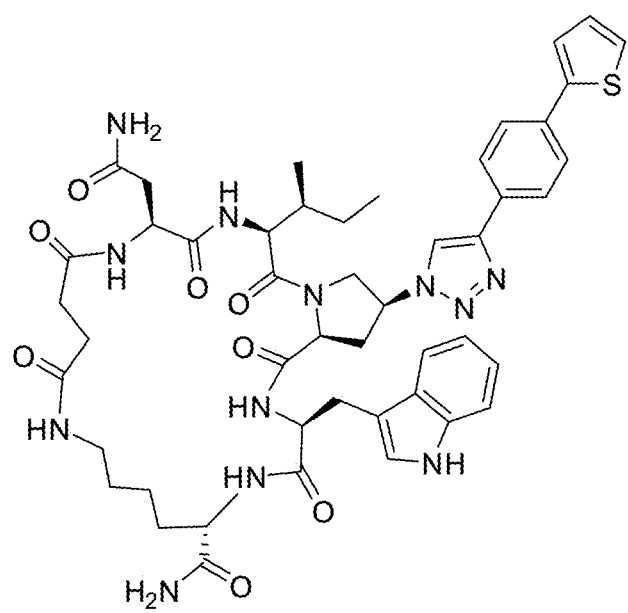

A synthetic route to achieve the cyclization was designed using a non-chiral, $NH_2$-free linker (Scheme 3). The cyclization intermediate 4-((9H-fluoren-9-yl) methoxy)-4-oxobutanoic acid (a19) was synthesized starting from 9-fluorenylmethanol (FmOH, a17) and succinic anhydride (a18). The resultant cPT 38 showed HIV-1 $IC_{50}$ value of ~882±44 nM (FIG. 13), with about 8-fold decrease in potency compared to the $NH_2$-containing analogue 36 ($IC_{50}$~100 nM). This 8-fold decrease in potency is comparable to that observed with changing the chirality of the Asp residue in cPT 5 from the S to R configuration (FIG. 5). Without wishing to be limited by any theory, this potency decrease could therefore be related to disturbing the cPT conformation. In this view, losing the chirality by removing the $NH_2$ results in more flexibility, and therefore a less ordered conformation of cPTs, leading to decreased potency. As expected by the binding model, the role of $NH_2$ in interaction with gp120 could then be ruled out. This amino terminal can in certain instances be extended through amide bond formation with additional residues without potency decrease.

Scheme 3. Synthesis of the cPT 38, with no free amine group

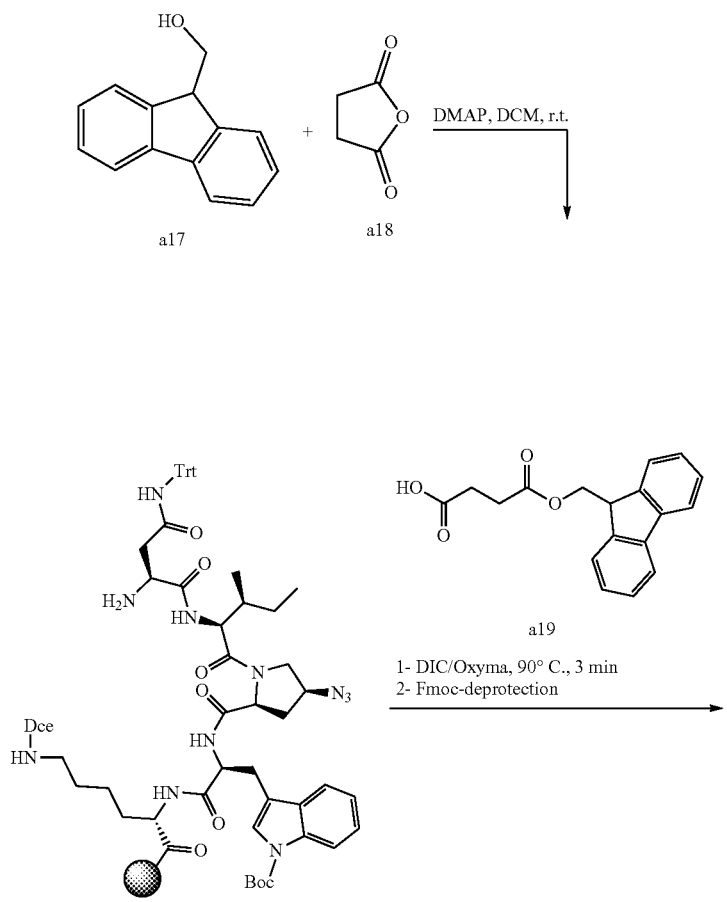

63
64
-continued
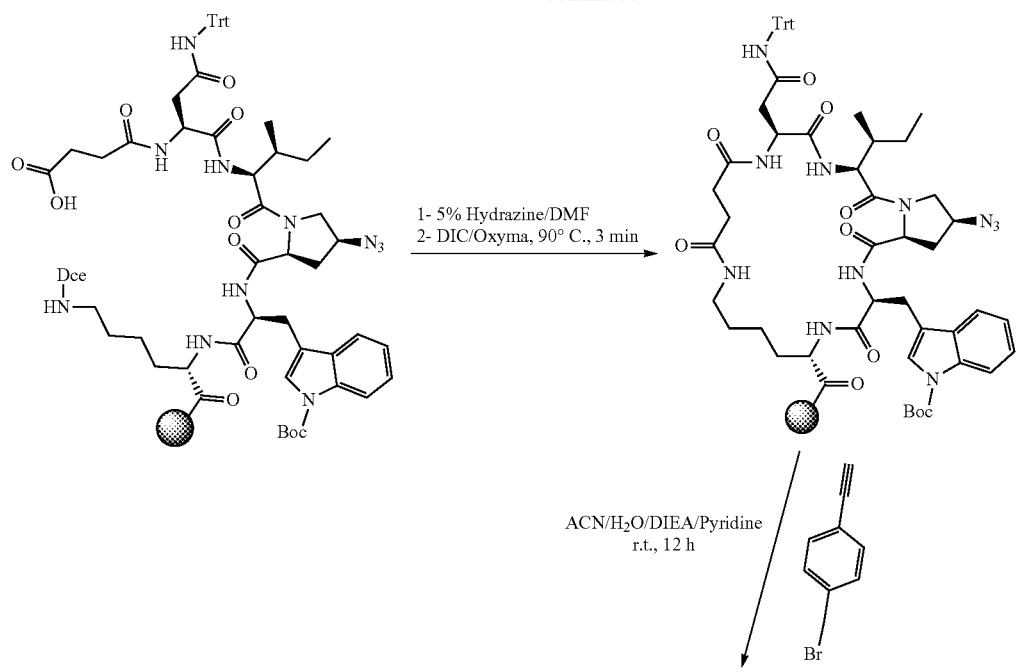
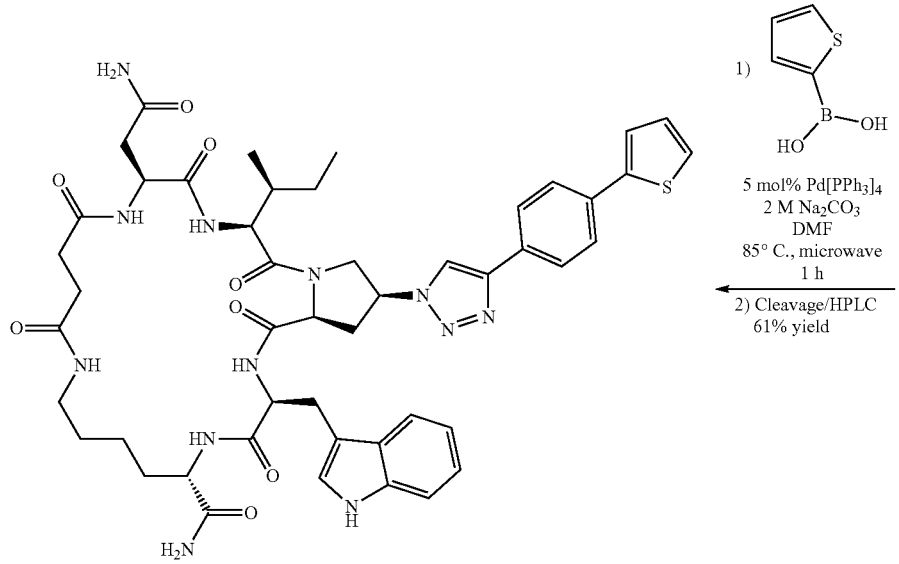
38, HIV-1$_{BAL01}$ IC$_{50}$ ~ 882nM

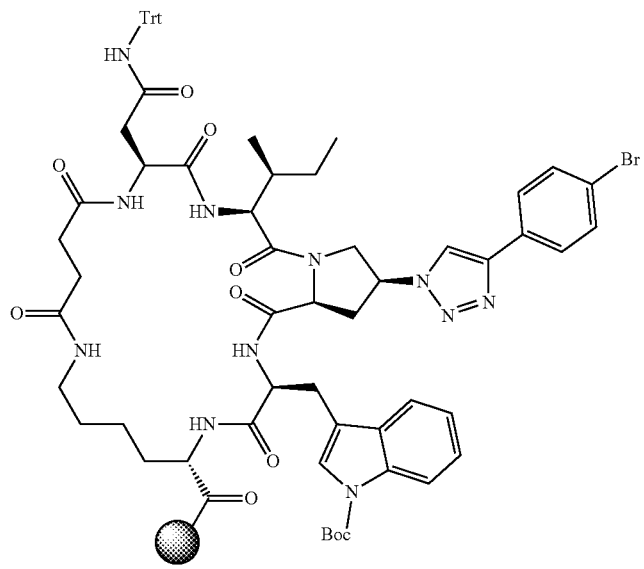

The cyclization linker a19 (shown in blue) was synthesized using FmOH (a17) and succinic anhydride (a18)[43] and was incorporated in the cPT synthesis.

TABLE 3

Dual host-cell receptor antagonism signature of representative new triazole derivatives.

| Compound | CD4 competition IC$_{50}$ (nM) | 17b competition IC$_{50}$ (nM) |
|---|---|---|
| 18 | 614 ± 31 | 647 ± 31 |
| 19 | 257 ± 5 | 269 ± 14 |
| 20 | 956 ± 61 | 820 ± 61 |
| 21 | 1200 ± 200 | 1260 ± 220 |
| 22 | 150 ± 20 | 120 ± 18 |
| 23 | 680 ± 33 | 720 ± 28 |
| 24 | 80 ± 12 | 74 ± 17 |
| 25 | 132 ± 22 | 128 ± 14 |
| 26 | 234 ± 14 | 228 ± 10 |
| 27 | 130 ± 11 | 136 ± 20 |
| 28 | 926 ± 13 | 918 ± 11 |
| 29 | 2800 ± 320 | 2600 ± 280 |

TABLE 4

Mass validation of the synthesized cPTs.

| Compound | Expected mass | Found mass |
|---|---|---|
| 3 | 1003.41 | 1003.55 |
| 4 | 1003.41 | 1003.33 |
| 5 | 1003.41 | 1003.42 |
| 6 | 1003.41 | 1003.50 |
| 7 | 1003.41 | 1003.40 |
| 8 | 987.83 | 987.75 |
| 9 | 1029.98 | 1030.47 |
| 10 | 991.89 | 990.50 |
| 11 | 1031.95 | 1031.94 |
| 12 | 1005.39 | 1005.27 |
| 13 | 1033.42 | 1033.48 |
| 14 | 1020.99 | 1020.42 |
| 15 | 989.92 | 990.17 |
| 16 | 924.08 | 924.17 |
| 17 | 900.01 | 900.67 |
| 18 | 954.15 | 955.17 |
| 19 | 910.05 | 910.67 |
| 20 | 924.08 | 925.25 |
| 21 | 938.10 | 938.33 |
| 22 | 951.50 | 951.89 |
| 23 | 972.12 | 972.18 |
| 24 | 924.08 | 923.93 |
| 25 | 924.08 | 925.11 |
| 29 | 924.08 | 924.19 |
| 27 | 937.49 | 937.54 |
| 28 | 937.49 | 937.48 |
| 29 | 937.49 | 937.29 |
| 30 | 946.46 | 946.42 |
| 31 | 944.49 | 945.50 |
| 32 | 962.48 | 963.52 |
| 33 | 1035.95 | 1035.10 |

TABLE 4-continued

Mass validation of the synthesized cPTs.

| Compound | Expected mass | Found mass |
|---|---|---|
| 34 | 967.16 | 967.08 |
| 35 | 953.18 | 953.17 |
| 36 | 978.14 | 978.42 |
| 37 | 984.16 | 984.85 |
| 38 | 963.13 | 963.44 |

The disclosures of each and every patent, patent application, and publication cited herein are hereby incorporated herein by reference in their entirety.

While the invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed:

1. A cyclic compound, which is selected from the group consisting of 29N-2 or 36 [also known as (3S,6S,14S,17S,20S,24S,25aS)-3-((1H-indol-3-yl)methyl)-14-amino-17-(2-amino-2-oxoethyl)-20-((S)-sec-butyl)-1,4,12,15,18,21-hexaoxo-24-(4-(4-(thiophen-2-yl)phenyl)-1H-1,2,3-triazol-1-yl)tetracosahydro-1H-pyrrolo[2,1-f][1,4,7,10,13,18]hexaazacyclotricosine-6-carboxamide]

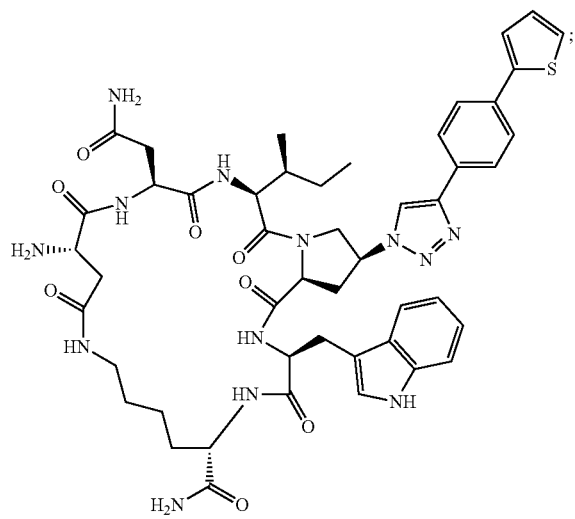 [SMILES: CC[C@H](C)[C@@H]1NC(=O)[C@H](CC(N)=O)NC(=O)[C@@H](N)CC(=O)NCCCC[C@@H](C(N)=O)NC(=O)[C@H](Cc2c[nH]c3ccccc23)NC(=O)[C@@H]2C[C@H](n3cc(-c4ccc(-c5cccs5)cc4)nn3)CN2C1=O]

37 [also known as (3S,6S,14S,17S,20S,24S,25aS)-3-((1H-indol-3-yl)methyl)-24-(4-([2,2'-bithiophen]-5-yl)-1H-1,2,3-triazol-1-yl)-14-amino-17-(2-amino-2-oxoethyl)-20-((S)-sec-butyl)-1,4,12,15,18,21-hexaoxotetracosahydro-1H-pyrrolo[2,1-f][1,4,7,10,13,18]hexaazacyclotricosine-6-carboxamide]

38 [also known as (3S,6S,17S,20S,24S,25aS)-3-((1H-indol-3-yl)methyl)-17-(2-amino-2-oxoethyl)-20-((S)-sec-butyl)-1,4,12,15,18,21-hexaoxo-24-(4-(4-(thiophen-2-yl)phenyl)-1H-1,2,3-triazol-1-yl)tetracosahydro-1H-pyrrolo[2,1-f][1,4,7,10,13,18]hexaazacyclotricosine-6-carboxamide]

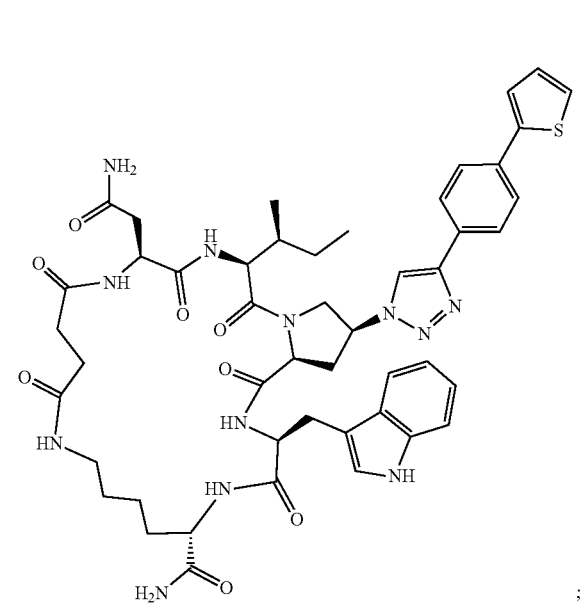

(3S,6S,17S,20S,24S,25aS)-3-((1H-indol-3-yl)methyl)-24-(4-([2,2'-bithiophen]-5-yl)-1H-1,2,3-triazol-1-yl)-17-(2-amino-2-oxoethyl)-20-((S)-sec-butyl)-1,4,12,15,18,21-hexaoxotetracosahydro-1H-pyrrolo[2,1-f][1,4,7,10,13,18]hexaazacyclotricosine-6-carboxamide

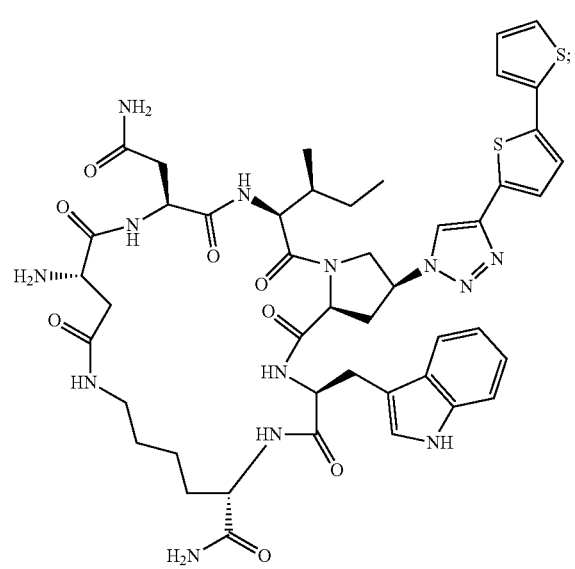 [SMILES: CC[C@H](C)[C@@H]1NC(=O)[C@H](CC(N)=O)NC(=O)[C@@H](N)CC(=O)NCCCC[C@@H](C(N)=O)NC(=O)[C@H](Cc2c[nH]c3ccccc23)NC(=O)[C@@H]2C[C@H](n3cc(-c4ccc(-c5cccs5)s4)nn3)CN2C1=O]

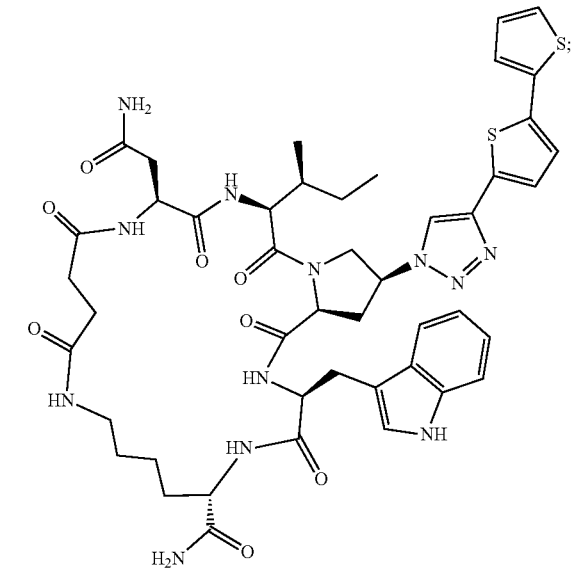 [SMILES: CC[C@H](C)[C@@H]1NC(=O)[C@H](CC(N)=O)NC(=O)CCC(=O)NCCCC[C@@H](C(N)=O)NC(=O)[C@H](Cc2c[nH]c3ccccc23)NC(=O)[C@@H]2C[C@H](n3cc(-c4ccc(-c5cccs5)s4)nn3)CN2C1=O]

71

(3S,6S,14S,17S,20S,24S,25aS)-3-((1H-indol-3-yl)
methyl)-14-amino-17-(2-amino-2-oxoethyl)-20-cyclo-
hexyl-1,4,12,15,18,21-hexaoxo-24-(4-(4-(thiophen-2-
yl)phenyl)-1H-1,2,3-triazol-1-yl)tetracosahydro-1H-
pyrrolo[2,1-f][1,4,7,10,13,18]hexaazacyclotricosine-6-
carboxamide

72

(3S,6S,17S,20S,24S,25aS)-3-((1H-indol-3-yl)methyl)-
17-(2-amino-2-oxoethyl)-20-cyclohexyl-1,4,12, 15,
18,21-hexaoxo-24-(4-(4-(thiophen-2-yl)phenyl)-1H-1,
2,3-triazol-1-yl)tetracosahydro-1H-pyrrolo[2,1-f][1,4,
7,10,13,18]hexaazacyclotricosine-6-carboxamide

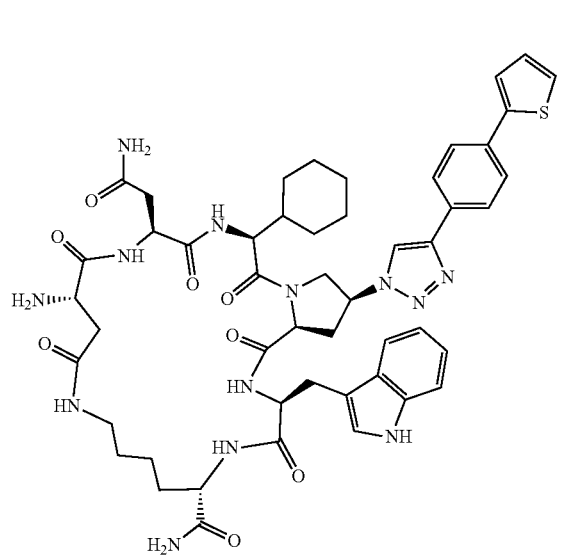

;

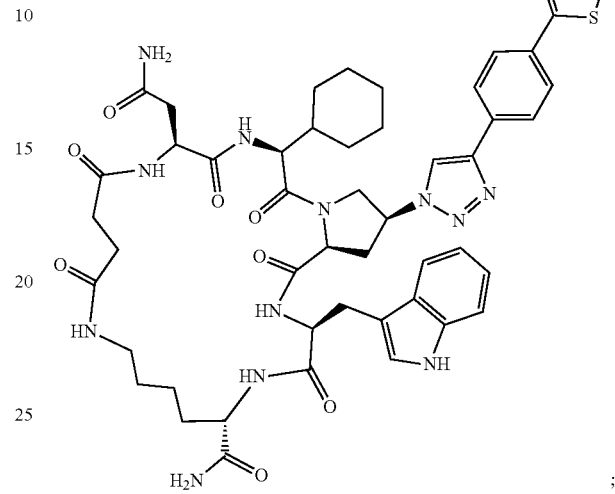

;

(3S,6S,14S,17S,20S,24S,25aS)-3-((1H-indol-3-yl)
methyl)-24-(4-([2,2'-bithiophen]-5-yl)-1H-1,2,3-tri-
azol-1-yl)-14-amino-17-(2-amino-2-oxoethyl)-20-cy-
clohexyl-1,4,12,15,18,21-hexaoxotetracosahydro-1H-
pyrrolo[2,1-f][1,4,7,10,13,18]hexaazacyclotricosine-6-
carboxamide (3S,6S,17S,20S,24S,25aS)-3-((1H-indol-3-yl)methyl)-
24-(4-([2,2'-bithiophen]-5-yl)-1H-1,2,3-triazol-1-yl)-
17-(2-amino-2-oxoethyl)-20-cyclohexyl-1,4,12,15,18,
21-hexaoxotetracosahydro-1H-pyrrolo[2,1-f][1,4,7,10,
13,18]hexaazacyclotricosine-6-carboxamide

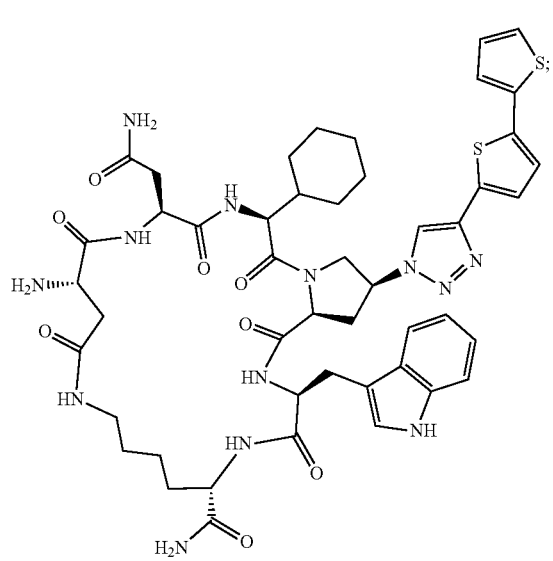 [SMILES: NC(=O)C[C@@H]1NC(=O)[C@@H](N)CC(=O)NCCCC[C@@H](C(N)=O)NC(=O)[C@H](Cc2c[nH]c3ccccc23)NC(=O)[C@@H]2C[C@H](n3cc(-c4ccc(-c5cccs5)s4)nn3)CN2C(=O)[C@H](C2CCCCC2)NC1=O]

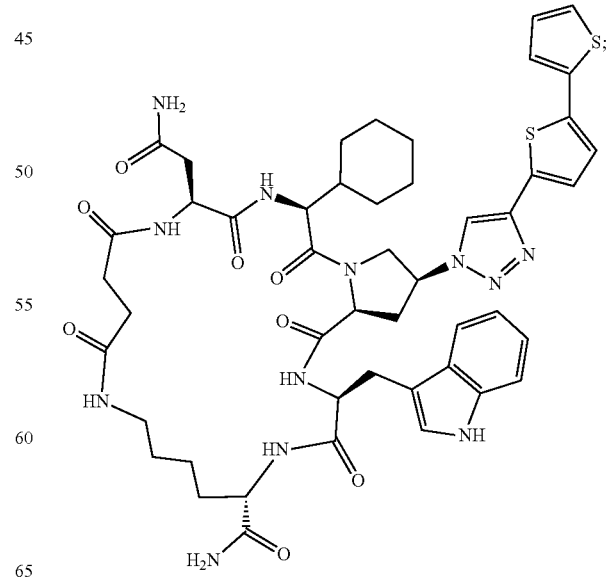

;

73

(3S,6S,14S,17S,20S,24S,25aS)-14-amino-17-(2-amino-2-oxoethyl)-3-(benzo[b]thiophen-3-ylmethyl)-20-((S)-sec-butyl)-1,4,12,15,18,21-hexaoxo-24-(4-(4-(thiophen-2-yl)phenyl)-1H-1,2,3-triazol-1-yl)tetracosahydro-1H-pyrrolo[2,1-f][1,4,7,10,13,18]hexaazacyclotricosine-6-carboxamide

74

(3S,6S,17S,20S,24S,25aS)-17-(2-amino-2-oxoethyl)-3-(benzo[b]thiophen-3-ylmethyl)-20-((S)-sec-butyl)-1,4,12,15,18,21-hexaoxo-24-(4-(4-(thiophen-2-yl)phenyl)-1H-1,2,3-triazol-1-yl)tetracosahydro-1H-pyrrolo[2,1-f][1,4,7,10,13,18]hexaazacyclotricosine-6-carboxamide

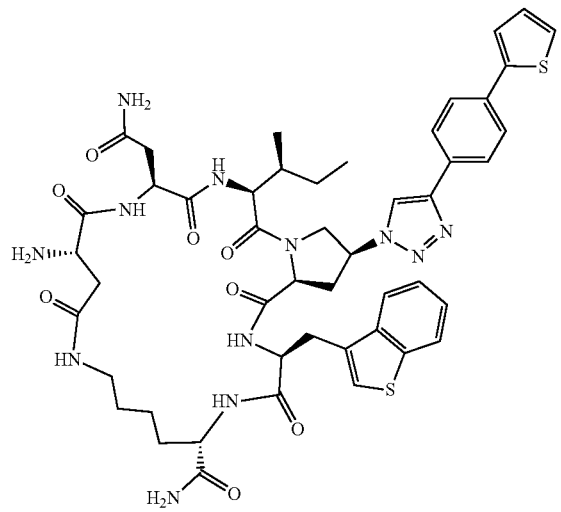

;

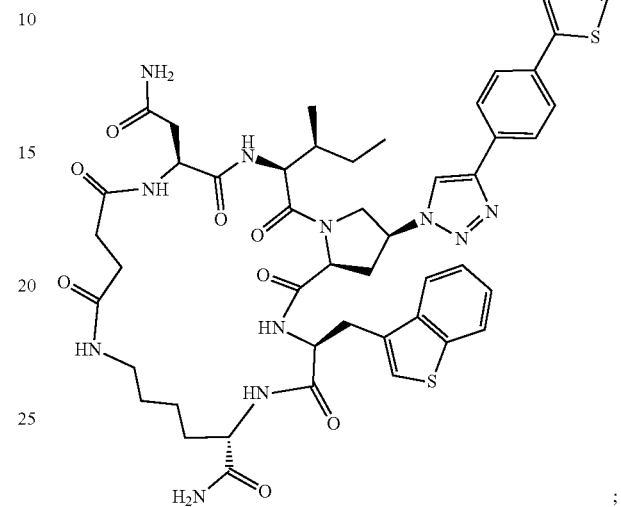

;

(3S,6S,14S,17S,20S,24S,25aS)-24-(4-([2,2'-bithiophen]-5-yl)-1H-1,2,3-triazol-1-yl)-14-amino-17-(2-amino-2-oxoethyl)-3-(benzo[b]thiophen-3-ylmethyl)-20-((S)-sec-butyl)-1,4,12,15,18,21-hexaoxotetracosahydro-1H-pyrrolo[2,1-f][1,4,7,10,13,18]hexaazacyclotricosine-6-carboxamide (3S,6S,17S,20S,24S,25aS)-24-(4-([2,2'-bithiophen]-5-yl)-1H-1,2,3-triazol-1-yl)-17-(2-amino-2-oxoethyl)-3-(benzo[b]thiophen-3-ylmethyl)-20-((S)-sec-butyl)-1,4,12,15,18,21-hexaoxotetracosahydro-1H-pyrrolo[2,1-f][1,4,7,10,13,18]hexaazacyclotricosine-6-carboxamide

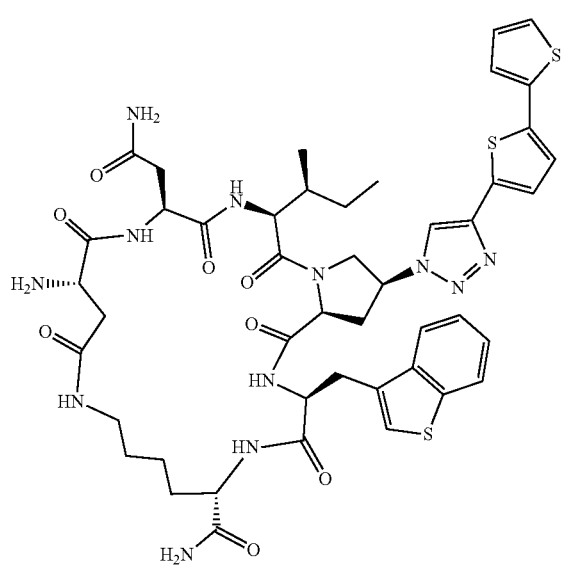 [SMILES: CC[C@H](C)[C@@H]1NC(=O)[C@H](CC(N)=O)NC(=O)[C@@H](N)CC(=O)NCCCC[C@@H](C(N)=O)NC(=O)[C@H](Cc2csc3ccccc23)NC(=O)[C@@H]2C[C@H](n3cc(-c4ccc(-c5cccs5)s4)nn3)CN2C1=O]

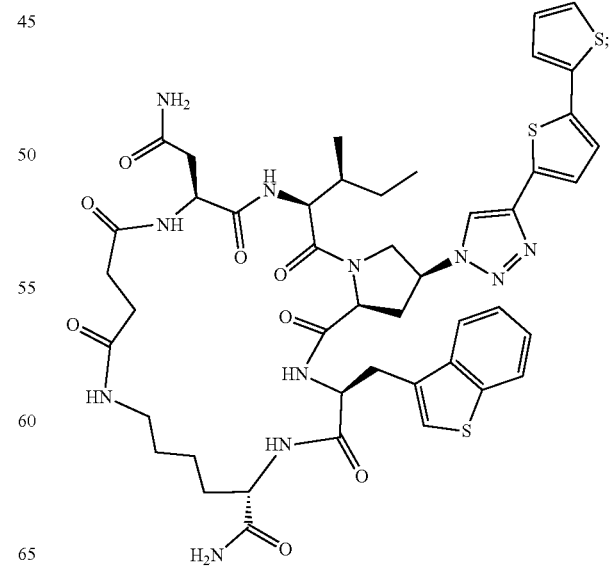

75

(3S,6S,14S,17S,20S,24S,25aS)-14-amino-17-(2-amino-2-oxoethyl)-3-(benzo[b]thiophen-3-ylmethyl)-20-cyclohexyl-1,4,12,15,18,21-hexaoxo-24-(4-(4-(thiophen-2-yl)phenyl)-1H-1,2,3-triazol-1-yl)tetracosahydro-1H-pyrrolo[2,1-f][1,4,7,10,13,18]hexaazacyclotricosine-6-carboxamide

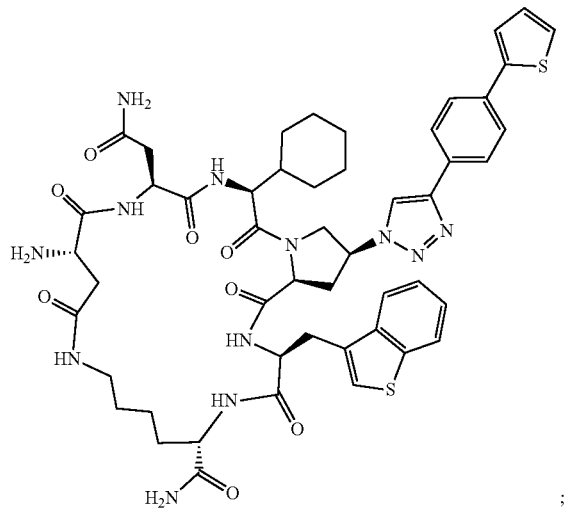 [SMILES: NC(=O)C[C@@H]1NC(=O)[C@@H](N)CC(=O)NCCCC[C@@H](C(N)=O)NC(=O)[C@H](Cc2csc3ccccc23)NC(=O)[C@@H]2C[C@H](n3cc(-c4ccc(-c5cccs5)cc4)nn3)CN2C(=O)[C@H](C2CCCCC2)NC1=O]

((3S,6S,14S,17S,20S,24S,25aS)-24-(4-([2,2'-bithiophen]-5-yl)-1H-1,2,3-triazol-1-yl)-14-amino-17-(2-amino-2-oxoethyl)-3-(benzo[b]thiophen-3-ylmethyl)-20-cyclohexyl-1,4,12,15,18,21-hexaoxotetracosahydro-1H-pyrrolo[2,1-f][1,4,7,10,13,18]hexaazacyclotricosine-6-carboxamide

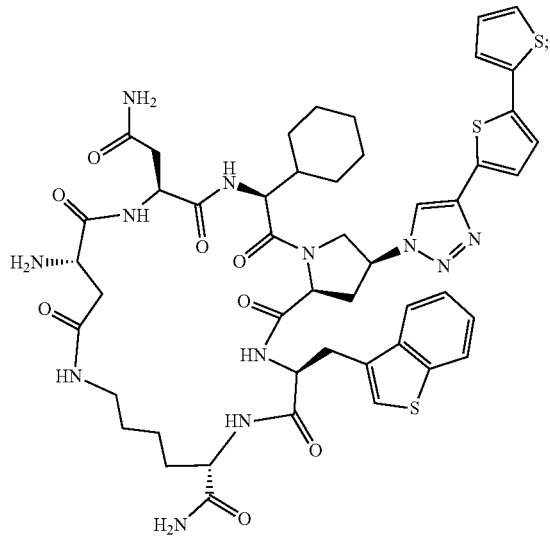 [SMILES: NC(=O)C[C@@H]1NC(=O)[C@@H](N)CC(=O)NCCCC[C@@H](C(N)=O)NC(=O)[C@H](Cc2csc3ccccc23)NC(=O)[C@@H]2C[C@H](n3cc(-c4ccc(-c5cccs5)s4)nn3)CN2C(=O)[C@H](C2CCCCC2)NC1=O]

76

(3S,6S,17S,20S,24S,25aS)-17-(2-amino-2-oxoethyl)-3-(benzo[b]thiophen-3-ylmethyl)-20-cyclohexyl-1,4,12,15,18,21-hexaoxo-24-(4-(4-(thiophen-2-yl)phenyl)-1H-1,2,3-triazol-1-yl)tetracosahydro-1H-pyrrolo[2,1-f][1,4,7,10,13,18]hexaazacyclotricosine-6-carboxamide

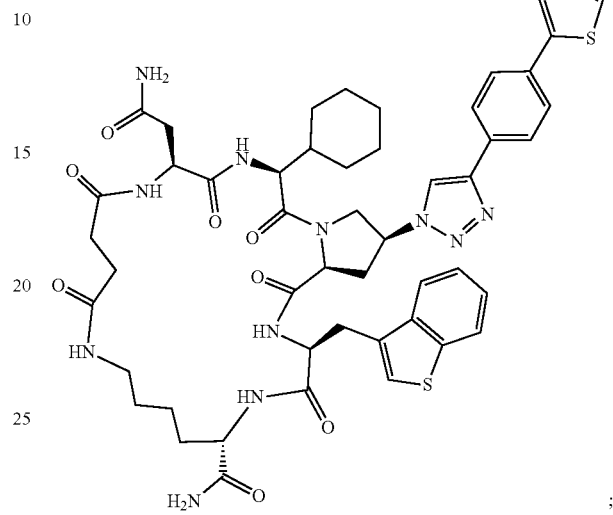

(3S,6S,17S,20S,24S,25aS)-24-(4-([2,2'-bithiophen]-5-yl)-1H-1,2,3-triazol-1-yl)-17-(2-amino-2-oxoethyl)-3-(benzo[b]thiophen-3-ylmethyl)-20-cyclohexyl-1,4,12,15,18,21-hexaoxotetracosahydro-1H-pyrrolo[2,1-f][1,4,7,10,13,18]hexaazacyclotricosine-6-carboxamide

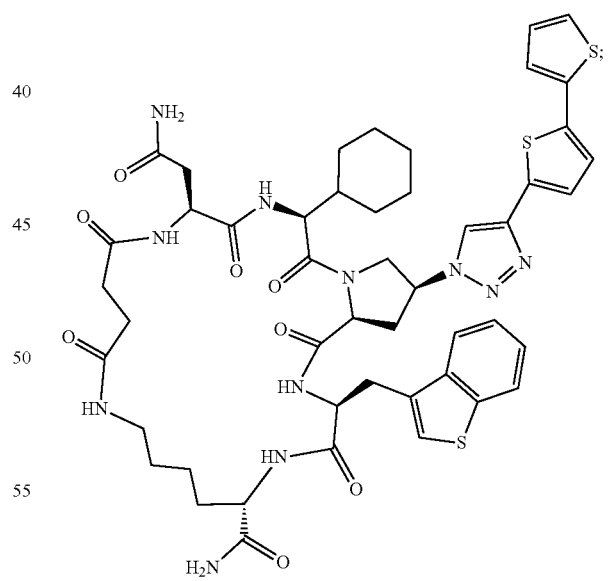

or a salt or solvate thereof.

2. A pharmaceutical composition comprising at least one pharmaceutically acceptable carrier and at least one cyclic compound of claim 1, optionally wherein the compound is complexed through at least one thio group with at least one gold nanoparticle.

3. A method of treating, reducing or preventing HIV-1 infection in a mammal in need thereof or reducing the risk of HIV-1 infection in a mammal at risk of HIV-1 exposure, the method comprising administering to the mammal a therapeutically effective amount of at least one cyclic compound of claim 1.

4. A method of promoting virolysis of HIV-1, the method comprising contacting the HIV-1 with an effective amount of at least one cyclic compound of claim 1, optionally wherein the compound is complexed through at least one thio group with at least one gold nanoparticle.

5. A method of reducing the rate of or preventing entry of HIV-1 into a cell of a mammal, the method comprising administering to the mammal a therapeutically effective amount of at least one cyclic compound of claim 1, optionally wherein the compound is complexed through at least one thio group with at least one gold nanoparticle.

6. A method of preparing a derivatized gold nanoparticle, the method comprising contacting the nanoparticle with at least one cyclic compound of claim 1 to generate a reaction system; and isolating the derivatized gold nanoparticle from the reaction system.

* * * * *